United States Patent [19]

Mortara

[11] Patent Number: 4,630,204
[45] Date of Patent: Dec. 16, 1986

[54] HIGH RESOLUTION ECG WAVEFORM PROCESSOR

[75] Inventor: David W. Mortara, Glendale, Wis.
[73] Assignee: Mortara Instrument Inc., Milwaukee, Wis.
[21] Appl. No.: 582,225
[22] Filed: Feb. 21, 1984
[51] Int. Cl.$^4$ .......................... A61B 5/04; G06F 15/42
[52] U.S. Cl. .................................... 364/417; 128/696; 128/901
[58] Field of Search ................ 364/415, 417; 128/695, 128/696, 700, 701, 702, 703, 704, 705, 708, 901

[56] References Cited

U.S. PATENT DOCUMENTS

| | | | |
|---|---|---|---|
| 3,848,586 | 11/1974 | Suzuki et al. | 128/901 |
| 3,939,824 | 2/1976 | Arneson et al. | 128/901 X |
| 4,000,461 | 12/1976 | Barber et al. | 128/708 X |
| 4,023,564 | 5/1977 | Valiquette et al. | 128/704 X |
| 4,181,135 | 1/1980 | Andresen et al. | 128/704 X |
| 4,263,919 | 4/1981 | Levin | 128/708 |
| 4,422,459 | 12/1983 | Simson | 128/702 |
| 4,458,691 | 7/1984 | Netravali | 128/705 |
| 4,458,692 | 7/1984 | Simson | 128/705 |
| 4,478,224 | 10/1984 | Bailey | 128/901 X |
| 4,492,235 | 1/1985 | Sitrick | 128/705 |

OTHER PUBLICATIONS

*A Flexible Signal–Averaging System for Cardiac Waveforms;* Vincent et al, J. Biomed. Eng., 1980, vol. 2, Jan.
A Multimorphology Computerized Arrhythmia Monitoring System, Hubelbank et al, Comp. in Cardiology, Sep. 1978.
IBM Tech. Disclosure Bull., "Portable ECG Event Detector", vol. 25, #7A, Dec. 1982.

*Primary Examiner*—Jerry Smith
*Assistant Examiner*—Clark A. Jablon
*Attorney, Agent, or Firm*—Fitch, Even, Tabin & Flannery

[57] ABSTRACT

A waveform processor for processing waveforms of the ECG type from surface electrodes connected to the human body. Differential lead waveforms are sampled by a fast, high resolution A/D converter which are thereafter provided to a preprocessor where filtering and a reconstruction of the leads waveforms takes place. The waveforms are then detected, classified, and averaged to form composites of the X, Y, and Z terminal leads. Special filtering is used to detect the high frequency low amplitude features of the composite waveforms.

20 Claims, 40 Drawing Figures

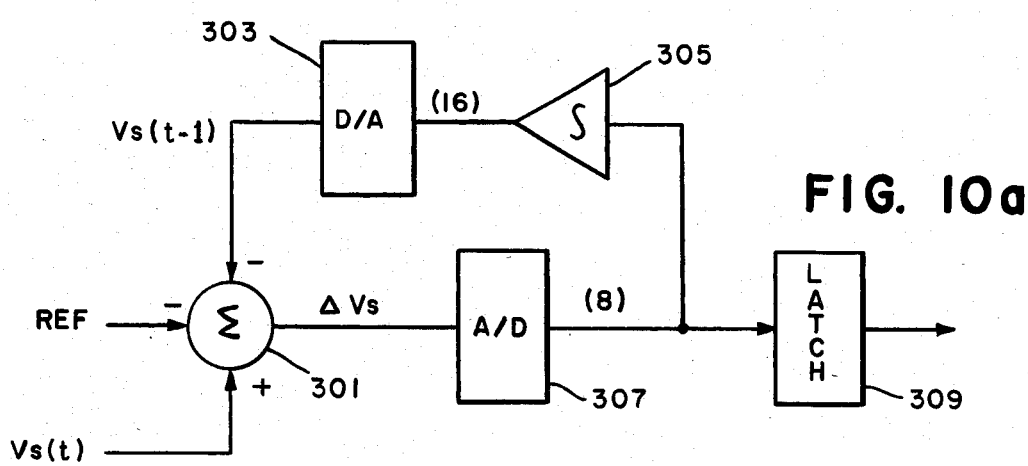
FIG. 10a
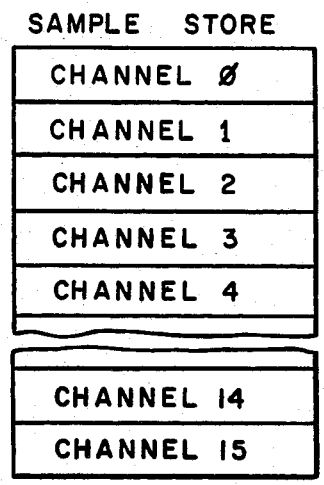
FIG. 10b
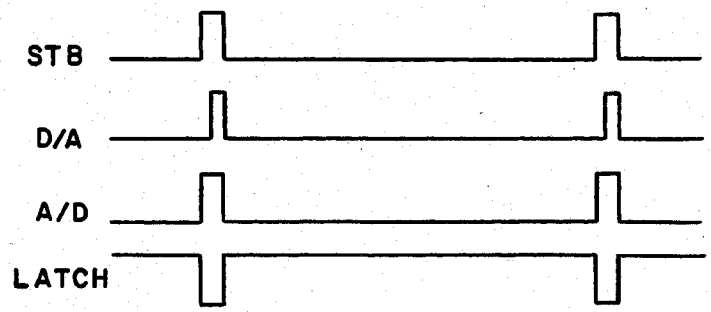
FIG. 10c
FIG. 10d
FIG. 10e
FIG. 10f

HIGH RESOLUTION ECG WAVEFORM PROCESSOR

BACKGROUND OF THE INVENTION

The invention pertains generally to a processor for waveforms, such as those obtained from the human body by surface electrodes during cardiac depolarizations, i.e. ECG waveforms, and is more particularly directed to detecting particular features of those waveforms requiring analysis at high resolutions.

The electrocardiographic (ECG or EKG) waveform has been the object of intensive study for a long time. Generally, the amplitude and waveshape of the QRS complex of such waveforms are of interest in the diagnosis of cardiac insufficiency and disease. Analog devices for plotting the waveshapes of heartbeats have been used extensively and numerous apparatus have been provided for detecting the peak amplitude of the R-segment and the onset of the waveform. Others devices have compared the shapes of the T-segment against emperical criteria to determine factors concerning cardiac function. All of these devices however, require human interpretation of the results and are generally of low resolution.

More recently the ECG has been studied in an attempt to discriminate small amplitude high frequency potentials occurring in the waveforms. Three of these microvolt level signals generating considerable interest today are His bundle potentials, high frequency components of the P-segment and QRS-segment of the waveform, and post-QRS segment "late potentials". It is believed that other useful microvolt signal information will yet be discovered but has not been identified because of the lack of instrumentation available to measure it reliably.

His bundle potentials, named for their discoveror, and other special high frequency features in the ECG waveform are electrical displays of the subcycle electrical activity taking place in the depolarization cycle other than just the major atrial and ventricular contractions. By being able to detect these special features, researchers will be better able to map the entire cardiac cycle and possibly diagnose problems of latent dysfunctions that are hidden today in the ECG waveform.

Small amplitude, high frequency microvolt signals after the QRS complex which are termed "late potentials" are useful in predicting ventricular tachycardia in post myocardial infarction patients. See Uther et al. "The Detection of Delayed Activation Signals of Low Amplitude in the Vector Cardiogram of Patients with Recurrent Ventricular Tachycardia by Signal Averaging", Excerpta Medica, Amsterdam, 1978, pp. 80–82. It is hypothesized that the scarring caused by an infarction produces nonuniform borders which modify the natural depolarization process to produce these potentials possibly by slowing the propagation of the normal potential through the tissue or by increasing the path length over which it travels.

Although all of these microvolt level signals are now useful and it is believed researchers will begin isolating others, these signals are extremely difficult to detect with consistency. The initial discrimination problem is found in the form of the ECG waveform itself. The amplitude of the QRS segment in a ECG signal is relatively high and at a relatively low frequency compared to those of the features of interest, which have a relatively high frequency and relatively low amplitude. Because of the difference in amplitudes between that which is measured and that which is of interest, a high resolution detection system must be used. In the digital context increasing the resolution in a detection apparatus generally means increasing the cost for including devices and memories of higher bit capacities.

Further, because of the frequency difference between the QRS complex and the microvolt potentials, selective detectors with various special characteristics must be used. For example to detect "late potentials" for tachycardia prediction, a high pass filter without any ringing time constant is necessary. This is because the "late potentials" which follow the high energy QRS-segment of the waveform will be masked by any ringing caused by the high energy portion of the signal. Additionally, base line shift of the ECG signal is detrimental because the DC component of the ECG signal may float above and below an average to an extent greater than the microvolt amplitudes one is trying to detect.

The input beat waveforms of an ECG signal may also contain false or odd beats such as muscle artifacts, noise, and ectopic beats. High frequency low amplitude features of an ECG signal are hard to detect in these circumstances because each beat cycle of the depolarization may be different from any other beat cycle and different depending on the positioning the electrodes measuring the waveform. Therefore, to be of real use a large number of beat waveforms must be summed to produce a composite average waveform over a number of beats while using objective criteria to reject spurious data. Only when a representative composite beat waveform is free from noise, base line shift, and odd beats can the microvolt potentials of interest be detected reliably.

Even when a number of waveforms have been sampled and odd or inconsistent beats have been eliminated therefrom, the problem remains as how to average the beat waveforms which are sampled from non-aligned times in the sampling process. Although there are landmarks in each beat, they can vary from cycle to cycle and provide only a relative alignment. The alignment of the waveforms is further problematical because of the effects of noise and the voltage variations of the waveforms on a beat to beat basis. There are several sources of induced voltage variation in these waveforms, but respiration is probably the main one with a stable heart rate. If the beat waveforms are not aligned with accuracy, the error in alignment acts as a filter to which frequency components of the composite waveform. Therefore, in the detection of microvolt potentials a misalignment during the averaging process can reverse the gains produced by averaging and mask these signals altogether.

SUMMARY OF THE INVENTION

To overcome these and other problems encountered in the measurement and detection of waveforms, particularly the high frequency, low amplitude features of an ECG waveform, the invention provides a high resolution waveform processor.

The waveform processor comprises means for sampling a plurality of ECG waveforms to provide sample data, means for identifying average beat waveforms from the sample data, means for averaging the average beat waveforms, and means for detecting high frequency, low amplitude features from the averaged beat data. The waveform processor may additionally comprise means for displaying the averaged beat waveforms and/or the detected features.

In a preferred hardware implementation the waveform processor includes a signal conditioning means which digitizes a plurality of analog signals input from surface electrodes placed on a patient to sense cardiac depolarizations, a preprocessor which buffers the digitized data and provides preprocessing functions which are independent of signal content, and a main processor which receives the digitized data and other preprocessed digitized data to identify average beat waveforms. The main processor thereafter averages the average beat waveforms and detects the features desired.

The signal conditioning means includes a microprocessor based analog to digital converter which is specifically adapted to generate high resolution digital samples of ECG waveforms with a minimum number of bits. The microprocessor of the signal conditioning means controls a multiplexer with a plurality of input channels to provide one of the analog ECG waveforms sampled at an input junction. Under control of the microprocessor, the input signal is differenced at the input junction with another analog signal which is representative of the value of the input signal one time period earlier. The difference is converted to a digital sample and transmitted to a latch for output to the preprocessor. The analog signal differenced with the input signal is generated from a digital to analog converter with a much higher bit resolution than the analog to digital converter. Because it is the difference between the two signals that is converted to a digital number, all of the bit resolution of the A/D converter is applied to a smaller range.

This operation is of significant advantage in providing high resolution samples of multiple input channels at a high clock rate while using a minimum length digital word. The high resolution of the samples is needed so that the low amplitudes of the special features of the waveforms can be accurately measured.

The signal conditioning means further includes a transmitter which takes each digital sample from the latch and transmits the digital word over a transmission line in a serial fashion to the preprocessor. Besides the digital word the transmitted data additionally have a plurality of framing bits interposed between the data bits in a unique pattern. The framing bits are placed in the transmitted word to provide means for detecting errors in the data word once it reaches the preprocessor.

The preprocessor is a microprocessor based data control and processing device using an input buffer to communicate with the signal conditioning means and an output buffer to communicate with the main processor. The preprocessor receives the transmitted data with a receiver and decodes the framing bits such that any data which are in error can be discarded. If the data are judged to be accurate, the preprocessor stores them in the input buffer.

During a preprocessor cycle the sampled data in the input buffer are read into the preprocessor and certain preprocessing functions performed thereon. After the preprocessing functions are completed, the sampled data and additional preprocessed data are stored in the output memory buffer. The preprocessor shares access to the output memory buffer with the main processor and notifies the main processor data are ready by generating an interrupt signal at predetermined times.

The preprocessor functions include integrating the data samples to provide a set of reconstructed data samples from the difference inputs; bandpass filtering the sampled data to provide detection and labeling data; filtering the sampled data for noise; summing a plurality of the samples together for one lead to perform alias component filtering; and summing the nominally equivalent samples together to produce a single output for each lead.

The preprocessor therefore functions to accomplish two major tasks, that of compressing the data by preprocessing and that of buffering the data between the signal conditioning means and the main processor. The preprocessing of the data greatly enhances the power of the main processor, as data which have certain attributes have already been provided without using the main processor time. It is noted that the preprocessor functions are all data content independent and do not include calculations on the sampled data. The separation of the preprocessing functions from the calculation functions are advantageous in that if a different evaluation were warranted, the signal conditioning means and preprocessor would not need to be changed. Only the calculation functions which are executed by the main processor would have to be reprogrammed.

The main processor takes the preprocessed data out of the output buffer and detects and labels each beat waveform. Alignment and averaging of the waveforms take place thereafter but before these waveforms are input to specialized detector means.

The detection and labeling of the beat waveforms are accomplished with the assistance of the bandpass filtered data from the preprocessor. An initial template is formed from the bandpass data samples and a best fit for the template is formed by minimizing the ratio of the absolute difference of the template samples and the data samples to the absolute sum of the template samples and the data samples.

Those waveforms which cannot be templated to a certain minimum ratio or which fail to meet other objective criteria as to length, peak amplitude, or dominate type are discarded as nonuseable in a composite average. An alignment routine in the preprocessor then generates a fiducial timing mark in each waveform by using a sliding template to further minimize the best fit. The average type of waveforms with their fiducial timing mark are then averaged to form a noise free composite which is not contaminated by odd beat waveforms which could mask the high frequency, low amplitude special feature to be detected.

The composite average ECG waveform is subsequently input to one or more of a plurality of specialized high pass filters to detect the special features of interest. In a preferred embodiment one of the detection means is a finite impulse response filter which produces no phase shift or amplitude phase reversals. This filter is particularly advantageous in the detection of His bundle waveforms.

In another preferred embodiment one of the detection means is a digital filter synthesized from a four-pole Butterworth filter in which the output data are filtered in both a reverse and forward time direction. This filter is particularly advantageous in detecting post QRS "late potentials" which are predictive of ventricular tachycardia in post myocardial infarction patients.

These and other objects, features, and aspects of the invention will be more fully understood and better described if a reading of the following detailed description is undertaken in conjunction with the accompanying drawings in which:

BRIEF DESCRIPTION OF THE DRAWINGS

FIGS. 5a-5f are detailed circuit diagrams of various components of the signal conditioning means illustrated in FIG. 5;

FIG. 10a is a system block diagram of the functional operation of the analog to digital conversion for the signal conditioning means illustrated in FIG. 2;

FIG. 10b is a pictorial representation of the sample store for the microprocessor illustrated in FIG. 5;

FIGS. 10c-10f are waveform diagrams of various control signals for the signal conditioning means illustrated in FIG. 5;

DETAILED DESCRIPTION OF THE PREFERRED EMBODIMENT

Figure 1:
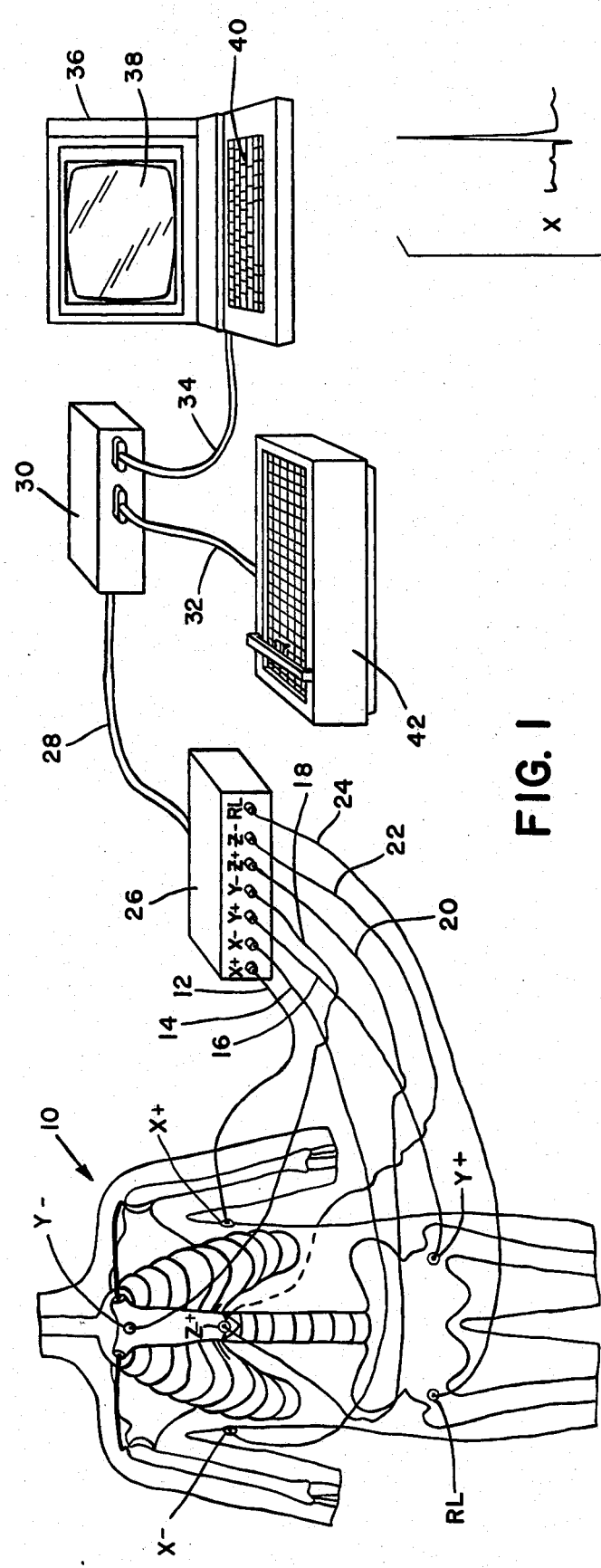
FIG. 1 is a pictorial representation of a waveform processor constructed in accordance with the invention.

In FIG. 1 there is illustrated a waveform processor which is particularly adapted to perform the processing of waveforms obtained from a human body by surface electrodes during cardiac depolarizations. These waveforms, typically termed ECG or EKG waveforms, are generated by attaching surface electrodes to a patient 10 at particular locations. In the illustrated embodiment X, Y, and Z potentials are measured by leads 12-22 representing the combinations of the surface potentials X+, X−, Y+, Y−, Z+, and Z−, respectively. A lead 24 is connected to the right leg surface electrode and is driven by the system from output RL to produce a feed back potential such that common mode rejection is enhanced. The placement of the electrodes envisions that the potential across the cardiac chamber is measured in three axes any two of which define a plane such that three mutually perpendicular planes are formed. Electrodes X+, X− form one axis at the fifth intercostal position under each arm at the sides, electrodes Z+, Z− form another axis perpendicular thereto horizontally on the sternum and directly in back thereof, and electrodes Y+, Y− form another axis perpendicular thereto vertically on the sternum and the top of the left leg.

The analog waveform signals from leads 12-24 are input to a signal conditioner 26 which is located relatively near the patient under study so that the electrode lead lengths are kept reasonably short and stray capacitance is reduced. If the capacitive coupling of the leads is too great, noise such as 60 cycle AC and other environmental noise will be superimposed on the input waveforms. The signal conditioner 26 digitizes the analog potentials input from the leads and transmits the digitized data via a transmission line 28 to a main processor apparatus 30. The main processor apparatus 30 communicates with a CRT terminal 36 and a graphic plotter 42 through respective transmission lines 34 and 32.

An operator of the system by typing in commands on a keyboard 40 and following the instructions displayed on the screen 38 of the CRT terminal 36 can produce several different outputs from the plotter 42. The outputs which are available to the operator are wide band, low gain representations of the X, Y and Z waveforms, wide band, high gain plots of the X, Y and Z waveforms, plots of detected special features of the waveforms, and special numbers indicative of particular values for some of the special features. In particular the detected features of the waveforms are provided by high pass filtering the input data with a finite impulse response filter (FIR) and high pass filtering composite average data with a bidirectional four pole Butterworth filter.

Figure 3:
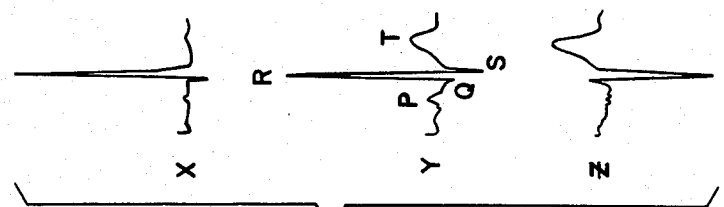
FIG. 3 is a pictorial representation of the waveforms for the X, Y, and Z leads which are measured with the waveform processor illustrated in FIG. 1.

FIG. 3 shows pictorial representations of the input waveforms of the X, Y and Z potentials respectively. Each cardiac waveform can be expressed as a composition of a number of segments or particular features. This is best seen in the Y waveform where the segments P, Q, R, S, and ST are visible as separately discernable features in the overall waveform. As is well known, these segments have a definite physical correspondence to the mechanical aspects of the heart rhythm. For example, the R segment peak is the depolarization causing the contraction of the left ventricle. Each of the analog signals input for the X, Y and Z waveforms consist of a successive train of these beat waveforms. It is noted that the periodicity of the beats depends on heart rate and the physiological accuracy of the cardiac cycle in the particular patient. Each individual beat waveform may differ slightly in amplitude and shape from a representative one because of noise, movement, muscle artifacts, and respiration. Also evident is the variation in waveform caused by the different placement of the electrodes on the patient.

It is evident that the most discernable feature in each waveform is the QRS complex, which is of relatively high amplitude and relatively low frequency compared to microvolt potentials such as the His bundle potentials or the "late potentials" which may follow the QRS complex. These special features are not illustrated on the waveforms shown because of the scale difficulties but are of a microvolt amplitude compared to the millivolt amplitude of the R segment and are of frequencies in the range of 50-250 Hz as compared to R segment dominant frequencies in the range of 10-30 Hz.

As will be more fully explained hereinafter the waveform processor is particularly adapted to detect these relatively high frequency and relatively low magnitude features of the best waveforms. This discrimination is provided by the waveform processor in an advantageous manner by first taking high resolution samples from the particular leads and digitally filtering and processing the waveforms to form a composite average waveform which is substantially free of noise and other artifacts while still containing the high frequency, low amplitude features. The composite waveform is then detected by special filtering techniques to highlight the particular feature desired before being displayed on the plotter 42.

Two particular embodiments will be described wherein His bundle potentials are detected by a FIR filter, and "late potentials" following the QRS complex which are predictive of ventricular tachycardia are detected by a four pole Butterworth filter. It will be evident that once a high resolution composite average has been formed, other high pass special filtering techniques or the like can be used to detect other high frequency, low amplitude features of the waveforms.

Figure 2:
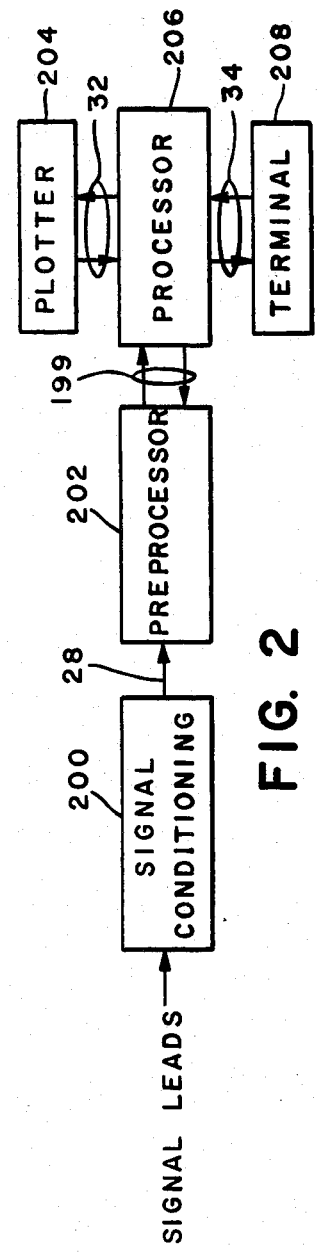
FIG. 2 is a hardware block diagram of the waveform processor illustrated in FIG. 1.

The generalized hardware block diagram for the waveform processor is more fully illustrated in FIG. 2. The signal leads having information concerning the ECG waveforms are input to signal conditioning means 200. The signal conditioning means 200 amplifies the individual waveforms and digitizes them for transmission to a preprocessor means 200. The transmission of the data is in a serial format via the transmission line 28. The preprocessor means 202 buffers the sample data and applies certain preprocessing functions to the data before passing them to a main processor 202 via a communication link 199.

The main processor 206 performs the generalized calculations necessary for detection of low amplitude, high frequency features in the ECG waveforms and system executive functions. When the special features have been detected, they and other representations of the input samples can be output on the plotter 204 in a number of different formats via the communication link 32. The CRT terminal 208 is provided a communication link 34 with the processor 206 to provide interactive communication and control of the system, particularly the plotter functions.

The communication links 32, 34, 199 with the main processor 206 are interrupt driven to cause digital communication in an advantageous manner whereby each device can access the main processor at asynchronous times. Since the data samples are being input at a constant rate by the signal conditioning means 200, the preprocessor 202 buffers the input samples prior to transferring data blocks by the interrupt driven communication protocol.

Each of the primary hardware parts of the system, the signal conditioning means 200, the preprocessor 202, and processor 206, are microprocessor based to produce a system that advantageously uses the power of digital processing to produce a high resolution waveform processor capable of sampling and processing large quantities of data from the input leads. A large quantity of data at the high resolution provided by the system is necessary for providing a highly accurate reproducible detection of the low amplitude, high frequency features of the ECG waveforms.

Figure 4:
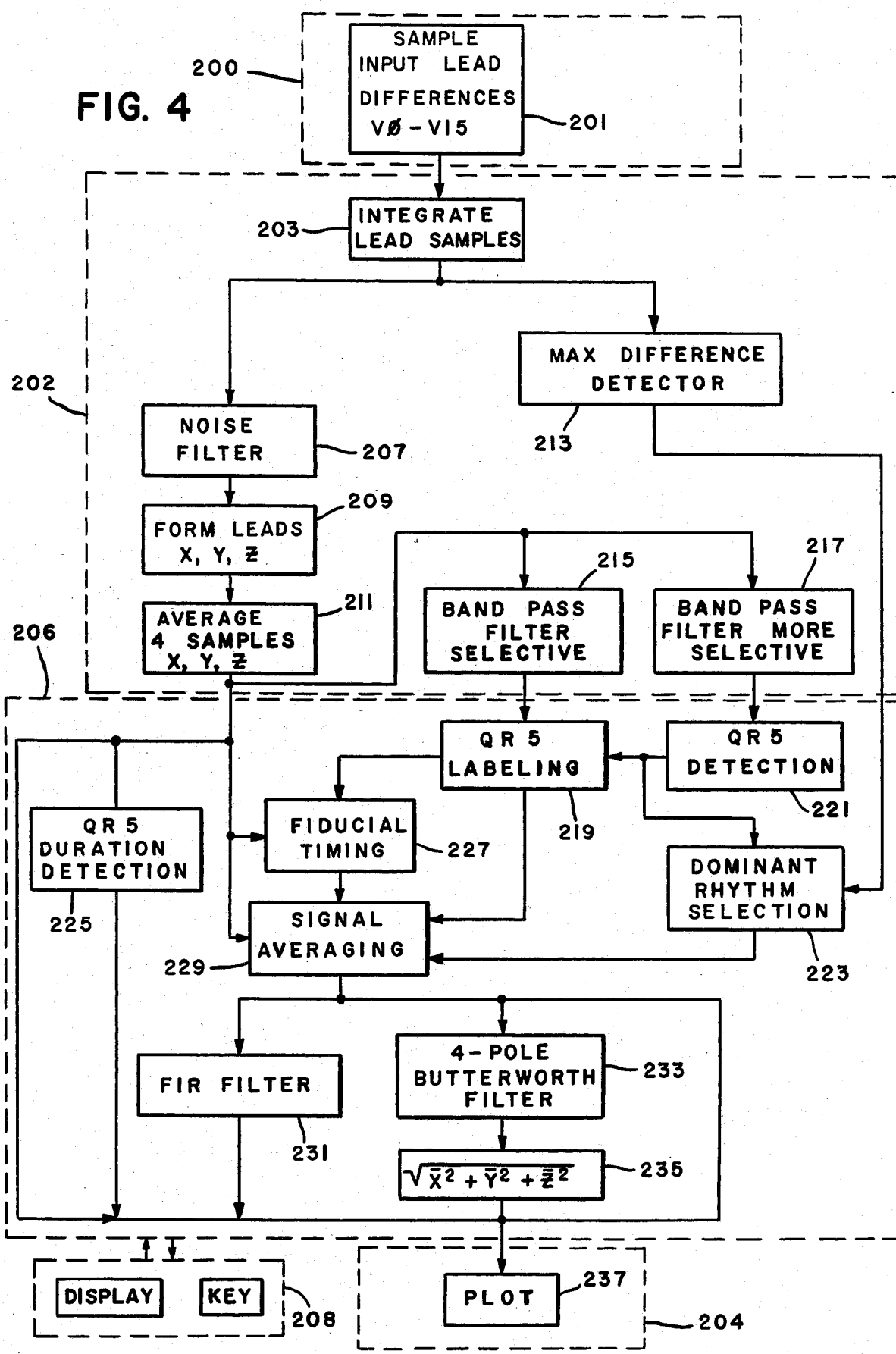
FIG. 4 is a function diagram illustrating the operational functions for the signal conditioning means, the preprocessor and the main processor of the waveform processor illustrated in FIG. 2.

In FIG. 4 there is illustrated a functional system block diagram for the major operational functions of the system illustrated in FIG. 2. The signal conditioning means 200 functions in block 201 to input differences of the lead values LL, LA, V1-V14 where these variables correspond to multiple values of the electrode potentials $X+$, $X-$, $Y+$, $Y-$, and $Z+$, $Z-$ as will be more fully explained hereinafter. These lead differences are the subtraction of an input sample from the previous input sample value for the same lead, essentially taking the first derivative of the lead samples. Taking a difference in this manner produces a smaller bit size word with which to transfer data while still producing high resolution data in the system. In general, the signal conditioning means 200 inputs samples of each of 16 leads at a 4 kHz rate. The signal conditioning means constantly sends data to the preprocessor 202 at a 4000 samples/sec/lead rate and stores them in blocks of 256 samples. The blocks of 16×16 samples are used for buffering purposes as will be more fully explained hereinafter.

After a block of samples is transferred from the signal conditioning means 200 at the input sampling rate, the preprocessor means 202 in functional block 203 integrates the different samples back to the original values they had before the differences were taken. Next a noise filter in block 207 operates on the incoming data stream to filter out high frequency noise characteristics above a cutoff frequency of 500 Hz.

When this basic filtering has been accomplished the X, Y, and Z lead signals are formed in functional block 209 from nominally equivalent signal samples. The objective is to reduce noise introduced into the amplification process by summing samples of the same lead in parallel. The X lead is formed equivalent to the summation of $(V1-V2)+(V4-V6)+(V11-12)$, the Y lead is formed as the equivalent of $(V3-V2)+(V7-V8)+(V3-V14)$, while the Z lead is formed from the equivalent of $2*V1-(RL-V5)+(V9-V10)$. Thereafter, the X, Y, and Z samples are averaged over four consecutive samples by an alias filter in block 211. This averaging is to prevent the aliasing of signal components above the Nyquist frequency of 500 HZ and to enhance high frequency noise rejection. Thus the output from the preprocessor 202 is at the data rate of 1000 samples/sec/lead.

In addition to transferring these 1 KHz signals of the X, Y and Z lead sample to the main processor 206, the preprocessor samples are additionally passed through a first bandpass filter in block 215 and a second bandpass filter in block 217. The bandpass filter 217 is more selective in frequency than the band pass filter 215 such that a smaller frequency band is passed through to the main processor 206. These bandpass filters are to assist in the detection and morphological labeling of the beat waveforms. The motivation for using the band pass filters on the raw data samples is the noise versus frequency spectra of the main part of a beat waveform or the QRS segment. The major components of the noise spectrum in a beat waveform are represented by low frequency baseline shifts and high frequency muscle artifacts. Conversely, the QRS segment frequency spectrum peaks in the region of 8 to 10 Hz and is relatively insignificant below 5 Hz and above 30 Hz. Thus, the greatest signal to noise ratio for QRS detection and labeling can be obtained by bandpass filtering the raw data samples to eliminate frequencies other than the major QRS frequency components. The reason for the difference in the bandwidths of the two filters is that in the detection phase the rejection of low frequency events, principally T segment waves, and high frequency artifacts is enhanced by a narrower bandwidth. Once a detection has occurred, a wider bandwidth for the second bandpass filter allows a greater discrimination between the individual QRS morphologies.

It should be noted that the raw data are transmitted to the main processor 206 unchanged. The filtered data will later be used in the discrimination of the beat waveforms in the raw data but the process has not changed the data in any manner. It is an advantage of this digital processing system that the filtered data samples can be obtained in blocks 215, 217 without modifying the raw data, which still include the special features for detection. By this technique special information has been extracted from the input data which will be of further use in processing that data.

Still further, the preprocessor 202 functions to detect the maximum amplitude difference between individual samples of a lead in block 213. This maximum difference detector is to allow the device to discriminate pacing pulses if the patient under consideration has an electronic pacemaker. The maximum detected difference, which is indicative of the maximum slope of the waveform, can then be compared against a reference value indicative of the maximum slope which would be expected in a human without a pacemaker. If the maximum slope detected is greater than that expected for the patient on his own, then it is determined the heart is being artificially stimulated, i.e., by a pacemaker. A flag indicating that a pacing signal has been detected is then transmitted to the main processor 206.

Therefore, the preprocessor 202 outputs four separate groups of information to the main processor 206 including a raw data signal from function block 211, a selective bandpass filtered signal from function block 215, a more selective bandpass filtered signal from function block 217, and a maximum difference signal from function block 213. The main processor 206 receives the more selective filtered signal from function block 217 and performs a detection operation on the QRS waveform in function block 221. The system passes this detection information to a labeling function block 219 and a dominant rhythm selection block 223 after performing the function. Basically, QRS detection is a search for a maximum in the composite magnitude of the detection filter data samples where the composite magnitude is defined as the sum of the magnitudes of the X, Y, and Z input leads.

Concurrent with the detection process, the input samples from the bandpass filter in block 215 is continuously compared with previously adopted templates of various QRS morphologies. A QRS signal is then labeled as to type according to the best fit for its morphology. If no template matches adequately a new template is created from the bandpass filter samples. Once a QRS signal has been detected and labeled, a fiducial timing mark can be entered into the data if they are of the dominant type. The fiducial timing function is performed in function block 227 and encompasses aligning the detected and labeled beats to a best fit and providing a mark in each beat waveform in the same relative position.

Additionally, from the output of the maximum difference detector in block 213 and the QRS detection in block 221, a dominant rhythm selection function in block 223 is performed. This function is provided in order to ensure the rejection of odd or ectopic morphologies during the averaging function. The function detects a dominant rhythm and identifies a QRS waveform as either that of the dominant type or not.

Initially, upon data acquisition the first QRS encountered is tentatively identified as the dominant type. This identification is retained as long as no QRS (except the electronically paced complexes) is encountered which follows a longer RR interval than the observed average and which does not match the dominant type. If such a QRS is encountered it is newly labeled as the tentative dominant type. This process continues until a satisfactory minimum number of dominant cycles have been identified, at which time the tentative identification is made permanent. Those QRS complexes which are not of the dominant type are excluded from the average to prevent contamination of the signal.

From the outputs of the fiducial timing function block 227, the QRS labeling block 219, the dominant rhythm selection function block 223, and the raw data for the X, Y, and Z leads, a signal averaging block 229 combines the raw data. The averaging consists of the signal summation and normalization of the raw data while excluding noise and the ectopic beat waveforms. The averaging is accomplished using the proper fiducial timing mark applied from the fiducial timing function block 227. An adequate dynamic range is retained to preserve the QRS segment amplitudes accurately for display of the raw average data and for detection of the low amplitude high frequency features contained therein.

Subsequent to the signal averaging function, the data are filtered by a high pass frequency filter in block 231 of the finite impulse response type. Additionally the signal is filtered by a four pole Butterworth filter indicated by block 233. After filtering by block 233, the square root of the sum of the squares of the individual lead signals is taken by a function block 235 over a predetermined part of the averaged beat waveform.

The raw data output, the output of the signal averaging block 229, the output of the function block 231, and the output of the function block 235 are all provided to a function block 237 of the plotter which plots the data to display particular features of each output. These outputs are in response to commands for plotter operation by the operator. The commands which produce these operations are typed into the system with the CRT terminal 208 and are handled by a system operating program in the main processor 206.

The wide band or "raw" presentation of the data is generally useful in two purposes. First in the absence of the filtering, obviously no misleading effects should be visible in the output plot. Small deflections seen in the wide band recording thus cannot be the results of any filtering. Furthermore, the quadrant of an observed deflection in the waveform is the real quadrant, this characteristic being useful whenever the vector orientation of the deflection may have significance. However, the utility of the wide band presentation is limited by the presence of the low frequency signal components causing the output recordings to go off scale. For this reason the gain of the unfiltered presentation must be kept lower than that for high pass filtered data.

The FIR filter 231 is primarily used to remove the low frequency components which would limit the useful degree of amplification of the wide band recording. Particularly this is the high amplitude, low frequency QRS segment of the signal. The FIR filter 231 avoids most of the undesirable characteristics of typical high pass filters, such as ringing other forms of extended transient response. In the preferred implementation, the FIR filter 231 used has an absolute upper limit of 8 milliseconds as the duration of a transient response.

These characteristics are most important immediately following the P segment and QRS segment of a beat waveform. Absence of ringing means no zero crossings in the output waveform will appear as an artifact of the FIR filter in the regions of interest. The finite impulse response of 8 milliseconds indicates that no effects of the P wave or QRS wave will be present 8 milliseconds following the end of such segment. Both of these characteristics are useful for detecting small signals shortly after much larger signals.

Another potentially useful feature of the FIR filter 231 is its preservation of the polarity and amplitude of the signals whose frequency components are largely above 50 Hz. This means that, like the wide band recordings, the vector orientation of the high frequency signals such as His bundle deflections can be directly inferred.

The bidirectional Butterworth filter 233 is used specifically to enhance the detection of post QRS "late potentials". The objective of the bidirectional filter 233 is to eliminate any effects of the filter response which might blur QRS onset or termination. This is accomplished by filtering the average signal in a conventional manner up to the central portion of the QRS segment and then filtering in a reverse time direction the latter half of the cardiac cycle starting at the end of the cycle. The result is a sharply defined QRS onset and termination allowing accurate measurement of the QRS duration. This filtering provides a more unambiguous pattern for the detection of the "late potentials".

A QRS duration detection function of block 225 also takes the average samples and detects the ostensible onset and termination of the composite waveform. In this detector, the onset and termination are obtained from an algorithm conforming to the American Hospital Association Rules for Visual Location of these landmarks. The output of the QRS duration detector 225 is provided to the plotter so that marks indicating onset and offset can be applied on particular waveforms. Other functional operations of the waveform processor will be more apparent in the following detailed description. However, these functions shown in FIG. 4 however delineate the major operations necessary for detection of the small amplitude, high frequency special features of the waveform inputs.

Figure 5:
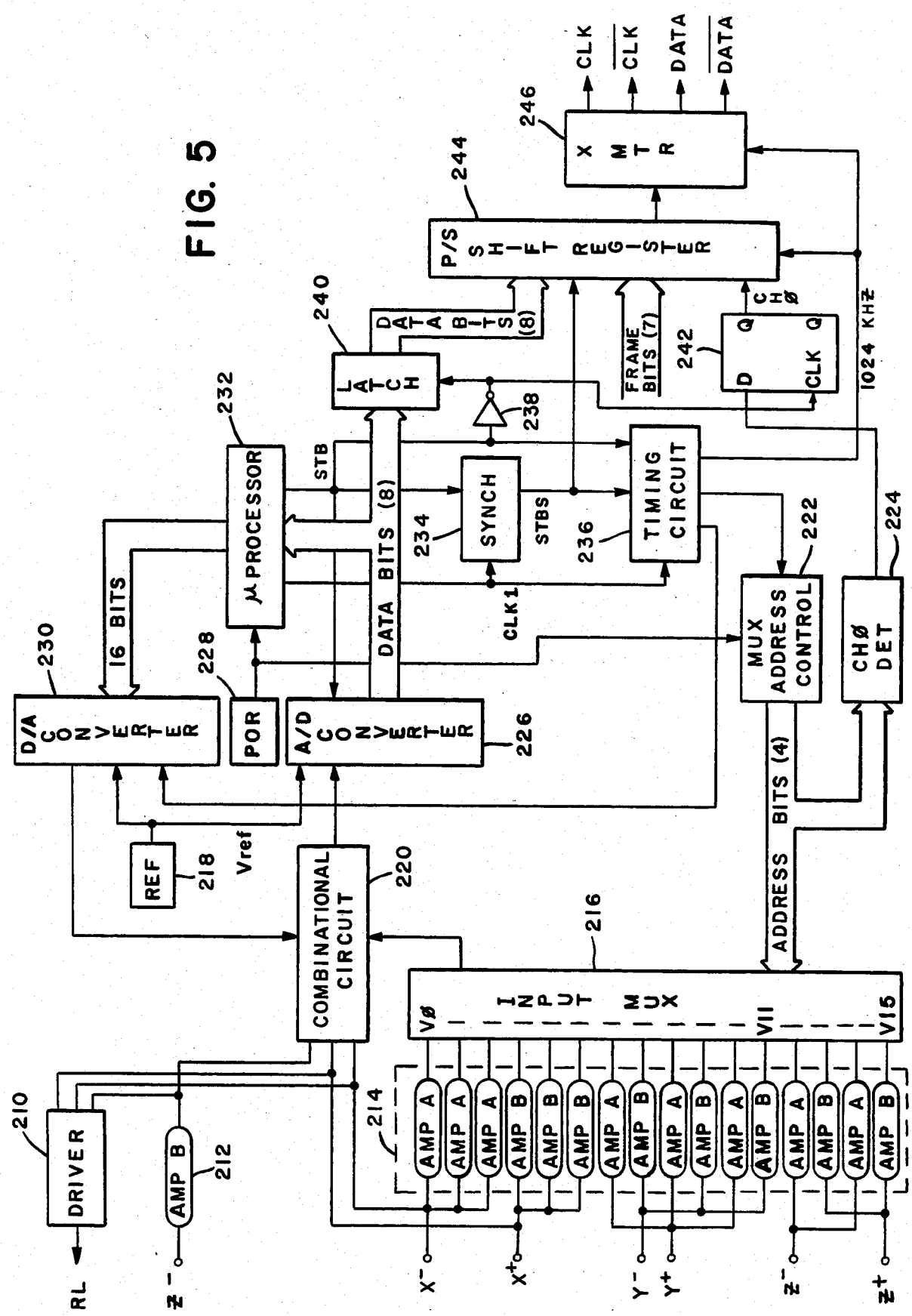
FIG. 5 is a hardware block diagram of the signal conditioning means illustrated in FIG. 2.
Figure 6:
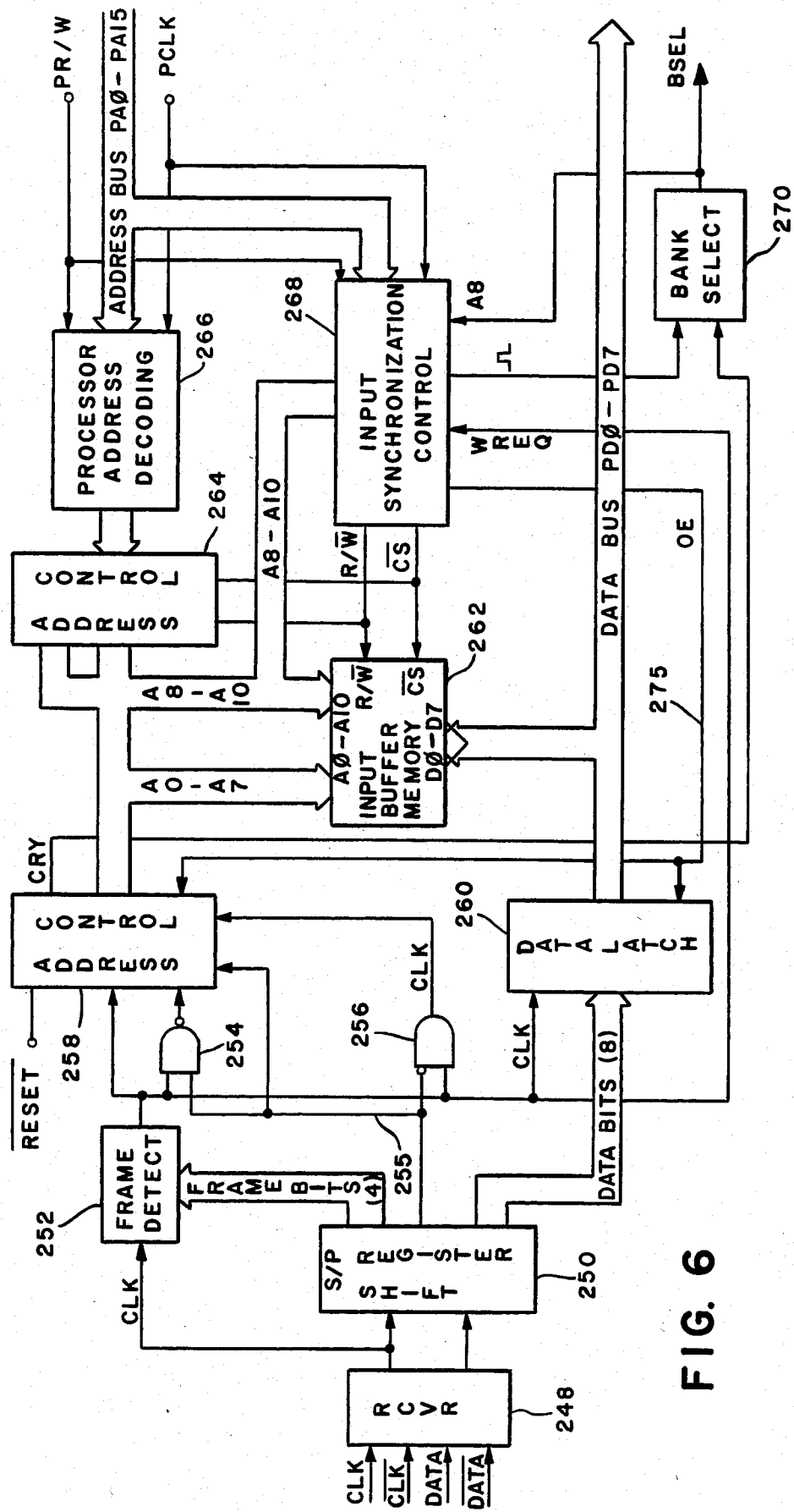
FIGS. 6 and 7 are hardware block diagrams of the preprocessor illustrated in FIG. 2.
Figure 7:
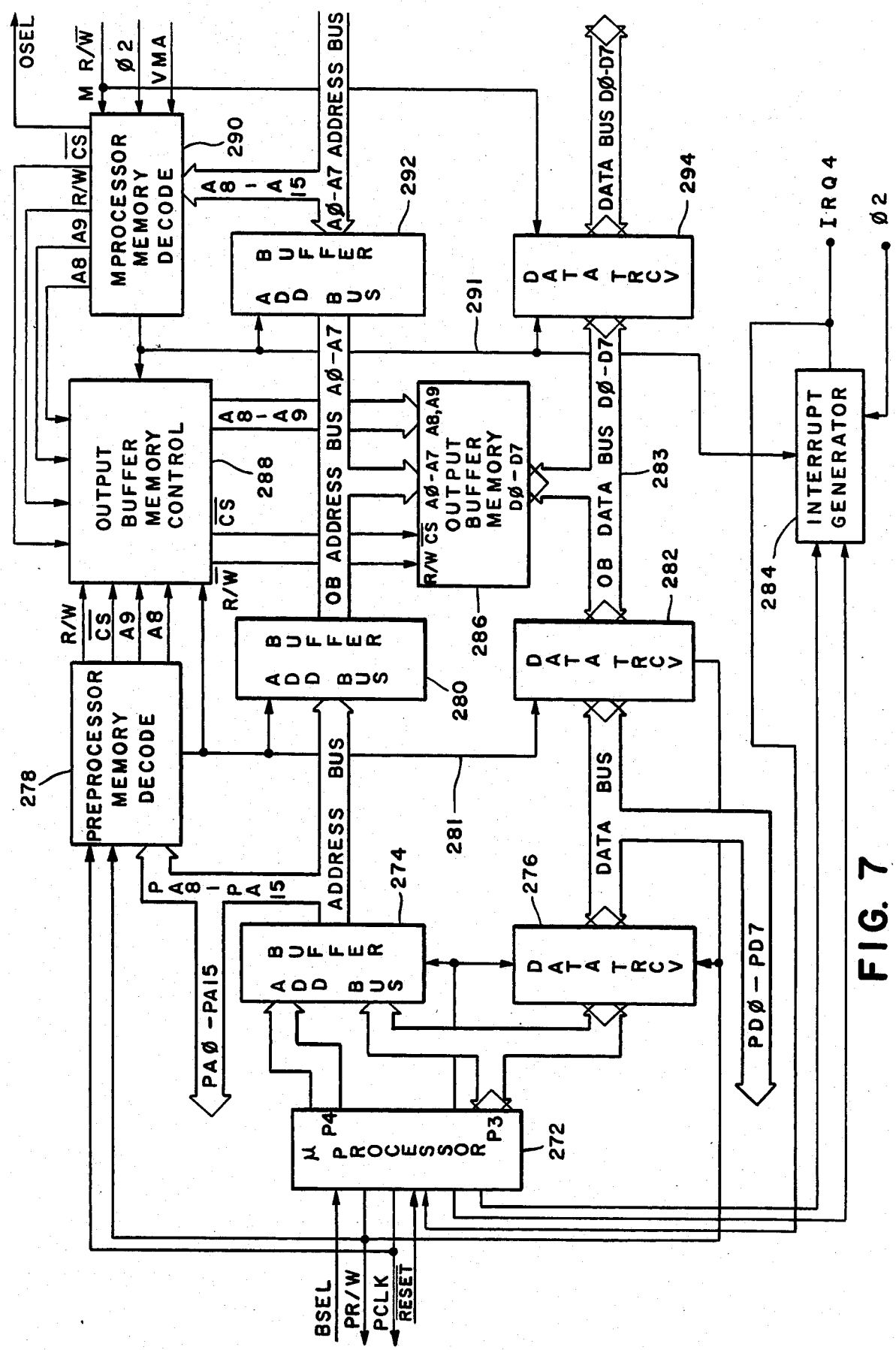
Figure 8:
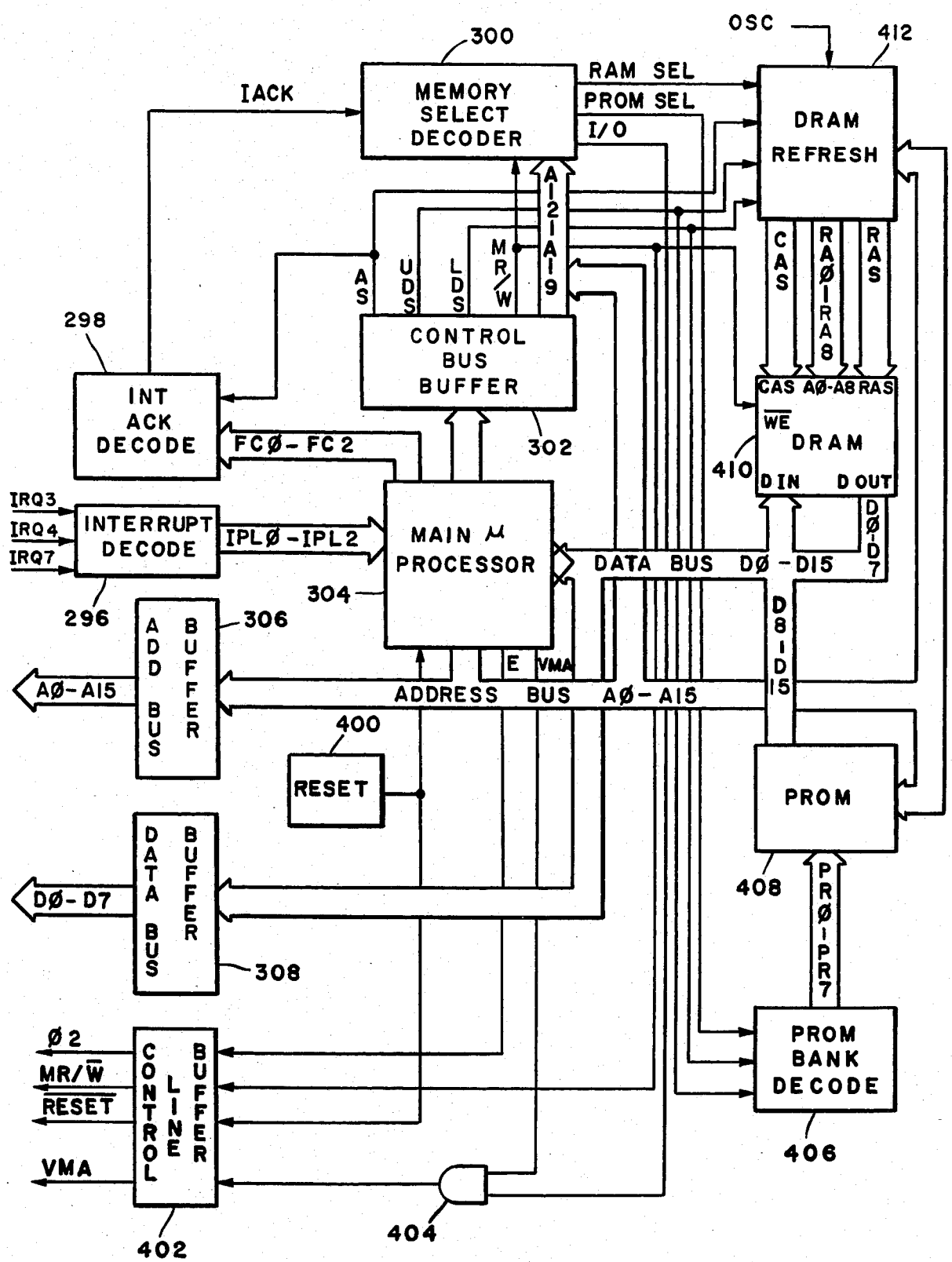
FIG. 8 is a hardware block diagram of the processor illustrated in FIG. 2.
Figure 9:
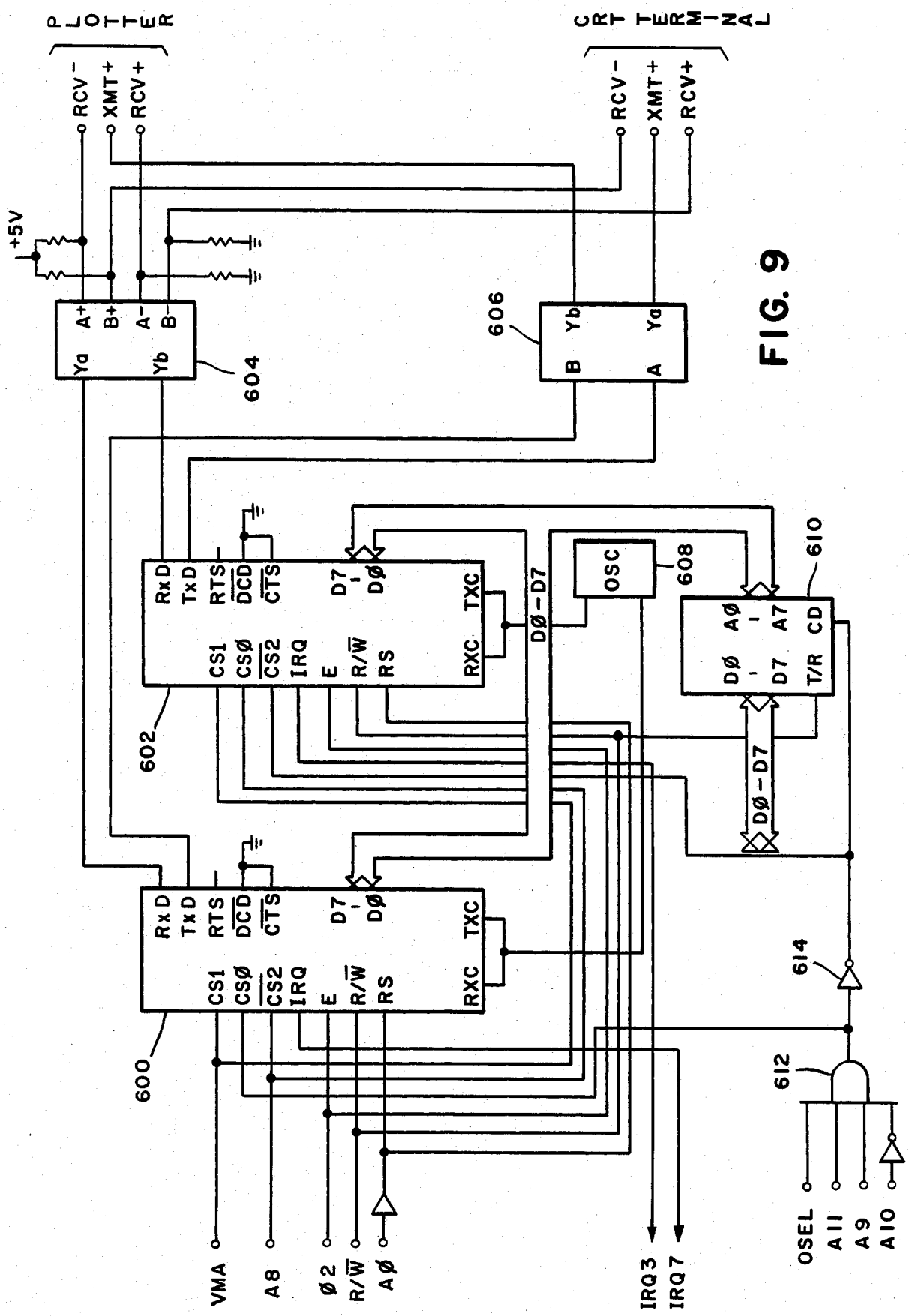
FIG. 9 is a hardware block diagram of the communication links between the plotter, CRT terminal and processor illustrated in FIG. 2.

With respect now to FIGS. 5-9 there is illustrated detailed electrical block diagrams of the circuitry comprising the signal conditioning means 200, the preprocessor means 202, and the main processor means 206. FIG. 5 is a block diagram of the signal conditioning means 200, FIGS. 6 and 7 are block diagrams of the preprocessor means 202, FIG. 8 is a block diagram of the main processor 206, and FIG. 9 is a block diagram of the communication links between the main processor 206, the CRT terminal 208 and the plotter 204.

Figure 5A:
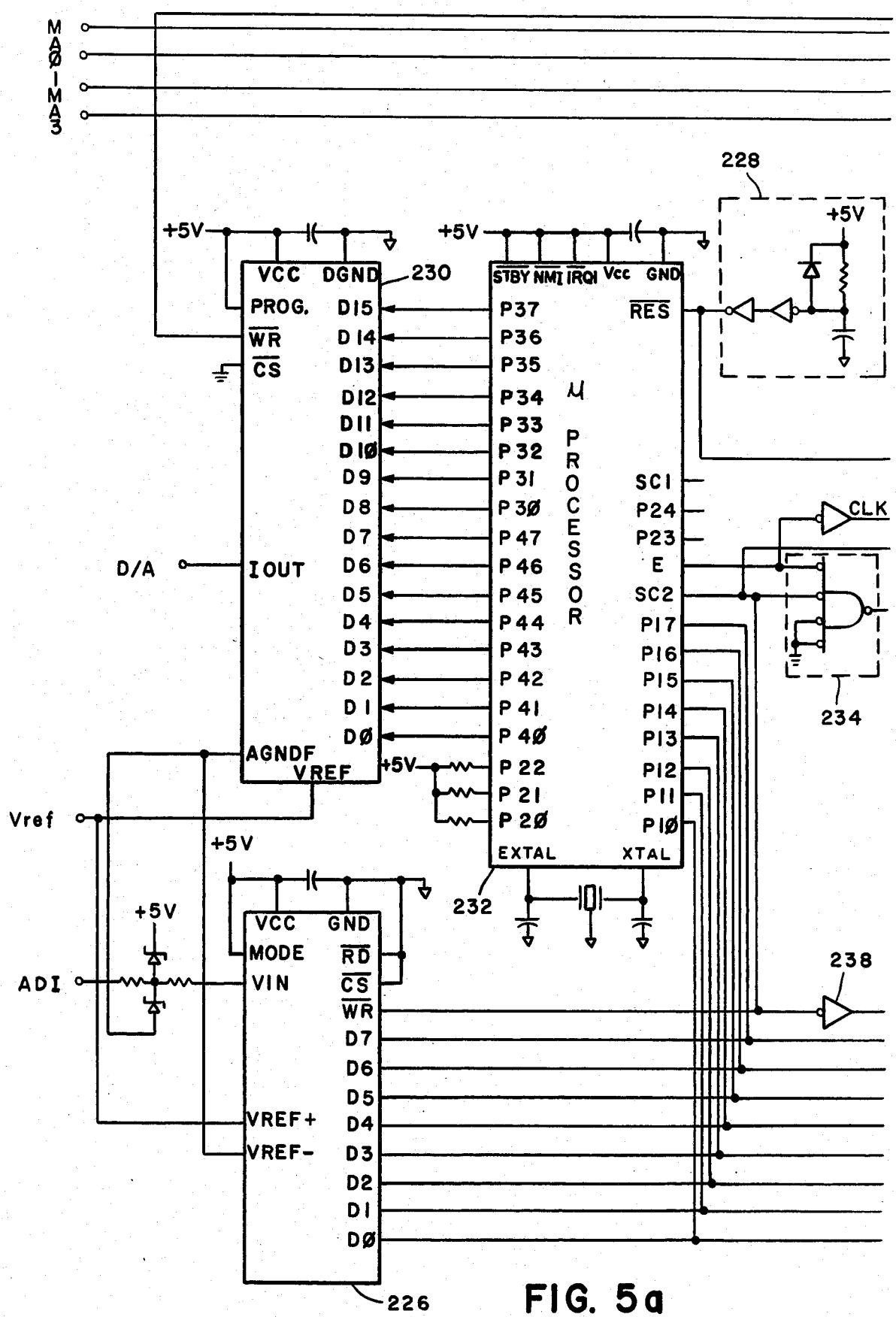
Figure 5B:
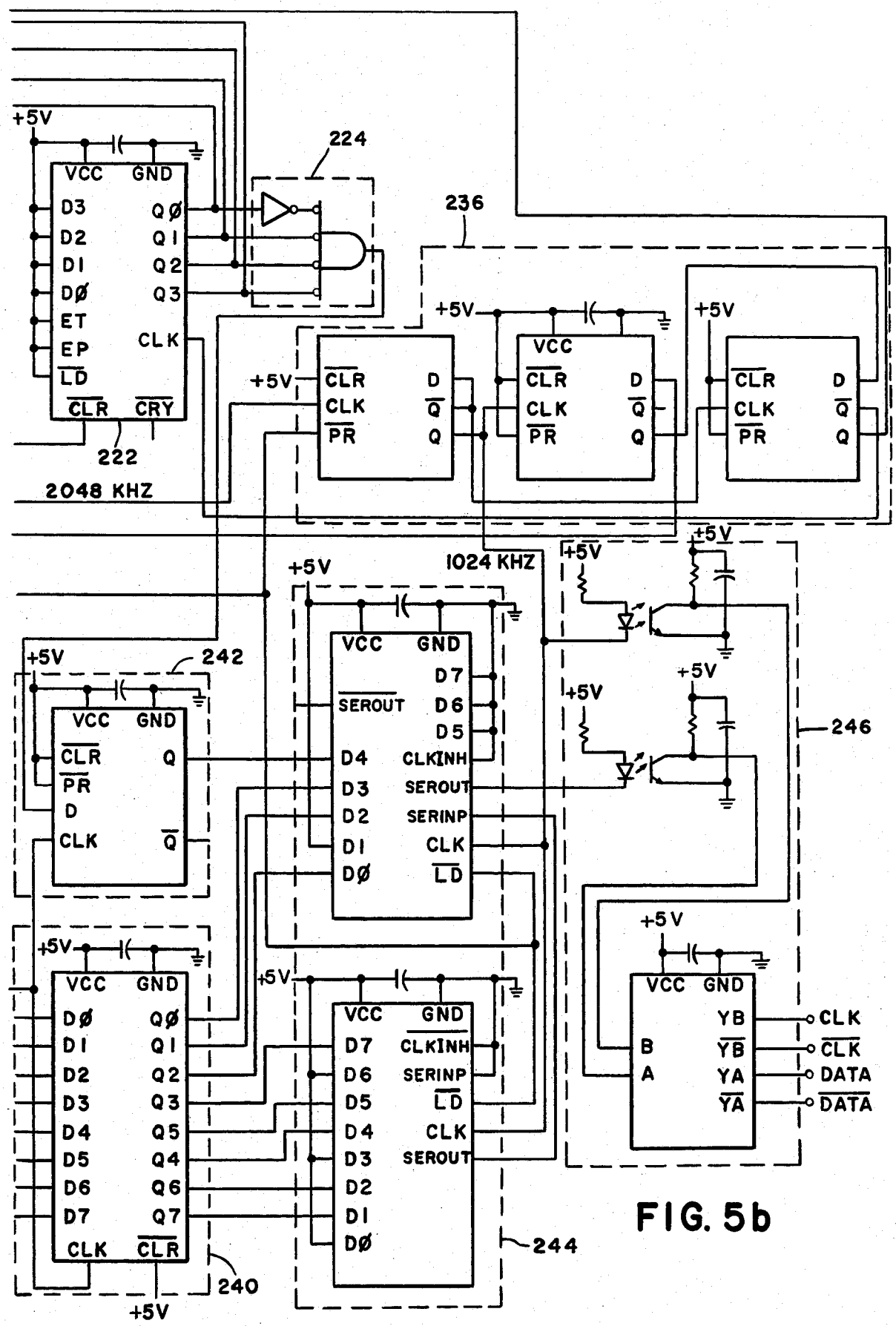
Figure 6A:
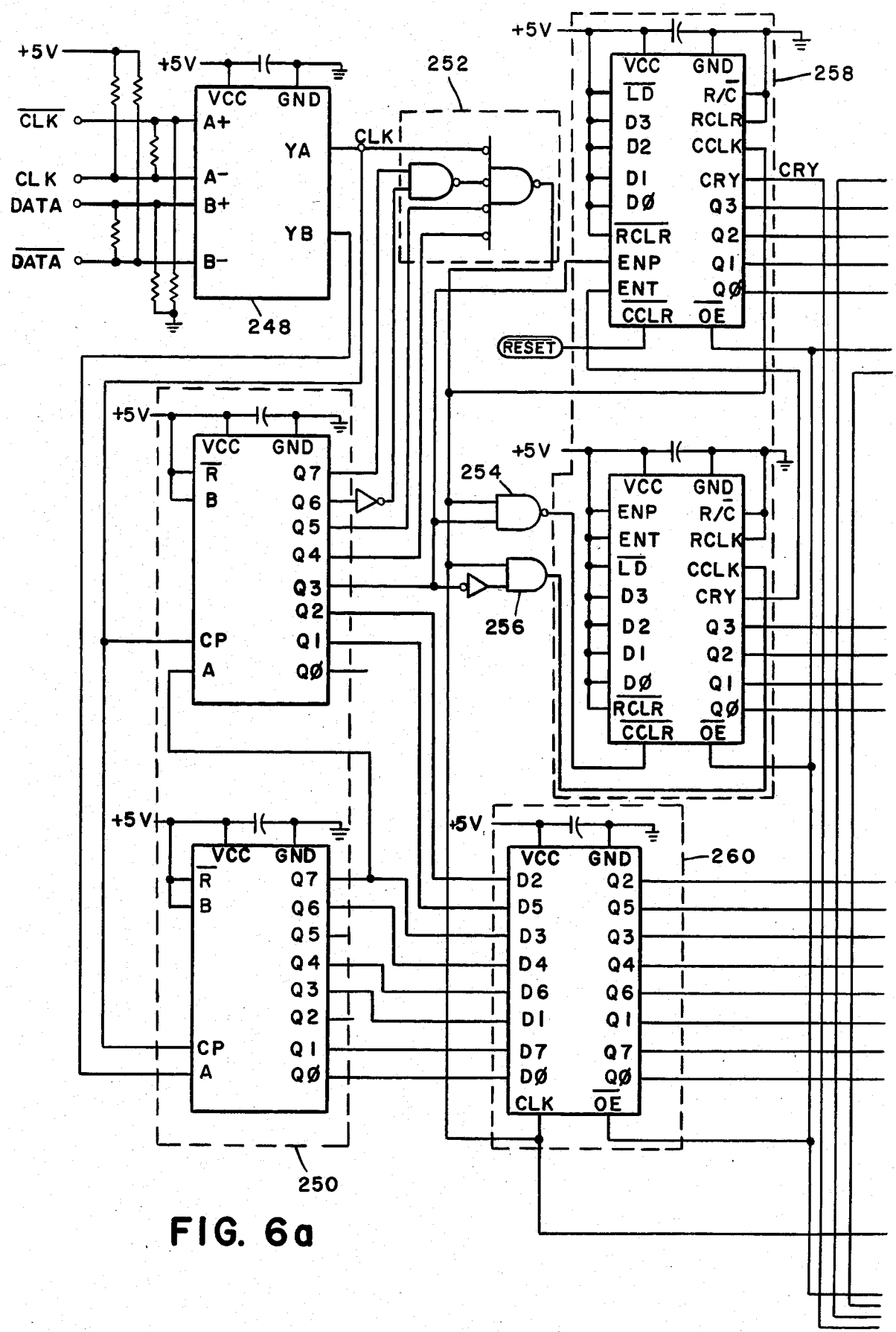
FIGS. 6a-6b are detailed schematic diagrams of the various elements illustrated in FIG. 6.
Figure 6B:
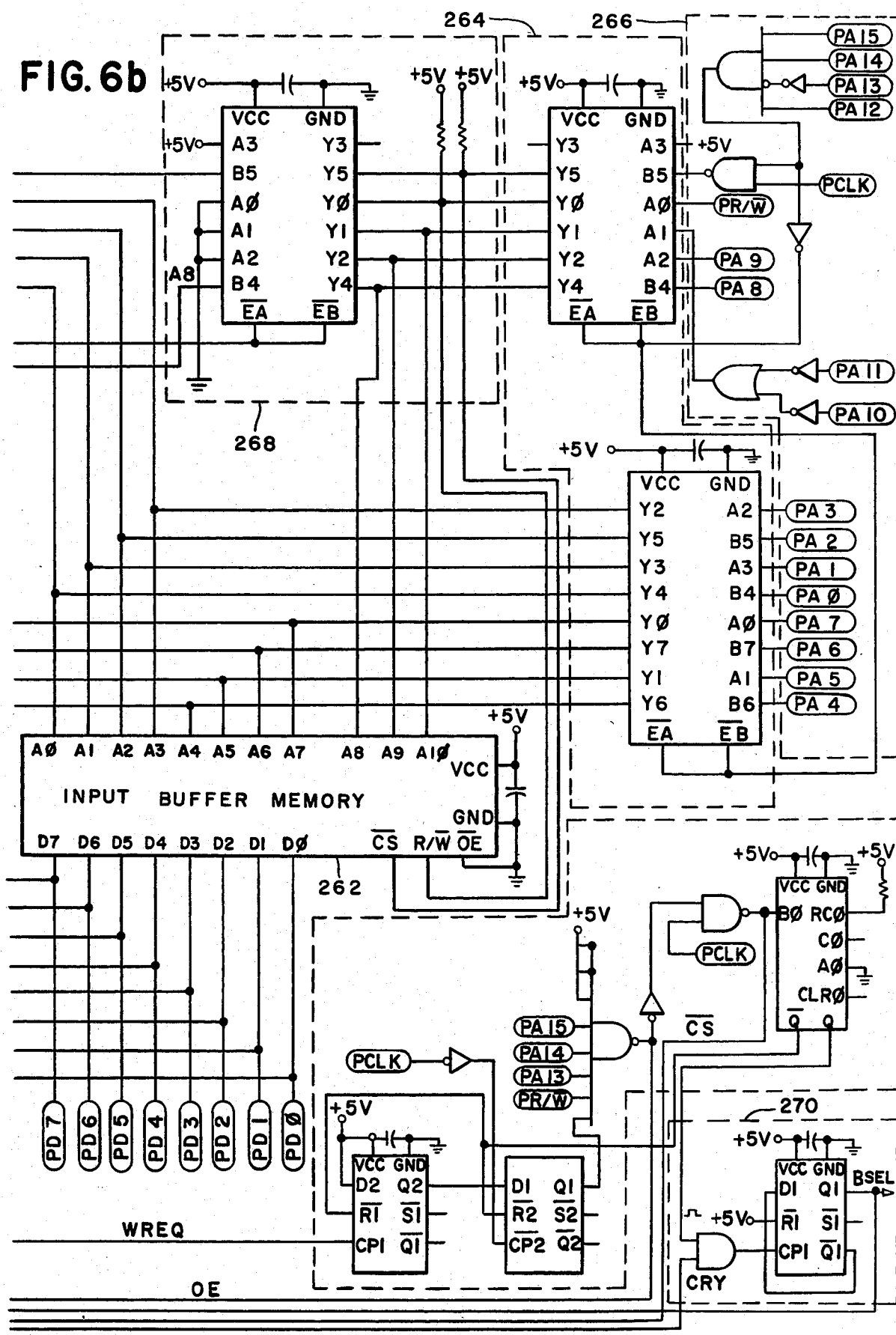
Figure 7A:
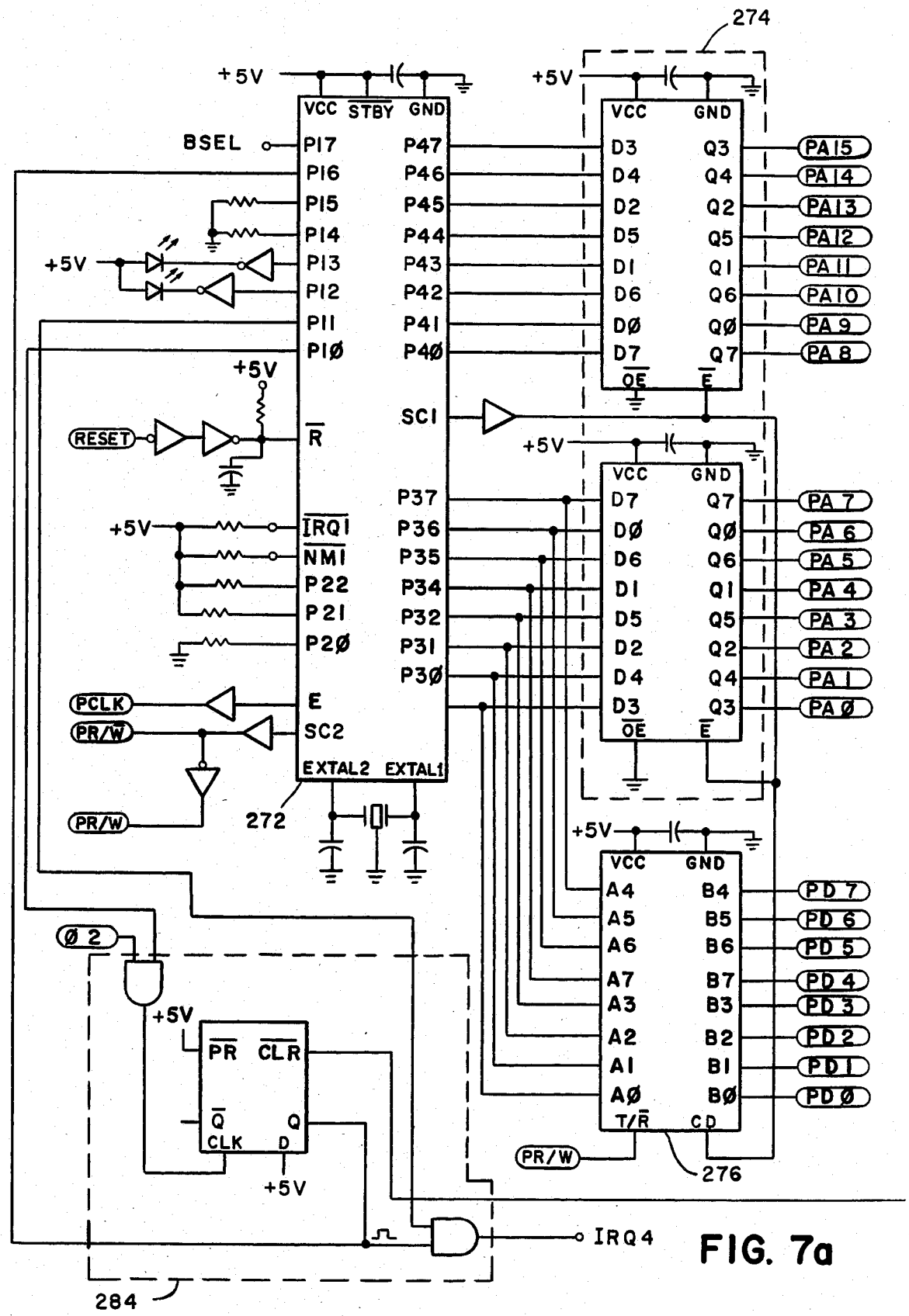
FIGS. 7a-7b are detailed electrical schematic diagrams of various components of the preprocessor illustrated in FIG. 7.
Figure 7B:
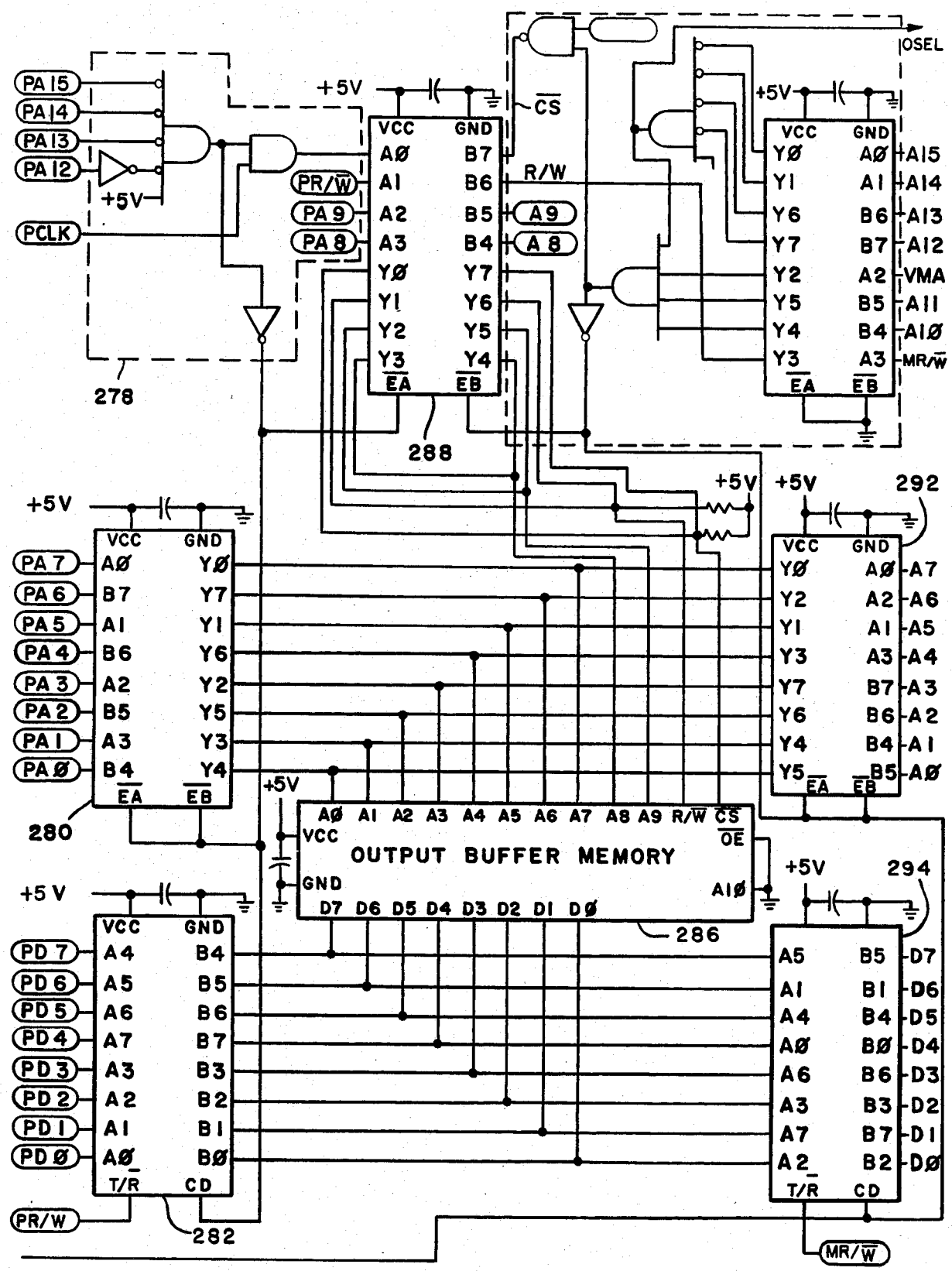

Detailed circuits for the blocks of FIG. 5 are shown in FIGS. 5a-5b, detailed circuits for the blocks of FIG. 6 are shown in FIGS. 6a, 6b, and detailed circuits for the blocks of FIG. 7 are shown in FIGS. 7a, 7b.

If attention is now directed to FIG. 5 a more detailed description of the signal conditioning means 200 will be provided. The signal conditioning means comprises basically an analog/digital converter which converts information supplied on channel leads X−, X+, Y−, Y+, Z−, and Z+ into digital data samples which can be output in serial format via transmitter 246 to the preprocessor 202. Each of the signal leads is connected to a set of multiple amplifiers 214 which form input channels of an input multiplexer 216. The X−, X+, Y−, Y+ leads are amplified by three amplifiers and are each input to three separate channels of the input multiplexer 216. The Z− and Z+ leads are connected to two amplifiers and are input to two channels of the input multiplexer 216. The multiple connections to the input channels of the multiplexer are to provide a parallel lead combination function as will be more fully explained hereinafter. It is seen that the input multiplexer receives 16 separate analog signals and outputs one of them to a combinational circuit 220 depending on a 4 bit channel address from a multiplexer address control 222.

As is conventional, the X−, X+ leads are designated references and are separately input to a combinational circuit 220. Additionally, a separate input for the Z− lead is input via an amplifier 212 to the combinational circuit 220. The X−, X+ and the 2-lead signals are additionally fed back through a driver circuit 210 to the right leg electrode RL.

This configuration of terminal connections to a patient is termed a "driven right leg" and is well known in the art. By differencing the opposite polarity signals of the same lead, for the example X+, X−, a waveform of a axis of the cardiac potential is obtained. Thus, signals for the X, Y and Z axes are available from these connections which can be translated into three perpendicular planes.

The terminal signals for leads X+, X−, and 2− are combined in the combinational circuit 220 to provide a reference voltage for each of the terminal leads input from the multiplexer 216. The reference output from the combination is subtracted from an input junction of the combinational circuit to provide a ECG waveform with a common baseline. The output of the combinational circuit is an analog signal which is input to the conversion input I of an analog to digital converter 226.

Additionally subtracted from the input channel signal in the input junction of the combinational circuit 220 is a feedback signal from a digital to analog converter 230. The feedback signal is the previous value of the analog signal for the particular channel input. The previous value is output in digital form from the memory of a microprocessor 232 where it was stored to the digital to analog converter 230 for conversion and thereafter output to the combinational circuit 220. Therefore, it is the analog difference between the previous value of the channel amplitude and the present value of the channel amplitude modified by the Wilson terminal reference signal that is converted by the analog to digital converter 226. In the digital context this difference is equivalent to taking the derivative of the input signal. A reference voltage generation circuit 218 provides an identical conversion reference voltage for each of the converters 226 and 230 such that the ground levels of each are identical. This common reference level reduces any ground level shift between the devices during the conversions. The output of the analog to digital converter 226, which is one 8 bit data byte, is input to the microprocessor 232 and to a latch 240 for storage purposes.

The conversion process is under program control of the microprocessor 232 which communicates with the D/A converter 230, the A/D converter 236, and the latch 240. The program control of the microprocessor 232 generates a clock signal CLK1 which is input to a synchronization circuit 234 and a timing circuit 236. A control strobe signal STB is further generated by the processor under program control and is input to the A/D converter 226, the synchronization circuit 234 and the latch 240 via an inverter 238. The synchronization control 234 generates a control signal STBS from the strobe STB which is synchronized with the clock signal CLK1. The control signal STBS is then gated by the timing circuit 236 to the D/A converter 230 and the multiplexer address control 222 to cause a conversion and to cause a change in the channel address, respectively.

In general operation, for an A/D conversion to take place, the microprocessor 232 outputs the previous value for a channel to be sampled in a 16 bit format and advances the address multiplexer control 222 to select that channel address. The value of the input signal of that channel is then differenced with the previous value in the combinational circuit 220 and converted to a digital number by the A/D converter 226. Thereafter, the data are latched into the latch 240 for transmission to the preprocessor 202.

Resolution of the converted signal is 16 bits because of the digital to analog converter 230. This is accomplished by the accurate conversion of the previously stored value into an analog value before the difference is taken. Because only the difference of the two values is transmitted, the A/D converter 226 with only 8 bits can be used without loss of the higher resolution. This feature permits a high resolution sample of a waveform to be taken while minimizing the number of data bits transmitted for each sample. The feature thus saves bit length for the memories needed to store the samples and allows a higher data transmission rate.

Included in the timing circuit is a means for generating a high speed clock signal at 1024 kHz and outputting it to a parallel to serial shift register 244 and a transmitter 246. After digital data have been stored in the latch 240, the parallel to serial shift register 244 will take the data upon receiving the STBS signal and serially shift them out to the transmitter 246. Interlaced with the data at the inputs to the shift register 244 are seven framing bits which provide a unique pattern in the serial data output. The framming bits are provided by setting certain inputs of the register high or low depending upon the pattern desired.

Additionally, included in the serial data because of its input to the shift register is an interleaved channel zero signal CHO. The CHO signal is generated by a D type flip-flop 242 when it receives a detection signal from a channel zero detection circuit 224. The channel zero detection circuit 224 monitors the four address bits of the multiplexer address control 222 and determines when channel 0 of the multiplexer has been selected. The output of the channel zero detection circuit is a pulse which arrives at the D input of the flip-flop 242 and is clocked out of the Q output of the device by the strobe signal STB via the inverter 238.

The combination of the unique framing bits, the eight data bits representing one difference sample, and the channel zero detection bit are input in parallel to the shift register 244 upon the strobe signal STBS and then clocked out with the 1024 kHz clock to the transmitter 246 in a serial fashion. The identical clock signal is supplied to the transmitter 246 which then transmits the data in serial format and its inverse along with the clock signal and its inverse for synchronization.

The strobe signal is presented every 16 microseconds and therefore causes a conversion for each of the channels at this interval. A full cycle of all sixteen channels requires 250 microseconds for a sampling rate of approximately 4000 samples/sec/lead. The microprocessor 232 runs this input circuitry with a software program looping through this operation which is synchronous to the other circuitry. The software loop is started by a power on reset signal from circuit 228 which also initializes the multiplexer address control to channel 0.

With respect now to FIGS. 6 and 7 the block diagram of the preprocessor 202 is shown to advantage as receiving the clock and data output from the signal conditioning means 200 at a receiver 248. The data and clock signals are then transferred to a serial to parallel shift register 250 from the output of the receiver 248 under the control of the clock signal CLK. Sixteen bits of data are synchronously clocked into the shift register 250 from the signal conditioning means including the eight data bits, the seven framing bits, and the channel 0 detect bit. Four of the framing bits are used by a frame detector circuit 252 in conjunction with the clock signal CLK to provide a clock signal CLK for inputting the data bytes to an input buffer memory 262.

If a correct framing byte sequence is not detected by the circuit 252, the clock signal CLK1 will be inhibited and the bad data discarded from the shift register 250. Inaccurate data never are stored in the input buffer memory 262 because of data errors on the transmission from the signal conditioning means 200 to the preprocessor means 202. Assuming a correct framing character has been detected, the data bytes are clocked into a data latch 260 for input to the buffer memory 262. The clock signal also increments an address control 258 which has address lines A0-A7 connected to the address input lines of the input buffer memory 262.

However, the data are not immediately loaded into the input buffer memoran 262 until an output enable control line 275 is provided with an enabling signal from an input synchronization control 268. The output enable signal on the control line 275 allows storage of the incoming data when the microprocessor 272 of the preprocessor is not accessing the input buffer memory 262. Therefore, the enabling signal on that line indicates that the microprocessor is busy doing other tasks and the particular data word in the latch 260 may be stored.

This operation provides a synchronization for loading the input buffer memory 262 where a data word is input to the data latch 260 upon frame detection of the unique frame character and then stored until the input buffer memory 262 is accessable. The cycle continues with incoming data enabling the clock to increase the count in the address control 258 from zero to an address of 256.

The channel 0 detection bit is output from a shift register line 255 to two AND gates 254 and 256 in order to be combined with the frame character enabled clock CLK1. In gate 256, the input of the channel 0 detect bit is negated and therefore enables the clock for all channels except channel 0. Gate 256 therefore provides another clocking signal to the address control 258 for channels 1 through 15. Upon the occurrence of the channel zero detection bit and the clock signal CLK1, the output of gate 254 makes a transition to a low level to reset the address control 258. This provides a synchronization of addresses whereby the channel 0 input data are always initiated from a memory address of 0. The address control 258 is further reset by the control signal RESET from the main processor 206 as will be more fully explained hereinafter.

The address control circuit 258 loads the first 256 positions in the input buffer memory 262 with information received from the signal conditioning means 200. When the address control 258 overflows it generates a carry signal CRY to a bank select circuit 270 to indicate that the first 256 memory locations are filled. The bank select circuit 270 thereafter generates a control signal A8 to the input synchronization control 268, causing it to generate an address signal on address line A8 to the input buffer memory 262. This address control line A8 will thereafter enable the next higher 256 locations in the input buffer memory 262 to provide another block of input memory to the input address control circuitry 258. The bank select circuit 270 alternates the control signal A8 such that the input address control circuitry 258 fills one 256 sample block and then the other by alternating between the two. A bank select signal BSEL is generated and applied to the microprocessor 272 of the preprocessor 202 to indicate which bank is being filled by the address control circuitry 258.

The bank opposite that being filled with the input data may then be read by the microprocessor 272 of the preprocessor via the data bus having data lines PD0–PD7. Addresses from which the memory is read are provided by signals from a processor address decoding circuit 266. The address decoding signals are generated by the control lines and address bus PA0–PA15 of the microprocessor 272 of the preprocessor 202. A read/write control line PW/R is provided to indicate when the input buffer memory 262 should be read; address lines from the address bus PA0–PA15 are provided to indicate addresses in the input buffer memory 262 which are to be read; and the synchronization of the reading is provided by the preprocessor clock signal PCLK. The actual timing of the reading of the input buffer memory by the microprocessor 272 is provided by the input synchronization control 268 generating the signals R/W and CS which select the input buffer memory 262 for reading and enabling the buffer memory, respectively.

With reference specifically to FIG. 7 the microprocessor 272 receives the data from the input buffer memory via the data bus through a data transceiver 276 at its port, P3. Port, P3 is a bidirectional port and the data transceiver 276 is enabled by the read/write control line PR/W of the microprocessor 272.

Once the data stored in one of the input buffer memory blocks are brought into the microprocessor 272, an internal software program operates on the data to cause preprocessing functions which are independent of the data content. After the data have been preprocessed, the data samples are stored in an output buffer memory 286. Along with the data samples, other preprocessed data are placed in the output buffer memory 286. The other data include the bandpass filter outputs, the maximum difference detection, a lead fail word, and a clock fail word.

The output buffer memory 286 receives the data from the microprocessor 272 via a data transceiver 276, the data bus PD0–P07, a data transceiver 282 and the output buffer memory data bus 283. Addresses for the data to be stored in the output buffer memory 286 are provided to the output buffer memory address bus via an address bus buffer 274, the microprocessor address bus PA0–PA15, and an address bus buffer 280. The addresses are provided by a software run routine which loads the address buffer 274 via ports P3 and P4 of the microprocessor 272.

The reading and writing of the data in the output memory buffer 286 are under the control of an output buffer memory control 288 which enables the read/write line R/W and the chip select control line $\overline{CS}$ of the memory 286. The output buffer memory control 288 is under the dual regulation of the microprocessor 272 of the preprocessor 202 and a microprocessor 304 of the main processor 206. For access by the preprocessor 202, the output buffer memory control 288 receives the control signals R/W, $\overline{CS}$, A8 and A9 from a preprocessor memory decoding circuit 278. These signals are synthesized from the microprocessor address lines PA8–PA15 of the address bus, the microprocessor clock PCLK, and the read write control signal PR/W. When the microprocessor 272 requests access to the output buffer memory 286, it also raises an enable line 281 which enables the data transceiver 282, the address bus buffer 280, and the output buffer memory control 288. This structure provides a convenient operation for storing the data after they have been preprocessed. The storage of the data is at the rate of 1000 samples/sec/lead.

The output buffer memory 286 may also be read from or written to by the microprocessor 304 (FIG. 8) of the main processor 206. The output buffer memory control 288 also receives control signals R/W, $\overline{CS}$, A8, A9 to generate similar control signals to the memory 286 from decoded control lines of the microprocessor 304. A main processor memory decoding circuit 290 generates these signals from the microprocessor control lines MR/W $\phi$02 of the main microprocessor clock, and a virtual memory access control line VMA. The addresses for the output buffer memory 286 are provided via the address bus through a bus buffer 292. Data are transported through a data transceiver 294 between the output buffer data bus and the data bus of the microprocessor 304. The read/write control line $\overline{MR/W}$ of the microprocessor 304 sets the direction of the data transceiver 294, and an enabling signal on line 291 from the main processor memory decoding circuit 290 enables the address bus buffer 292 and the data transceiver 294.

To maintain synchronization between the microprocessor 272 of the preprocessor 202 and the microprocessor 304 of the main processor 206, an interrupt generator 284 is provided to generate an interrupt signal via interrupt line IRQ4 of the microprocessor 304. The interrupt is generated by software generated signals from the microprocessor 272 in phase with the 02 output clock signal of the microprocessor 304. The interrupt generator 284 clears the IRQ4 signal upon receipt of the enabling signal on line 291. The IRQ4 signal is further read by the microprocessor 272 to determine whether or not the microprocessor 304 of the main processor has cleared it.

In operation the microprocessor 272 maintains synchronization between the main processor 206 and the signal conditioning means 200 by unloading the input memory buffer at a 4000 sample/sec/lead rate, preprocessing the data, and loading the output memory buffer at a 1000 sample/sec/lead rate. After the microprocessor 272 has loaded the output buffer 286 with the data samples and other preprocessed data, it will generate an interrupt request via the interrupt generator 284.

The interrupt is generated periodically at four millisecond intervals to provide a time base between the two processors. Once the interrupt has been recognized, the microprocessor 304 of the main processor 206 knows that data are ready to be input and thereafter can access the output buffer memory 286 until the next four millisecond cycle is initiated. Once the processor 304 starts to access the output buffer memory 286 the enabling signal on the line 291 from the main processor decoding circuit 290 clears the interrupt request. The acknowledgement of the interrupt is recognized via the feedback line at microprocessor 272.

With respect now to FIG. 8 there is shown the hardware block diagram for the main processor 206 and associated circuitry. The main processor 206 is a microprocessor based controller which receives and transmits data from the preprocessor 202, the plotter 204, and the CRT terminal 208. The microprocessor 304 preferably used in the implementation is identified as an MC 68000 processor commercially available from the Motorola Corporation of Schaumberg, Ill. The control lines, data lines, and address lines nomenclature used herein will be that which is identified in the manufacturers user's manual for this device.

The main processor 206 includes the microprocessor 304 which has an associated dynamic random access memory DRAM 410 and programmable read only memory PROM 408. A software control program is stored in the PROM 408 to provide system control and processing routines. To access the PROM 408 for instructions the system generates a memory select signal PROMSEL to a PROM bank decoder circuit 406. From this signal and control line signals UDS and LDS via a control bus buffer 302, an area in the PROM is enabled by address select lines PR0–PR7. The address select lines PR0–PR7 enable these areas in the PROM 408 such that the address location accessed by the address bus lines A0–A15 from the microprocessor 304 can be read. Instructions from the PROM 408 are output to the microprocessor 304 on the data bus via data lines D8–D15.

The dynamic random access memory DRAM 410 communicates with the microprocessor 304 via the data bus lines D0–D7 wherein each of these data lines is connected in parallel with both the DIN and DOUT terminals of the device. A DRAM refresh circuit 412 supplies the DRAM 410 with a plurality of column address strobe signals CAS and row address strobe signals RAS. In addition a plurality of enable signals RA0–RA8 to select blocks of the DRAM 410 are generated from the refresh circuit 412. In combination with the address bus lines A0–A15 and the read write control line MR/W, the DRAM 410 will be able to determine which memory address location is selected and whether the desired memory cycle is a read or a write operation. Address control for the DRAM refresh circuit 412 is generated from the microprocessor control line signals UDS, LDS, AS and the random access memory select signal RAMSEL. An additional input to the refresh circuit 412 is an oscillator signal OSC which allows the circuit to refresh the memory location between read and write cycles by cycling the column and row addresses, as is conventional.

The memory select signals including RAMSEL and PROMSEL are generated by a memory select decoder circuit 300 from the address lines A12–A15 of the microprocessor address bus and address lines A17–A19 of the control bus via control bus buffer 302. Additionally the read/write line MR/W is decoded to form the memory select signals in the circuit 300. The memory select decoder 300 also produces a memory select signal I/O for input and output from the peripheral devices.

The memory select decoder circuit 300 determines which of the memory areas of the memory space, i.e., DRAM, PROM, or I/O that the microprocessor 304 is accessing. The memory select decoder circuit 300 does this by decoding the address lines to determine which area in the memory space a particular memory device or I/O device has been assigned. For I/O devices the memory select decoder 300 also receives the interrupt acknowledge signal IAK from an interrupt acknowledge decoder circuit 298. The interrupt acknowledge decoder circuit 298 receives a three bit word on interrupt lines FC0–FC2 from the microprocessor 304 and the control line AS to determine that the microprocessor 304 has answered an interrupt code.

The microprocessor 304 communicates with the preprocessor 302 by accessing the output buffer memory 286 with the address lines A0–A15 via address bus buffer 306 and data bus lines D0–D7 via a data bus buffer 308.

Control lines from the microprocessor 304 used to access the output buffer memory 286 via a control line buffer 402 additionally include the phase two clock signal $\phi 2$, the read write control line MR/W, the reset control line RESET, and the virtual memory access control line VMA. The $\phi 2$ signal is generated from the E clock output of the microprocessor 304 and is an internally generated clock signal phased to the processor cycle. The VMA signal from the microprocessor 304 indicates that the memory that is being accessed is not in the standard memory space and in combination with the I/O signal is combined in an ANP gate 404 to become the VMA signal to the output buffer memory 286. The read write control line MR/W is generated in a normal manner via the control bus buffer 302 from a control line of the microprocessor 304. The reset signal RESET is generated by a microprocessor reset circuit 400 which additionally supplies the signal to the microprocessor 304 during power ups and for recovery of other special conditions.

The microprocessor 272 of the preprocessor, the CRT terminal 208, and plotter 204 communicate with the microprocessor 304 of the main processor via interrupt request lines IRQ4, IRQ3, and IRQ7 which are decoded in an interrupt decoding circuit 296. The interrupt decoding circuit 296 decodes the request into a byte code on interrupt signal lines IPL0-IPL2 which are input to the microprocessor 304. Interrupt handling routines thereafter control clearing of the interrupts and prioritizing the I/O from these peripheral devices.

This system configuration shown in FIG. 8 is a generally conventional signal board computer system for a microprocessor control such as the MC 68000. The labeled microprocessor control, address, and data lines are those which are standardly used in the art to designate the functions described. The memory and selection circuitry are commonly known to those skilled in the art and can be expanded or contracted depending upon needed memory size. Since FIG. 8 represents a standard configuration for a MC 68000 microprocessor control, additional detailed description of the circuitry illustrated in this drawing need not and will not be provided.

The hardware block diagram for the communication links between the plotter 204, the CRT terminal 208, and the microprocessor 304 is shown to advantage in FIG. 9. Data from the microprocessor 304 are transmitted via a transceiver chip 610 to a pair of receiver-transmitter controller chips 600 and 602 respectively. The D0-D7 terminals of the chips are both inputs and outputs where the direction of the transceiver chip 610 controls the inflow and outflow of data between the plotter 204, CRT terminal 208, and microprocessor 304. Each controller chip has a receive terminal RXD and a transmit terminal TXD by which serial data are input to and output from a buffer on the chip. By controlling the other inputs of the device parallel data, one byte at a time, can be input to and output from the transceiver chip 610.

The controller chips 600 and 602 run at a frequency controlled by the output of an oscillator 608 connected to their RXC and TXC terminals. The oscillator can generate any convenient frequency which could be different for the recieve and transmit channels of each device or different for the plotter 204 and CRT terminal 208. In the illustrated embodiment, however, each device is run at the same frequency for both receive and transmit channels, preferably at 9600 baud.

The control chip 600, for example, is dedicated to the plotter 204 and is connected at its transmit terminal TXD to the B input of a transmitter chip 606 which drives the transmit terminal XMT+ of the plotter. The RXD or receive terminal of the control chip 600 is connected to the Ya output of a receiver 604 which receives serialized data from the RCV−, RCV+ outputs of the plotter 204 at the A+, A− input terminals of the receiver.

Similarly, the transmit terminal TXD of the controller chip 602 is connected to the input A of the transmitter 606, which produces a serialized data output Ya to the XMT+ terminal of the CRT device. The receiver terminal RXD of the controller device 602 is connected to the Yb output of the receiver 604, which accepts serial data from the CRT terminal 208 outputs RCV−, RCV+ at its input terminal B+ and B−. The interface between the plotter 204, CRT terminal 208, and the receiver 604 and transmitter 606 is a conventional R232C communication protocol. The receiver 604 and transmitter 606 perform a buffering and conditioning function for the serialized data and are able to transmit and receive characters or data bytes via the communication links to the plotter 204 and CRT terminal 208.

Control of the I/O for these communication links is provided by the address lines A0, A8-A11 and a coded select signal line OSEL. Further control lines from the microprocessor 304 are the virtual memory access signal VMA, the phase two clock signal 02, and the read/write signal R/$\overline{W}$. The communication links request information transfer with the interrupt requests IRQ3 and IRQ7 to the microprocessor.

The signal VMA notifies nonstandard memory space devices that they are being addressed and thus the VMA signal enables the controller chips 600 and 602 by being applied to their CS1 inputs. The particular chip selected, which determines whether the plotter 204 or CRT terminal 208 will be communicating with the main processor 304, is determined by the address output from the microprocessor 304 on the respective address lines and as decoded by an AND gate 612. The decoded addresses are applied to the CS0, $\overline{CS2}$, and RS inputs of the devices 600 and 602. The inversion of the output of the AND gate 612 by an inverter 614 prior to its transmission to the $\overline{CS2}$ input of the controller device 602 provides address discrimination between the two control chips. The read/write signal R/$\overline{W}$ from the microprocessor is connected to the read/write terminal R/$\overline{W}$ of each control chip 600, 602 to determine the direction of data transfer and further to determine the direction of the transceiver chip 610. The E inputs of the control chips 600, 602 are connected to the phase two clock $\phi$2 to provide timing for the data transfers.

In operation both control chips 600, 602 work identically in that for a read operation serial data are input from the receiver 604 to the RXD input where they are placed in a buffer. The buffer is 8 bits in length and has parallel outputs to the D0-D7 terminals of the chip. Once the data have been buffered, the particular controller chip will provide an interrupt request from its IRQ terminal to notify the main processor 304 that data are ready. In the main processor 304 an interrupt routine recognizes the particular interrupt and generates the address of the device having data with a read data signal on the read/write line R/$\overline{W}$ and a virtual memory access signal on the VMA line. This produces a byte output to the microprocessor data bus via the transceiver 610.

For a write operation data are output in parallel on the data bus D0-D7 to the parallel inputs of one of the controller devices and loaded therein by the write signal and the respective address signals. The data loaded into the buffer of the control chip cause a serial transmission of the data bits from the TXD output to the transmitter 606. The transmitter thereafter transmits the particular digital data to the transmit terminal XMT+ of the device selected.

The controller 600, 602 chips appear as memory locations to the microprocessor 304 which may be read from or writter into in byte format. The controller chips 600, 602, transmitter 606, and receiver 604 perform the serializing of the data and the timing necessary for transmission and reception of the data.

Figure 10:
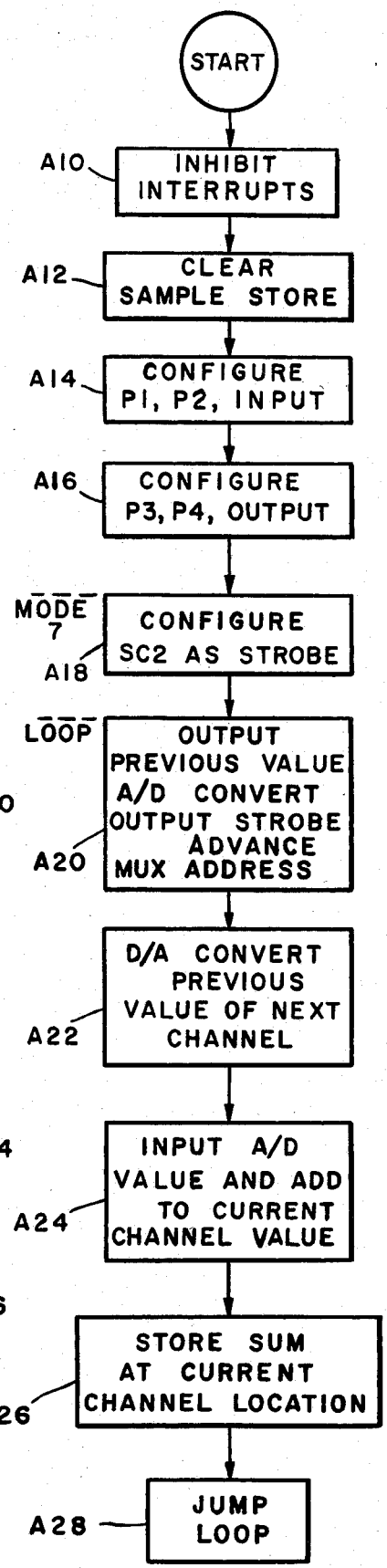
FIG. 10 is a system flow chart for the program which controls the microprocessor illustrated in FIG. 5.

With respect to FIG. 10 there is shown a flow chart for the control program stored in the microprocessor 232 (FIG. 5a) of the signal conditioning means 200. The program initializes the system control of the signal conditioning means by first inhibiting the interrupts to the microprocessor in functional block A10. Next the sample store is cleared in block A12 which allows a new set of data to be recorded therein. The sample store is an area in the microprocessor memory in which an integral sum of the digital differences for each channel can be stored. The sample store is illustrated figuratively in FIG. 10b and shows that it contains 16 memory locations each 16 bits long to provide storage for each individual channel.

Returning to FIG. 10 the program continues its initialization steps by configuring ports P1, P2, P3 and P4 of the microprocessor as either input or output in blocks A14, and A16. Thereafter an output terminal SC2 is configured as a control strobe line in block A18. Next in block A20 which is labeled LOOP the program simultaneously generates the analog to digital conversion output strobe along with outputting the previous channel value for the next channel and advancing the multiplexer address. These commands are provided simultaneously with one command by the microprocessor via the output ports. Block A22 illustrates the actual A1D conversion of the digital word output by the software command. The circuitry of the signal conditioning means thereafter carries out the software commands to produce the desired result.

After a cycle is started by generating the hardware commands from blocks A20 and A22, the converted difference value of the channel input from the A/D converter is read into memory. This difference value which is also latched into the data latch for further transmission to the preprocessor, is then added to the current value for the present channel and the sum stored in the sample store at the appropriate location for the channel. These functions are provided at blocks A24 and A26 of the programming prior to executing the next block A28 which transfers control back to the beginning of the loop at block A20.

The process of converting the multiplexed input channels to digital difference values is performed by continuously looping through the blocks A20–A28 of the microprocessor program and incrementing the multiplexer address channels. FIG. 10a is representative of a simplified block diagram of the conversion process for a single channel. A summing junction 301 is representative of the combinational circuit 220 of FIG. 5 where a reference voltage REF is subtracted from the input signal value $V_s(t)$ from the multiplexer. Additionally, the analog value of the signal at the time period just previous to the sampling $V_s(t-1)$ is subtracted at the summing junction 301. The output of the summing junction then is $V_s$ where the signal represents the difference between the sample values of the input signal over one time period. Since the sampling rate is relatively fast and the ECG signal waveforms do not change quickly with respect to the sampling rate, $V_s$ represents a small portion of the range over which the signal $V_s(t)$ can vary and is the digital derivative of the signal. The difference signal is digitized by the A/D converter 307 and latched into the latch 309 during one cycle.

The previous value signal $V_s(t-1)$ is generated by the digital to analog converter 303, and a digital intergrator 305 continuously summing the differences output from the A to D converter 307. The integrator 305 is represented as performing a digital integration which is the summation of the differences output from the device 307 over a time period relatively long compared to the sampling time. If the digital integration is performed with a large bit size integrator and matching digital to analog converter, then the analog difference signal at the summing junction is of a very high resolution. Although the A to D converter 307 converts only a portion of that signal, this high resolution is maintained with a analog to digital converter of lesser bit length than the elements 303 and 305 because only the difference is converted. In the preferred embodiment the bit size of the integrator 305 and the digital to analog converter 303 is 16 bits and the bit size of the analog to digital converter 307 is 8 bits.

FIGS. 10c–10f illustrate the timing for the conversion. The conversion cycle starts with a flash conversion on the rising edge of the STB signal which produces the 8 bit digital output. Once the conversion is complete, the next cycle is started by delaying a short time and then starting the A/D conversion and advancing the MUX channel address in FIG. 10e. This allows the maximum time for the analog signals to settle down before the conversion. The cycle is ended by latching and storing the difference in FIG. 10f at the falling edge of the strobe.

Figure 11:
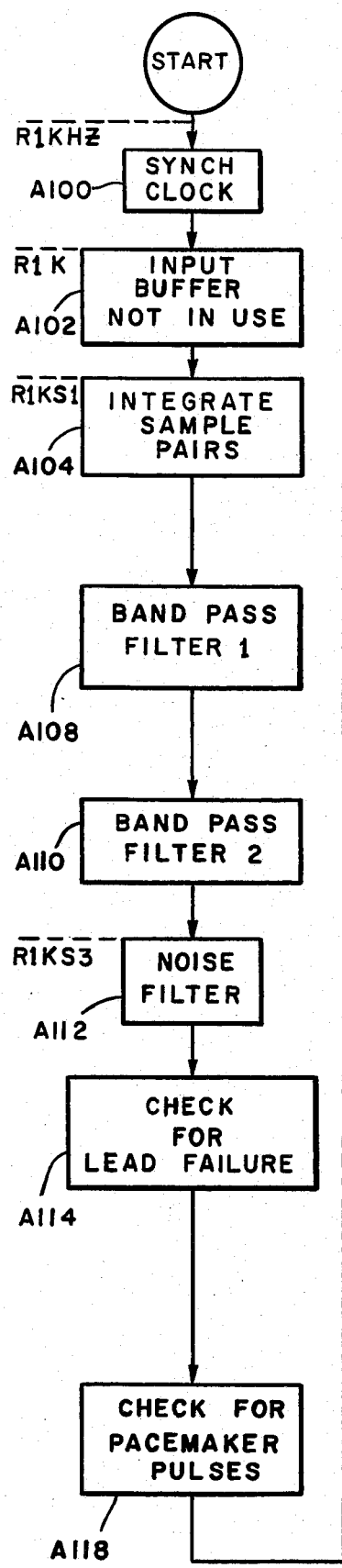
FIG. 11 is a system flow chart for the software program which controls the microprocessor illustrated in FIG. 7.
Figure 11:
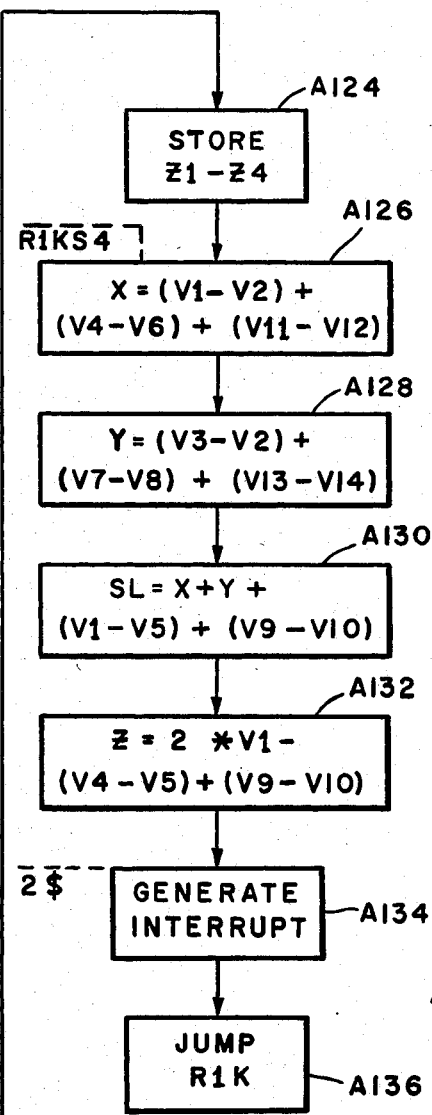

In FIG. 11 there is illustrated a system flow chart for the program stored in the microprocessor 272 of the preprocessor 202. In that figure the program initiates at block A100 with a subroutine that synchronizes the clock of the signal conditioning means 200 with input of one block of data to the input buffer memory 262. After the memory has been synchronized with the program control, the 256 word input buffer which is not in use is input to the microprocessor memory via block A102. Next the sample pairs of data are integrated in block A104 to provide a reconstruction of the signals which were differentiated in the conversion process.

Figure 12:
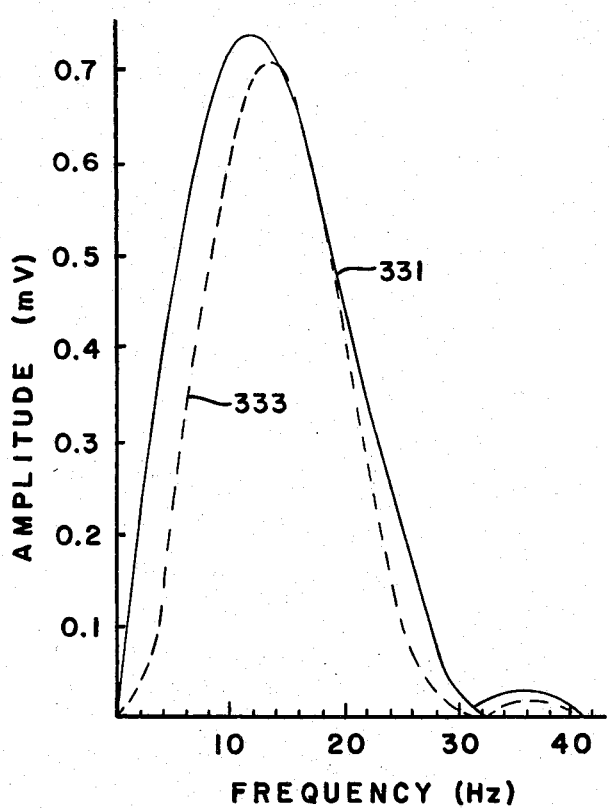
FIG. 12 is a graphical representation of the frequency response of the bandpass filters illustrated in FIG. 11.

The sample data is then fed through a bandpass filter in functional block A108 prior to its passage through a second bandpass filter in functional block A110. The bandpass filters with respect to their frequency response are illustrated in FIG. 12, where the more selective filter response is shown by a waveform 333 and the lesser selective frequency response is illustrated by a waveform 331. After the bandpass filters are applied, a noise filter in functional block A112 generates an average indication of the amount of noise that is in the sampled data. The program after providing the noise filtering, checks for lead failure in block A114 before jumping to a subroutine which detects pacemaker pulses by checking for maximum slope values between two samples for all the leads in block A118. The data blocks Z1–Z4 are then transferred to the output buffer memory in functional block A124. This provides a means for allowing the main processor 206 to access this data from locations in memory when the preprocessor 202 indicates they are available.

The three leads X, Y and Z are then formed by combining the differenced pairs and parallel summation inputs in blocks A126–A132. The X, Y, and Z leads are formed of their component parts and a lead for value SL is additionally formed in block A130 as the sum of X, Y and the V1–V5, and the V9–V10 differences. At this point the leads are averaged over four samples for alias filtering and formed of the parallel parts making up the individual leads.

The program then advances to block A134 where an interrupt is generated to indicate to the main processor that a complete cycle of the preprocessor 206 has occurred. Data for the main processor 206 are then available in the output memory buffer and can be input to the main processor for further calculations. The microprocessor of 272 the preprocessor 202 then executes a transfer of control to block 102 from block A136 to begin a new cycle.

Figure 13:
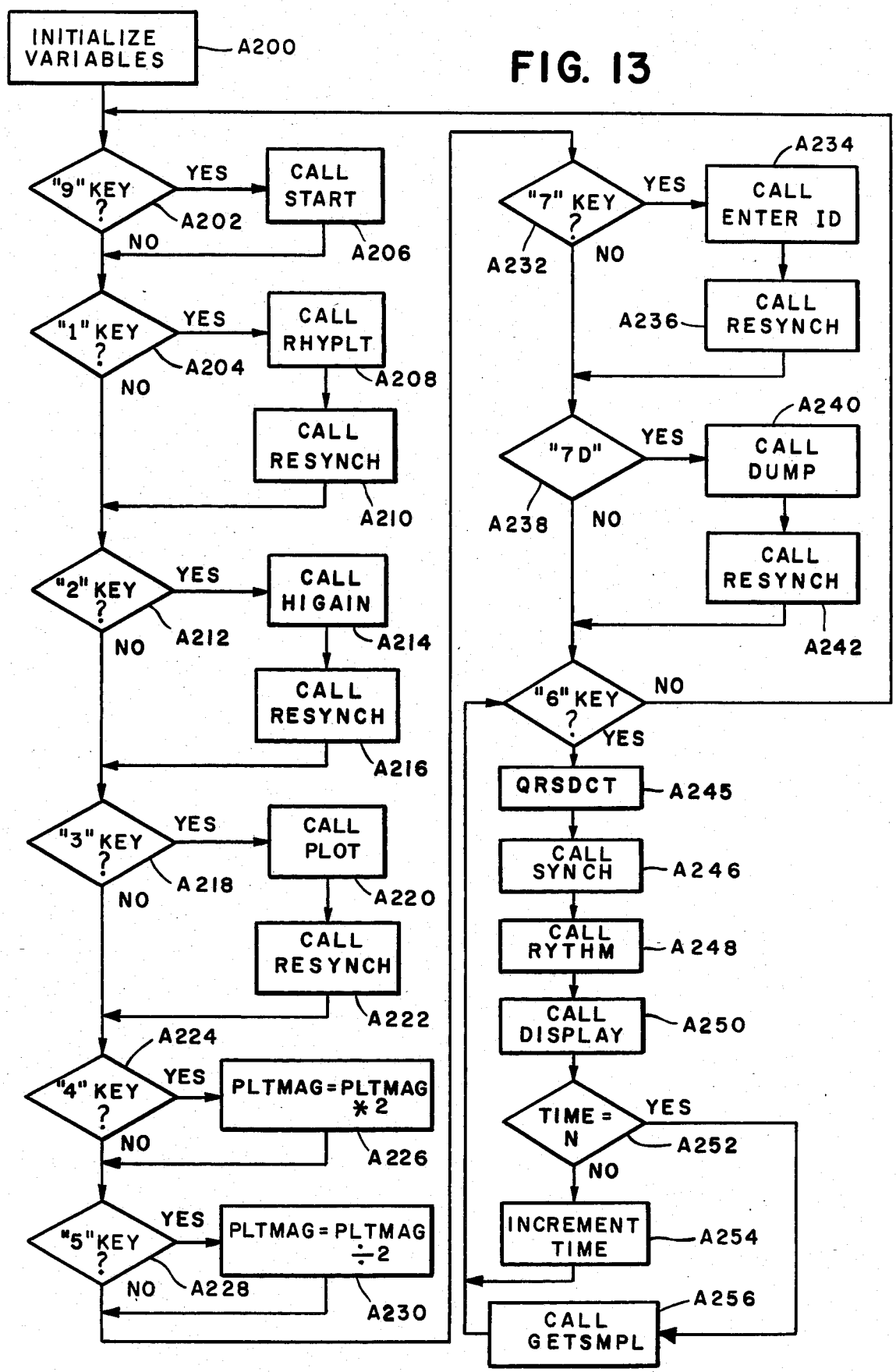
FIG. 13 is a system flow chart for the software program controlling the microprocessor illustrated in FIG. 8.

In FIG. 13 there is shown the system flow chart for the program stored in the microprocessor 304 of the main processor 206. A detailed program listing in the "C" language is provided for this program in the application just prior to the claims.

The main processor program initiates at the function block A200, where a number of variables are initialized, and structures, tables and arrays are set up for data manipulation. Thereafter, an operator controlled loop is entered in which the input data buffer from the CRT terminal 208 is checked to determine if any one of a number of control keys have been operated. The operation of particular keys indicate the function which the operator desires the system to perform. In block A202, if a "9" is found in the input buffer a transfer to routine called START is made in block A206. The routine START provides a reset function to place the system in an initialized state.

If a "1" key is found in the input buffer in the functional block A204, the affirmative branch of that decision block takes the program to a subroutine call in block A208. In that block a call to the routine RHYPLT is made to begin a rhythm chart recording of the X, Y, and Z leads. The rhythm plot routine will plot the sampled data from an input buffer in the main processor 206 and provide rhythm strip recording control for the plotter. After the plotter is done outputting the rhythm strip record, the program advances to block A210 where the subroutine RESYNCH is called to resynchronize the program to the incoming data.

The program next checks whether a "2" is in the input buffer in block A212 and finding an affirmative answer branches to block A214 where the subroutine HIGAIN is called. The subroutine HIGAIN is to provide a scaling of the data to a higher than average gain multiplication. After this program has finished, the program makes another call to the routine RESYNCH in block A216.

The program thereafter returns to the initial flow path where the CRT input buffer is tested to determine whether a "3" has been input. When the numeral representing this key is found the program, transfers to control block A220 where the subroutine PLOT is called. The PLOT subroutine is used for the interface between the plotter and output variables of the program. The routine also produces a call to the routine FIRFLT and the routine BUTFLT which performs and high pass filtering of the averaged data by a finite impulse response filter and a 4 pole Butterworth filter, respectively. The outputs of these filters are provided to the PLOT routine so they can be displayed on the plotter. By calling the subroutine PLOT the operator thereby produces a visual record of the special features detected by the system. As with the other subroutines after a call to the routine PLOT, the system reinitializes its clock with a call to the routine RESYNCH in block A222.

If either the key representing "4" or "5" is pressed than the plotter magnitude control variable is changed. The magnitude control variable PLTMAG is multiplied by two in A226 for a key representing a "4" and is divided by 2 in block A230 for a key indicative of an input of a "5".

A "7" key in block A232 will produce a call to the ENTER ID subroutine in block A234. In this subroutine a set format is output to the CRT display such that it requests the operator to enter his identification. For example, the routine requested the operator to type in the name of the patient, the time and other data critical to creating a record for the measurements. The program is thereafter resynchronized by making a call to the subroutine RESYNCH in block A256. The program will then return the main loop as previously described.

In block 238 the character in the input buffer tested for a "70" which causes the program to call a subroutine DUMP in block A240. The DUMP subroutine is a specialized routine called by this particular character sequence to provide outputs of the data buffers and memory locations for diagnostic and other purposes. The RESYNCH routine is again called in block A242 after the DUMP routine in block A240 has been executed.

Next, if the data input key is equivalent to "6", a subloop of the main routine is executed in which the generalized averaging is accomplished. Initially the subroutine QRSDCT is called in block 245 to detect the QRS morphologies with the aid of the bandpass filter data. Next the subroutine SYNCH is called in block A246 to calculate accurate timing marks for the input sample data. The SYNCH routine produces the fiducial timing marks from which an alignment is performed between beat waveforms. Next the subroutine RYTHM is called in block in A248 to produce the discrimination between average beat waveforms and the dominant rhythm complexes and subsequent to the execution of block A248 the subroutine DISPLAY is called in block A250 to provide a means for displaying failed leads on the CRT screen.

After completing the tasks in the prvious blocks, the variable TIME is tested in block A252 to determine whether it is equal to a predetermined number N. If not, TIME is incremented in block 254 before transferring control to block A244. If, however, TIME is equal to N then the routine GETSMPL is called in block A256. This portion of the program insures that the routine GETSMPL is executed at least as often as the variable TIME reaches its test contact N. The GETSMPL subroutine is used to input data from the microprocessor data buffer and to call another subroutine AVRG which actually completes the averaging task. The program then returns to block A244 and continues the loop until another key is depressed other than the "6" key thereby causing an exit of the subloop and a return to the start of the main loop at block A202.

The following is a generalized description of the averaging process that provides X, Y, and Z composites which are free from noise, odd beats, etc., while not losing the low amplitude, high frequency information necessary for the detection of the special features. The averaging process for the system comprises the detection and labeling of the beat waveforms, the synchronization of those waveforms which are of the dominant rhythm, and thereafter the averaging of sampling points in each of the waveforms which are acceptable for averaging. The detection and labeling function is accomplished by the routine QRSDCT which in general selects a number of types for the waveforms and a number of templates corresponding to each type from the bandpass filter samples. The routine sweeps the beat waveforms through the set of the templates to determine if they match any of the chosen templates within a certain degree and labels those which pass as to type.

A beat waveform is considered to have matched one of the templates if a ratio can be minimized to a particular reference level. The ratio is formed from the absolute difference between the template sample and the particular beat waveform sample being tested divided by the absolute sum of the values. The division by the sum of the values determines the nearness of the sample value to the template as a percentage of the total. In the preferred embodiment, if a beat waveform matches within 15% of a chosen template it is considered of that type.

A dominant rhythm template is chosen to discriminate between a dominant rhythm in the information received and other types of the beat waveforms in the routine termed RYTHM. Those waveforms which pass the matching process of the dominant rhythm template are then provided with a fiducial timing mark in the routine termed SYNCH which essentially marks the beginning of each waveform. The timing mark is produced by generating another template around the onset of the QRS complex and minimizing the difference between the template over a certain time interval of the QRS waveforms. The interval is chosen such that it will be substantially certain the onset of the QRS falls within that time period. The onset of the QRS waveform is chosen for the fiducial templating process because it is a landmark which is relatively available and reproducible for many of the beat waveforms and does not change as much as the following portions of the QRS for variances in respiration.

After the fiducial mark is inserted in each waveform, the waveform can be summed with the other dominant waveforms which have been detected in the routine AVRG. The summation takes place for all aligned samples of the waveform, and a number is recorded for how many samples were summed for each time position of the average waveform. The number of samples for each time position is necessary because all waveforms are not of the same length and thus some time positions may have more samples added to them than others. An average composite waveform for each of the X, Y, and Z is formed from these data samples by dividing the time positions for each sample by the number of samples which have been summed for that position.

Figure 21:
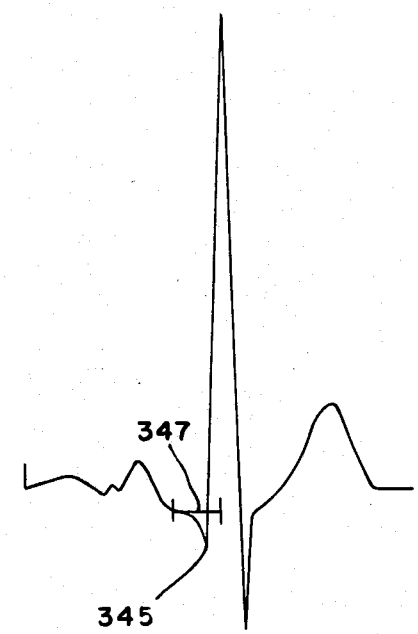
FIG. 21 is a waveform diagram of a QRS wave illustrating the fiducial timing alignment template around the onset point.
Figure 20:
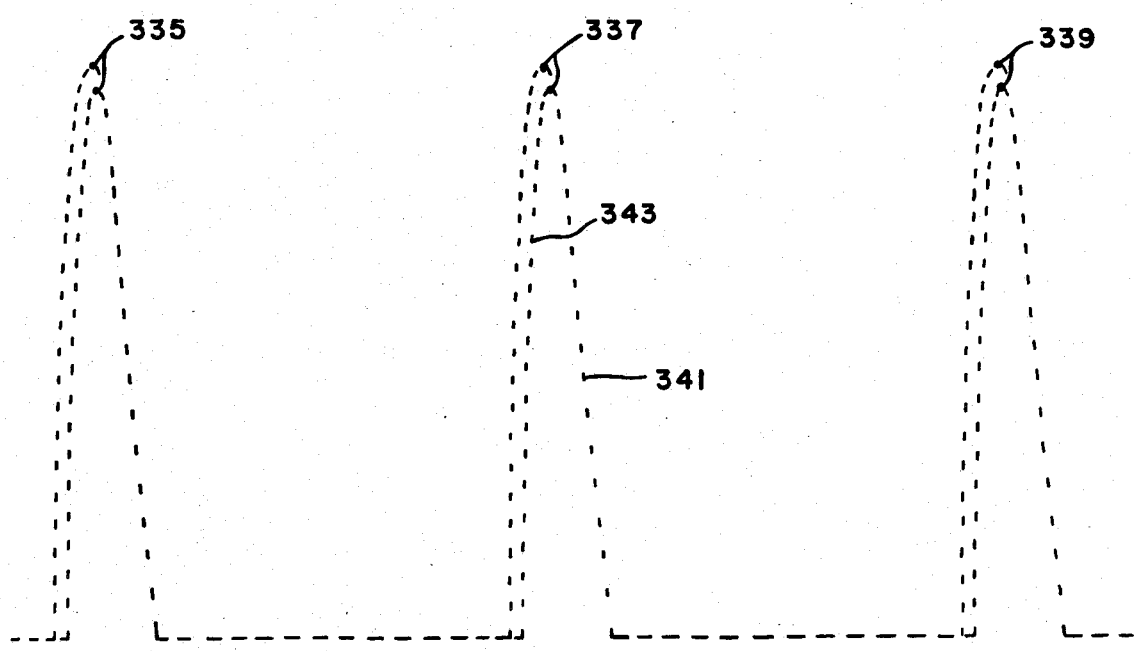
FIG. 20 is a pictorial diagram of the sample points from the bandpass filters illustrated in FIG. 11.

FIG. 20 is a graphical illustration of part of the detection and labeling process. Waveforms 341, 343 illustrate the samples of the outputs from the bandpass filters 215, 217 respectively. Almost all features of the waveform other than the R-segment frequency have been attenuated. The peak points of the filtered data 335, 337, 339 are used as the peaks for the waveforms. Thereafter, a template is formed of the X, Y, Z values of both bandpass filters at this position. The minimization of the ratio of this template takes place as previously described. FIG. 21 illustrates the area in which the template for the fiducial mark is obtained. The obstensible onset 345 is bracketed by the range 347 which is 5 millisecs before and 15 millisecs after the onset.

The routine QRSDCT will now be more fully explained with reference to FIGS. 14a–c. The QRSDCT routine accomplishes a detection and labeling function for the beat waveforms when it is called from the main program. If it has detected a dominant type waveform and labeled it it will return with a 0 such that the routines SYNCH and RYTHM can be called to align the detected waveform with others of type 0 and prepare it for averaging. The routine begins at block A300 where the RR interval is set equal to the present time minus the last time. Thereafter, in block A302 the variables of the routine are initialized to their starting values and the program continues to decision block A304. In that decision block it is determined whether or not there have been more than 350 preprocessor interrupts. If this is the case then the data buffer for the main processor is loaded with sample data to a greater extent than necessary for the program and therefore some of the older samples from the preprocessor can be discarded.

If the answer is affirmative the variables TIME and RR are incremented in block A306 prior to calling the subroutine GETSMPL in block A308. Calling GETSMPL causes one of the samples of the main processor data buffer to be taken and put into a working buffer for the detection and alignment routines. The routine also decrements the interrupt number such that a loop through blocks A304–A308 discards the oldest samples of that main processor buffer until the number is less than 350.

At that point the program continues to block A310 with the last data taken by the routine GETSMPL in the working buffer. In block A310 the two variables RR and TIME are again incremented to keep track of the position in the waveform and the amount of time spent in the loop respectively. Thereafter, in block A312 the routine GETSMPL is again called to provide a new sample for the working buffer. Two tests are now performed in blocks A314 and A318 to determine whether the lead failure variable LFAIL is not equal to zero or the key presently input from the CRT terminal is not equal to a "6". If either of these conditions are true which indicates there has been a lead failure or that the operator has pressed a different key than "6", then block A316 is executed before the routine returns. The function in block A316 is to set the flag QRSF to 1 such that the averaging and alignment routines will not be executed.

If these initial tests are passed then the program continues in block A320 where the RR interval is tested to determine whether it is equal to a constant 16. If it is then in block A322 a minimum power reference MNPWR is set equal to an initialized reference value. Next in block A324 a pointer Pb is developed for the detection filter data such that it can be addressed. Following this operation in block A326 the absolute value for the X, Y, and Z signals in the detection filter data are summed together to produce the variable POWER. This summation is an indication of the peak power level at the time position of the waveform being examined. Next tests in A328, A330 are accomplished to determine whether the power calculated in block A326 is greater than the minimum power variable MNPWR that was calculated in block A322. If the variable POWER is greater than the minimum power and at this time the peak power is still zero then the peak power variable PKPWR is set equal to the calculated power.

At this time the program has determined that the waveform has either passed the minimum power test or it has not in block A334. If the peak power is still zero, a test is performed to determine whether the peak time is greater than 20 time segments after the peak in block A348. If not then the next sample and an iteration of the loop is accomplished by transferring the control of the program to block A310.

However, if the peak power is now greater than zero thereby passing the affirmative test in block A334, a subroutine XFRTPT will be called in block A336 to transfer the detection filter template to a buffer labeled ZTMP. Thereafter, a subroutine MATCH is called to match the present samples against the detection filter template. This routine minimizes the ratio for the samples and returns the absolute difference between the sample and the template and the absolute sum between the sample in the template at the time of the minimum match. Additionally the routine returns the variable QTYP which is indicative of the label type applied to the present data.

In block A340 the power term is compared to the peak power term and replaces it in block A344 if greater than that variable. If the power of the present sample is less than the peak power then the peak time PKTIME is incremented by one in block A342. Subsequently, the decision block A348 is executed to determine whether the number of iterations has brought the program to a peak time of greater than 20. This point in the program indicates that the sampling and sweeping of the waveform through the template has taken the present time position 80 milliseconds past the peak.

Next in blocks A350-A354 the minimum power variable MNPWR is calculated to insure that it does not become greater than twice the variable AMIN. In decision block A356, if the number of QRS waveforms that have been detected is zero then the time variable TIME is set in block A358 to the last time a QRS was detected minus a constant 10. Thereafter, in block A360 the pointer PS is set equal to the starting address of the match and filter templates to provide another templating process. In block A362 the pointer PB is set equal to the address of the detection filter element [0] which is calculated as the variable A. This is the detection filter sample data at the time of best match as determined from the match routine.

Thereafter in block A366 the program tests whether the ratio that was returned from the match routine is less than 400. If the test is true the program continues to block A368 but if false the program skips block A368-A394 because the ratio is too large to be minimized and it is evident that the waveform detected is not the type matched.

However if the program takes the path to block A368 a further template is stored by routine XFRTPT in the next memory area following ZTEMP which is the filter data one time period prior to the data stored in block A364. In addition subroutine XFRTPT is called again in block A370 to store another template in the next memory area of ZTMP which is the detection filter data one time period subsequent to the best match filter data. Next in block A372 and A374 variables DIF1, DIF2 and the pointer PB are initialized. The pointer Pb is initialed to the first address of the template data buffer ZTMP.

A loop comprising blocks A376, A378, A380 and A382 are executed to calculate a value for the variables DIF1 and DIF2 from the template data stored in the buffer ZTMP. In blocks 386 and 388 the differences are then multiplied by constant and divided by the variable SUM which was returned from the initial match. In block A390 the difference DIF1 is tested to determine if it is less than RATIO and if it is then in block A392 that value replaces the value of the variable RATIO. If not the second difference DIF2 is tested to determine whether it is less than the variable RATIO in block A394. If the test is affirmative the value of the difference DIF2 replaces the value of the variable RATIO in block A396. Thus, the routine checks one template before and after the best match template to ensure it has correctly found a minimum.

If by this time the ratio is less than 150 as determined by block A398 the program passes to block A412. However, if the ratio is greater than 150 the program has decided that this is not a type O or type of waveform which is fit for averaging. Therefore in block A400 the number of QRS complex types, NQTYP, is tested to determine whether it is less than 3, and if it is, then the program sets the last time equal to the present time minus 10 in block A404. The type label TYP for the waveform detected is set equal to the present value of QTYPE in block A406 and that variable incremented one in block A408. Next the subroutine XFRTPT is called to transfer the filter detection template at the peak power point of that waveform in the buffer area template. If the number of QRS types is greater than 3 as indicated by a negative branch from block A400 then the type of the waveform is set equal to 2 and the program transfers control from block A402 to block A412.

In block A412 the program continues by decrementing the RR interval by the difference of the variable LTIME and (TIME+10). Afterwards in block A414 the variable NQRS is tested to determine whether the number of QRS waveforms detected is 0. If the answer is affirmative then the RR interval is set to 200 in block A416 and the program proceeds to block A418. In that block the number of QRS waveforms detected NQRS is incremented by one and the variable TIME decremented by 23 in the next block A420. To exit the routine the flag QRSF (indicating that a QRS waveform has been detected) is set equal to zero in block A422.

Figure 15A:
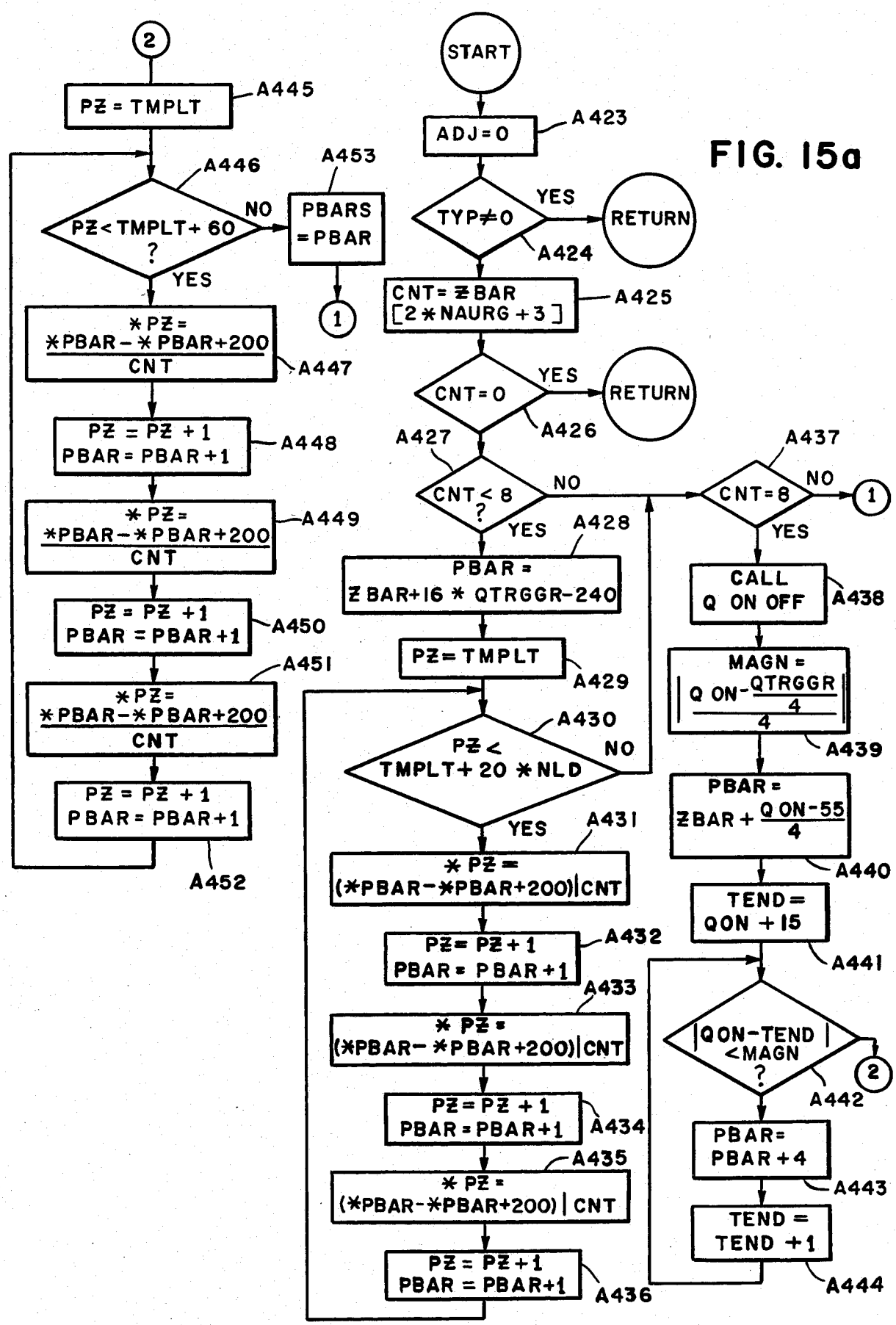
FIGS. 15a-15c form a detailed flow chart for the routine SYNCH illustrated in FIG. 13.
Figure 15B:
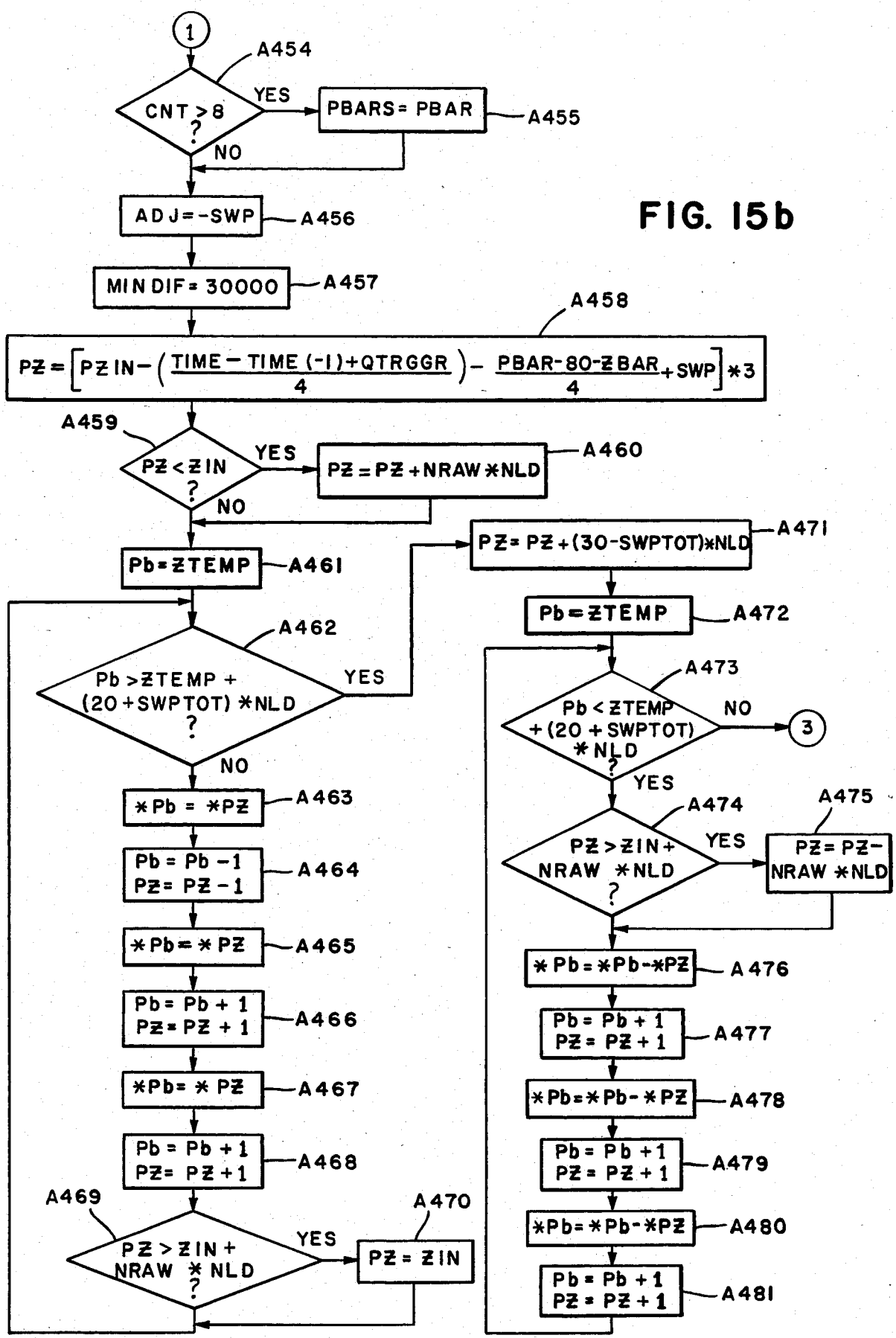
Figure 15C:
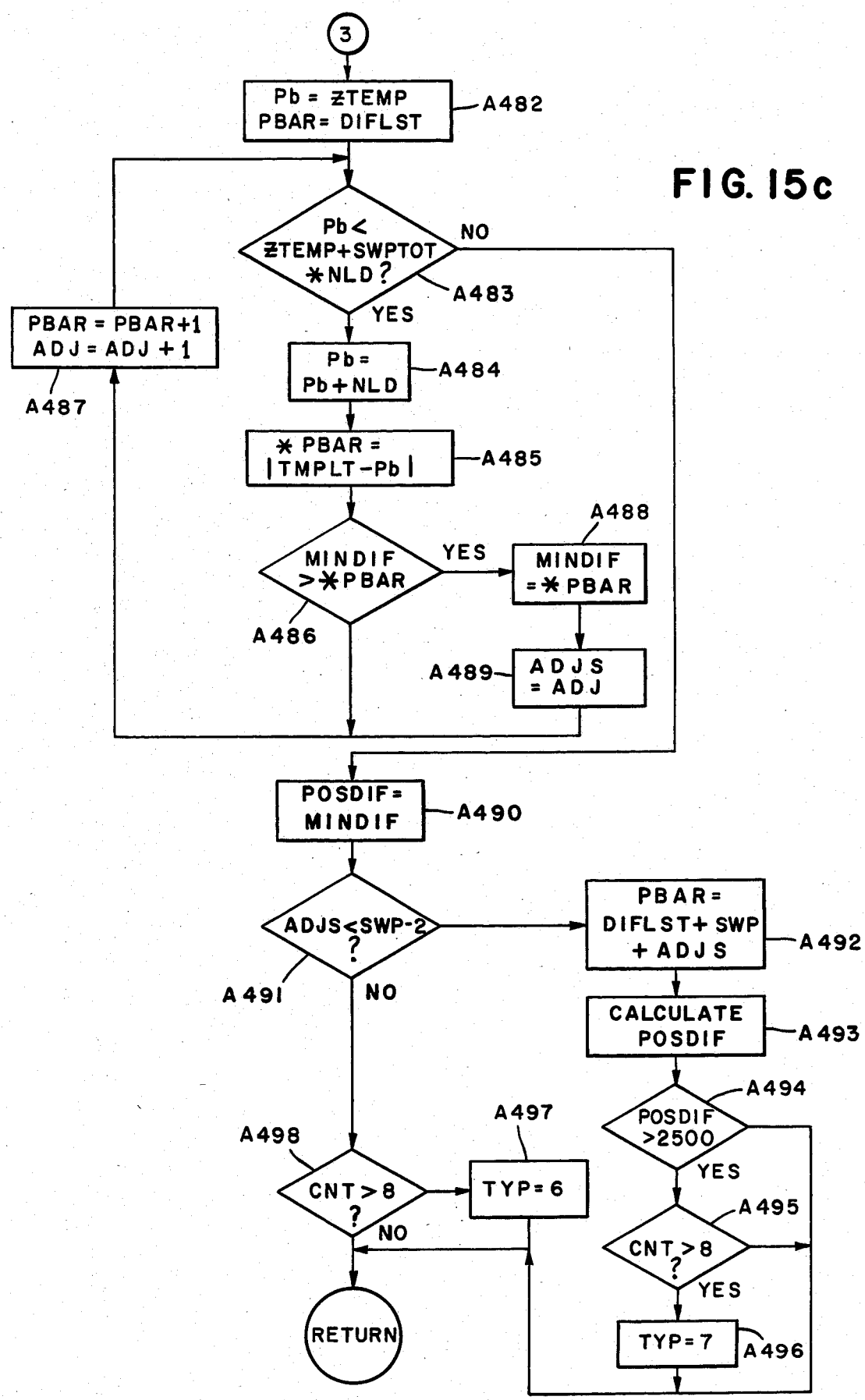

The next routine that will be discussed is the part of the program SYNCH that provides the fudicial timing mark for the waveforms. The program is better illustrated in FIGS. 15a–c where it begins in block A423 by setting the variable ADJ equal to zero. The variable ADJ will be used to adjust the onset mark of a waveform such that it aligns with all the other waveforms in a normalized manner. In block A424 the variable TYP is tested to determine whether it is equal to zero. If the waveform is not a type zero waveform then the synch routine automatically returns because only those waveforms of type zero will be averaged. Thereafter the variable CNT is set equal to a number stored in the ZBAR array element [0] in block 425. If this count is zero as tested in block A426 then the program returns.

However if the count is less than eight a path including the affirmative branch of block A427 is executed to transfer control to block A428. In that block the variable PBAR is set equal to a number which is 60 milliseconds prior to the detected peak which is indicated as the variable QTRGGR. In the next block A429 the pointer Pz is set to point to a buffer area template. Next a block of instructions from functional block A430–A436 is executed to form an average template from ten increments prior to the Q trigger detection point to ten units after that point. This template is averaged over the first eight counts of the routine as the loop is executed.

Next if the count has now increased to eight the affirmative branch of block A437 is taken to the call up the subroutine QONOFF in block A438. This subroutine determines the onset and offset of the QRS waveform from landmarks in the sampled data. After the onset has been determined, the amplitude of the particular waveform is calculated as the difference between the peak and the onset value in block A439. This value is divided by four to generate a reference value with which to compare the template. Thereafter the end variable TEND is defined as the onset point plus fifteen in block A441. Next a loop is entered in which the absolute difference between the onset and the end point is compared to the magnitude of each sample and the end point incremented until the test in block A442 is affirmative. When this occurs the two points QONSET, TEND have been moved across the waveform to where they reach a point which has an amplitude which is one quarter of the R wave amplitude. Thereafter in block A445 the pointer Pz is set equal to the beginning of the template address and a new template formed in loop 446-452 of twenty points from five milliseconds previous to the onset point to fifteen milliseconds after the onset point. The program then exits the loop with a negative branch from block A446 to block A453 where the pointer PBAR is remembered as the variable PBARS.

For iterations greater than eight in block A454 the pointer PBAR is initialized to the constant PBARS and the program continues to block A456. In that block the variable ADJ is set equivalent to the sweep variable SWP, and in the following block A457 the variable MINDF is set equal to a large constant. The pointer PZ is then calculated in block A458 as three times the quantity of a summation of four terms. The first term in the summation is the address PZIN of the input data buffer. The second term is the negative of the present time minus the last time plus Q trigger divided by four. The third term is $-[(PBAR-80)-ZBAR]/4$ and the fourth term is the sweep variable SWP.

The pointer Pz indicates where to start the templating process in the raw data. In the next two blocks A459, A460 the program checks to insure that the pointer Pz is not less than the starting address of the input buffer ZIN. If it is, then the address is incremented by a constant (NRAW×NLD) which brings the pointer back to the beginning of the input buffer. Thereafter the pointer Pb is set equal to the beginning of the temporary buffer ZTEMP where the calculated template data is stored. In the loop formed by next blocks A462-A470 the raw data from the buffer PZIN are transferred to the working buffer ZTMP. Each lead has (SWPTOT+20) number of raw data samples transferred where SWPTOT is equal to fifteen from previous program definition.

After the loop has been executed and all the data samples are stored in the temporary buffer ZTEMP, the affirmative branch from block A462 takes the program to block A471 where the pointer Pz is redefined as its present value incremented by ((30-SWPTOT)×NLD). Next the pointer Pb is set equal to the start of the temporary buffer ZTEMP in block A472.

A loop comprising blocks A473-481 follows in which the template data is subtracted from the raw data and the differences put back into the temporary buffer ZTEMP. The program continues after the transfer has been completed by taking the negative branch from block A473 to block A482. In this operation the program resets the pointer Pb to the start of the temporary buffer ZTEMP and sets the pointer PBAR equal to a variable DIFLST. Next a loop is entered in block A483 where the program will repeat the steps of block A484 to block A489 until the pointer Pb is equal to the start of the buffer plus SWPTOT×NLD. In this loop the data in the temporary buffer ZTEMP are subtracted from the template data and the differences tested to determine whether they are less than a variable MINDIF. If the difference calculated is less than the previous minimum difference than that value replaces the variable MINDIF.

Accordingly, an adjustment factor ADJ is also remembered by setting it equal to the saved value ADJS. Otherwise, if the value of the difference calculated in block A485 is greater than a previous difference, then the pointer PBAR is incremented and the adjustment factor ADJ is incremented in block A457. Thus an adjustment factor ADJS is calculated by searching for the minimum difference between the template data and the raw data.

The minimum difference in block A490 is set equivalent to a variable indicating a possible difference POSDIF which might occur between two of the adjustment time periods. After that block is executed and only if the saved adjustment factor ADJS is less than SWP-2 (which is equivalent to five milliseconds) does the program enter a loop starting at block A492. If on the other hand the adjustment factor is greater than five milliseconds then in block A498 the count is tested to determine whether it is greater than eight. If it is then the waveform is labelled a type "6" in block A497 and if not simply returns to the location from where it was called.

If the adjustment factor ADJS is less than SWP-2 then a pointer PBAR is set equal to (ADJS+SWP-+DIFLST). For these variables a value for the variable POSDIF is calculated by a interpolation using a hyperbolic estimation between time periods. After the calculation is accomplished, in block A494 the variable POSDIF is tested to determine whether it is greater than 2500 and if not the program simply returns. However, if the variable POSDIF is greater than this constant and the count is greater than 8 as tested for in block A495 then the type for the waveform is set equal to 7 in block A496.

The routine RHYTHM will now be more fully explained with reference to FIGS. 16a-b. The rhythm routine performs certain tests on the type of beat waveform labeled in the QRSDCT routine and mandates a certain format for the waveform prior to averaging. Additionally a template for the dominant rhythm or type O waveform is calculated in this routine. The last task of the routine is to assign the alignment mark which was calculated in the routine SYNCH.

The routine begins at block A600 where the pointers PZBAR, Pc, and Pb are initialized. The pointer PZBAR is set equivalent to zero while the pointer PC is initialized to the address beginning the QRS buffer PQRSB. The pointer Pc initialized to the start of PQRSB plus an increment value found in the first element of the array QRSLST. The next two functional blocks A602 and A604 are to prevent the pointer Pb from obtaining a value greater than QRSLST+16. If that value is exceeded then the pointer Pb is reset equal to the beginning of the data list QRSLST in block A604. Next a test is performed in functional blocks A606-A612 where the type of the beat waveform, its length, and power are compared against reference values. If the present waveform type as indicated by the variable TYP is not zero and its length is less than 45 millisecs, then the program considers this not a normal waveform and therefore the detection must have been of either of transient noise or possibly a T wave segment. If both of these conditions are true, then a second set of tests is performed in block A610 and block A612 to determine whether the last type of the waveform LTYP is zero and whether the present peak power PKPWR is less than the last peak amplitude LPKAM8 If either one of these questions is answered in the affirmative then the program transfers to block A614. In block A614 the variable TIME is reset to the value of RTIME and the number of QRSs (NQRS) decremented in block A618. Since the routine cannot average this waveform, the program will return from the location from which it was called.

However if the sample data pass the tests in blocks 610, 612, another set of tests is started in block A620, where it is determined whether the last waveform type QTYP was equal to zero and whether the last peak power LPKPWR is greater than the present peak amplitude PKAMP. If this is the case then another test is performed in block A622 where the RR interval is tested to determine whether it is less than 45 millisecs or greater than 75 millisecs and the present type waveform TYP is zero. If all these conditions are present, then the previous waveform was also improperly counted. To take this improperly counted waveform into the account, RR interval is incremented by the constant RINT, the time RTIME is incremented by RR16, and the number of QRSs counted (NQRS) decremented in block A624.

Subsequent to these two sets of operations, the program will now attempt to label the waveform as a type zero such that a template can be selected for the dominant rhythm. The selection consists of initially determining in block A626 if the number of QRSs detected, NQRS, to this point is greater than two and less than eight. If the variable NQRS is in this range, the type variable TYP is not yet equal to zero, and the present RR interval greater than RR16/16 then the program will assign this waveform the label type O. The number of QRSs detected is reset to 2 in block A628 and the template for the particular waveform is transferred in block A630 into the buffer TMPLT by the subroutine XFRTPT. Next in block A632 the type variable TYP is set equal to zero and the number of these types counted NQTYP is set equal to one. Thereafter, in block A634 the average array ZBAR is cleared to zero.

As soon as the program recognizes eight waveforms of similar type in the QRSDCT routine it will assign a permanent template to the label type zero and this will become the dominant rhythm. If however not enough waveforms are detected to make a permanent assignment, the next waveform that appears that is not type zero and meets the other criterion will cause a relabeling of type O. Thus, the dominant rhythm must appear for eight consecutive beats before the permanent labeling takes place.

At this point the program proceeds to block A636 where the variable QCNT is incremented to provide a running count of the number of QRS waveforms found to this point. Next in block A638 the variable NQRS is compared to the number 16 to determine if there have been sixteen QRSs counted to this point in the program. If the answer is affirmative then the variable RR16 is set equal to the RR/4. Otherwise in block A642, the variable RR16 is set equal to the quantity (TIME-RTIME).

The values of the present variables are thereafter assigned in block A644 to values of the previous variables and the pointer PBAR calculated in block A646. The pointer PBAR is calculated as the position in the average data where the waveform should have the fiducial mark inserted. Next in blocks A648 and A650 the pointer PBAR is tested to ensure that it is not less than the beginning of the average data buffer ZBAR. If it is then its value is set equivalent to the start of that buffer in block A650. The value of the pointer PBAR is stored in an intermediate variable PZBARI in block A652 to remember that value.

In block A654 the pointer Pc is calculated from the expression shown. The pointer is calculated to point to where the fiducial timing mark should be stored in the raw data buffer ZIN. The location is calculated as a function of a term indicating the start of the raw data buffer PZIN, a term taking into account the peak period (TIME-LTIME-QTRGGR)/4, a term taking into account the fiducial mark in the average data (PBAR-ZBAR)/4 and the adjustment factor ADJ which was calculated previously in the synchronization routine.

Next in the blocks A656 and A658 the program ensures that the pointer Pc is not less than the start of the raw data buffer ZIN. If it is, then Pc is incremented by a factor (NRAW×NLD) in block A658. Thereafter the value of the pointer Pc is assigned to the variable PCYCLE in block A660. Next the pointer Pb is assigned to the QRS buffer pointer PQRSB in block A662. Having completed all of its functional tasks the RYTHM program then returns to the location from which it was called.

The subroutine AVERG will now be more fully explained with reference to the detailed flow chart illustrated in FIG. 17. The routine initializes two pointers Pb, Pc upon entry in block A670. The pointer Pb points to the average data buffer PZBAR and the pointer Pc points to a buffer PQRSB containing information on the last sixteen QRS waveforms which were averaged.

In block A672 a test is performed to determine if this is the first element of the ZBAR array. If it is, as indicated by Pb=0, then no averaging has taken place yet, and a preliminary path must be completed before the actual averaging routine can be accomplished. The program therefore continues to block A476 where the variable AVTYP is tested to determine whether it is not zero. If it is nonzero then the waveform samples are not of an average type and can not be averaged. Thus, the variable AVTYP is set equal to −1 in block A678 to prevent the routine from averaging any waveforms until the other routines detect a waveform of the specified average type. The program that returns from this path without doing any further calculation.

However, if the variable AVTYP is zero then an the preliminary averaging path formed of blocks A680-A688 is executed. Along this path in block A680 three starting values for each waveform are stored. These values are used as values to subtract from the rest of the data samples to remove any offset value in the amplitudes. Next the sums of the first 100 elements for each lead is formed in block A682. The first 100 samples is averaged because the averaging routine is catching up with the other parts of the program which may be already 20 millisecs beyond the peak of the present waveform. However, for time management purposes the averaging routine is not allowed to accomplish all the averaging the first time through the loop.

Next in blocks A684, A686 the pointer to the raw data being averaged PZ and the pointer to the location where the average data is being stored Pb are remembered by the variables PZRAW, and PZBAR, respectively. Thereafter in block A688 the noise for the average data samples is calculated by taking the second difference of each point and incrementing a variable if it is greater than the last noise value calculated. The program has now finalized the prelimary path for averaging and returns.

The next time the averaging routine is called Pb will not be equal to zero and the program will take the path to block A674. A test in block A674 is performed to determine if Pb is less than the end of the buffer ZBAR. If the program has not completed the averaging, the answer to the test will be affirmative and transfer control to block A694.

In that block, the next four samples of the X, Y, and Z leads are added to the composites being formed. The program then continues by remembering the pointer values for Pz, Pb in blocks A696, and A698. For each time the routine is called thereafter until the end of the data, four samples of the buffer are added to the values of the composites. This operation maintains the averaging of the samples substantially synchronous with obtaining of the samples by the GETSMPLE routine.

When the limit of the data buffer is exceeded in A674, the program will advance to block A690 where the variable AVTYP is set equal to $-1$. As was the case with block A678 this action causes the AVERG to stop averaging data until the other routines find and detect more good data. Before exiting back to the calling routine the variable PZBAR is set equal to zero for a resetting of the program.

Figure 18:
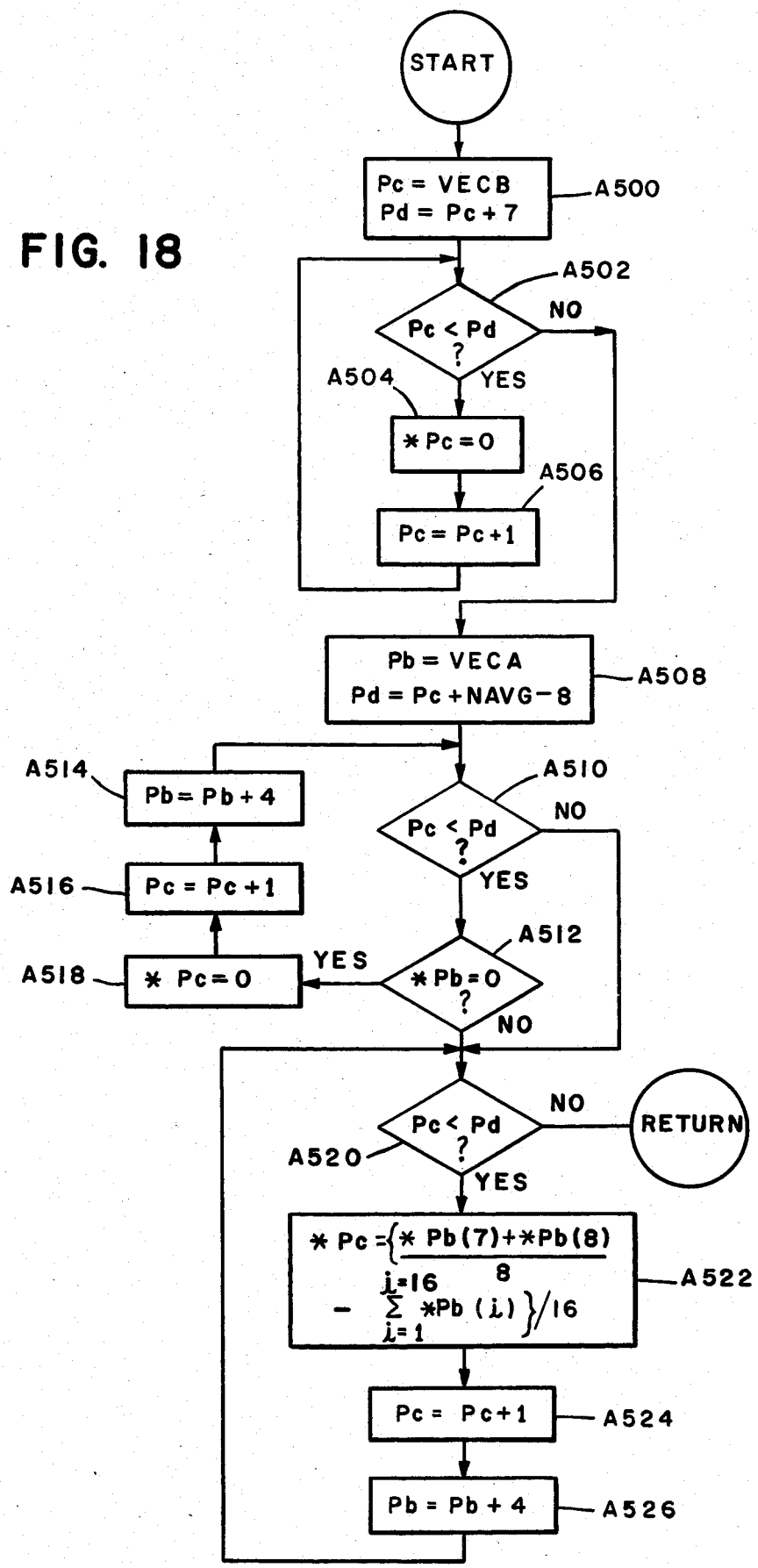
FIG. 18 is a detailed flow chart of the routine FIRFLT called from the routine PLOT illustrated in FIG. 13.

With respect now to FIG. 18 there is shown the detailed flow chart of the FIR filter routine termed FIRFLT. The FIR filter routine takes the sampled data from the buffer where it was placed after averaging and produces a finite response filtering of the high pass type. The result of the digital filtering is stored in an output vector which is used by the subroutine PLOT to display the data. Initially the subroutine starts at block A500 where a pointer Pc is set equivalent to the address of the beginning of an output vector Vecb and the pointer Pd is set equivalent to the original pointer Pc+7+. This establishes two pointers, one to the start of the output vector and another to the eighth position of that vector.

The program continues with a test block A502 in which it is determined whether Pc is less than Pd. If the answer is affirmative, then the contents of the address Pc is set equal to zero in block A504 and the pointer incremented in block A506 where control is returned to the test in block A502. This incrementation and looping continues until the test in block A502 is failed. This portion of the routine fills the first eight locations of the vector Vecb with zeroes. Thereafter a pointer Pb is set equivalent to the starting address of an input vector veca in block A508. In addition, the pointer Pd is given a new value (Pc+NAVG−8). This sets the pointer Pd equivalent to the length of the input buffer which is NAVG. The program then transfers control to block A510 where the pointer Pc is tested to determine whether it is less than the pointer Pd. If the test is affirmative, then a test in block A512 examines the contents of the location in the input vector pointed to by Pb to determine whether it is zero. If the test is affirmative indicating that the value of data in the input buffer is zero then the corresponding element in the output buffer is set equal to zero in block A518. In succession the pointer Pc is incremented by one in block A516 and the pointer Pb is incremented by 4 prior before returning to the decision block A510. The program continues this loop until either all of the elements in the input array have been tested as indicated by a negative path from block A510 or a nonzero element in the input array is found as indicated by a negative path from the block A512.

At this point the test in block A520 is executed to determine whether the pointer Pc is less than Pd. If the test is negative then the computation in block A522 is executed. In this computation the location in the output vector pointed to by Pc is filled by the difference of two terms. The first term the summation of the seventh and eighth terms of the input array following the location pointed by Pb and divided by eight whereas the second term in the computation is the summation of the next sixteen elements in the array after Pb divided by 16. This computation therefore calculates a value for the output array Vecb which is the one half the average of the seventh and eighth elements minus the average of the next sixteen elements of the input array. It is seen that if the elements Pb (7) and Pb (8) are the center elements of the sixteen used for filtering purposes. Subsequently, in blocks A524 and A526 the pointer Pc is incremented by one and the pointer Pb incremented by 4 to fetch the next sample which will be filtered. The loop filters each sample in this manner successively until all the average data for the X, Y, and Z terminals have been filtered.

It is evident in this type of filtering that the response to the filter is not contaminated with samples which are more than 16 locations ahead of the location being filtered. Thus, the filter has a response that is finite, does not cause a phase shift change and does not cause a change of polarity in the signal or ringing on account of the filter. Therefore it can be assumed that the high frequency reversals in a plot of the filtered data are caused by features of the waveform and not by the filter.

Figure 19:
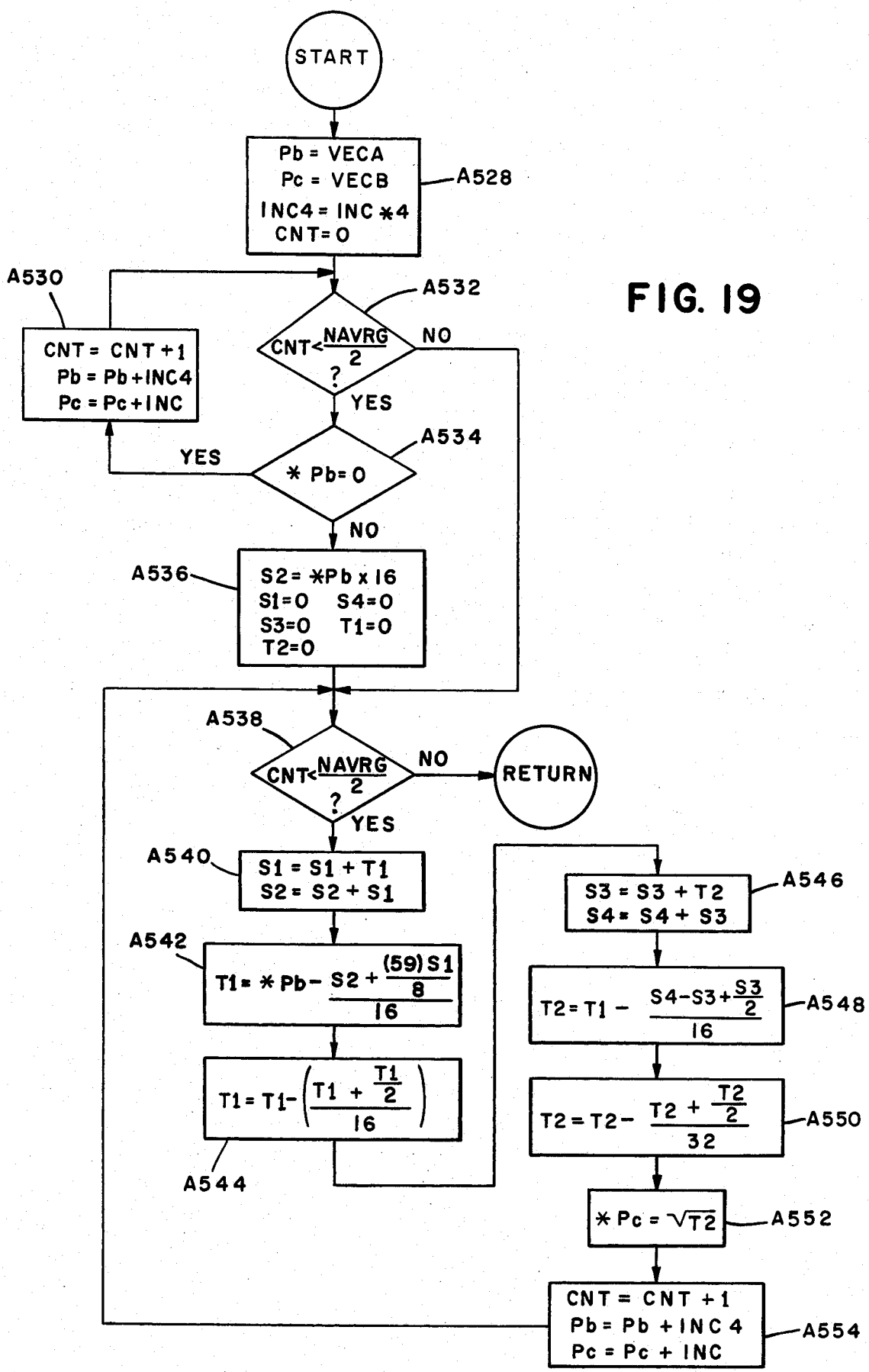
FIG. 19 is a detailed flow chart of the routine BUTFLT which is called from the routine PLOT illustrated in FIG. 13.

With respect to FIG. 19, a more detailed flow chart of the four pole Butterworth filter will now be more fully explained. The Butterworth filter illustrated in the figure is a digital synthesis of a four pole analog Butterworth filter having the transfer function T(s) where:

YT(S)=Z
Y is the input,
2 is the output,
S is the Laplace variable, and $$T(s) = \frac{1}{\left(1 + \frac{C1}{s} + \frac{1}{s^2}\right)\left(1 + \frac{C2}{s} + \frac{1}{s^2}\right)}$$

Note that: $T(s) = T_1(s)\, T_2(s)$ where, $$T_1(s) = \frac{1}{\left(1 + \frac{C1}{s}\frac{1}{s^2}\right)}$$

$$T_2(s) = \frac{1}{\left(1 + \frac{C2}{s}\frac{1}{s^2}\right)}$$

Where the two denominator terms each form two poles of the filter and coefficients C1 and C2 are arbitrary filter constants to provide correct frequency response.

Each term can be represented in the digital domain by rearranging the equations for the transfer functions $T_1(s)$, $T_2(s)$ and twice integrating both sides of the resulting equations. Digitally the integration is performed by successive summations.

$$Z_1 = Y\, T_1(s) \qquad (1)$$

$$Z_1 = Y - C_1 \int Z_1 - \int \int Z_1$$

$$Z = Z_1\, T_2(s) \qquad (2)$$

$$Z = Z_1 - C_2 \int Z - \int \int Z$$

The integration for forming the two terms of the transfer function is done digitally by a successive summation first for the equation (2) and then for the equation (2) above as will be more fully explained hereinafter. Initially, the program starts at block A528 where pointers Pb and Pc are set equivalent to the starting locations of a pair of vectors Veca and Vecb, respectively. These vectors represent an input buffer which has the unfiltered data in it and an output vector where the filtered data will be placed. Next, a variable INC4 is set equal to four times the counting increment INC. Further in that functional block the variable CNT is set equal to zero.

Next in block A532 a test is performed to determine whether the variable CNT is less than one half the variable constant NAVRG. NAVRG is a constant indicating the length of the input buffer data and CNT is a counter variable for determining where in the input data the pointers are referencing. The division of NAVRG by one half is to provide a filter which will filter in a forward or reverse direction from substantially the peak of the QRS waveform. It is noted that the increment INC can be either positive or negative and therefore when the subroutine is called the input data can be filtered in a forward manner up to the half way point of the waveform and then reverse averaged from the end of the waveform by calling the subroutine again and simply negating the increment variable.

If the variable CNT is less than the final address, then the affirmative branch of block A532 transfers control to block A534 where the contents of the location pointed to by Pb is tested to determine whether it is zero. If it is, then CNT is incremented by one, Pb is incremented by INC4, and Pc is incremented by INC in block A530 before returning to the test in block A532. This part of the program steps through the data in the input vector until it finds a nonzero element or the range of the data is exceeded. If the range is exceeded, the negative branch for block A532 transfers control to block A538, otherwise the negative branch of block A534 transfers control to block A536.

As soon as a nonzero element is located, the variables for the filter S1, S2, S3, S4, T1 and T2 are initialized. The variables S1, S3, S4, T1 and T2 are initialized at zero while the variable S2 is initialized to 16 times the value of the first nonzero element of the input array. After the initialization step in block A538, a test to determine whether the variable CNT is less than the constant NAVRG/2 is accomplished. If the result is negative then the program has filtered all the elements of the input data vector and has stored all the newly filtered values in the output data vector. If the result is affirmative the program branches from block A538 to begin the filter routine. In block A540 the variable S1 is replaced by S1+T1. Additionally, S2 is set equal to the old value of S2 plus the new value of S1.

With these new values the calculation in block A542 is accomplished where the variable T1 is set equal to the value of the location of the pointer Pb minus two additional terms. The first additional term is a constant times S2 and the second term is a constant times S1. Comparing the blocks A540 and A542 it is seen that the calculation accomplished in A542 is identical with a digital implementation of equation (1) where the input term has subtracted from it a first summation (S1) and a second double summation (S2). This calculation therefore provides the first two poles for the transfer function indicated above. Next, in block A544 a gain equalization factor is applied to T1 because of the digital format of the filter.

Thereafter, in block A546 the variable S3 is initialized to the old value of S3+T2 and the variable S4 is initialized as the old value of the variable S4+S3. In block A548 the variable T2 is set equal to T1 minus two terms. The first term is a constant times S4 and the second is a constant times S3+1. As was noted for the first two poles of the filter, blocks A546 and A548 implement equation (2) where a single summation (S3) is performed and a double summation (S4) is performed to implement the equation. In block A550 a gain correction factor for the output of the filter T2 is applied in much the same manner as was the gain correction factor for the first equation in block A544.

The square root of the output is taken in block A552 and the result stored at the address pointed to by the pointer Pc. The program continues in this loop by incrementing the variable CNT by one, the pointer Pb by INC4, and the pointer Pc by INC before returning to the decision block A538. Thereafter, the loop continues until the first half or the last half of the input vector is filtered by the routine. At the end of the test when the negative branch is taken from block A538 the output vector Vecb contains the results of the filtered data.

Figure 22:
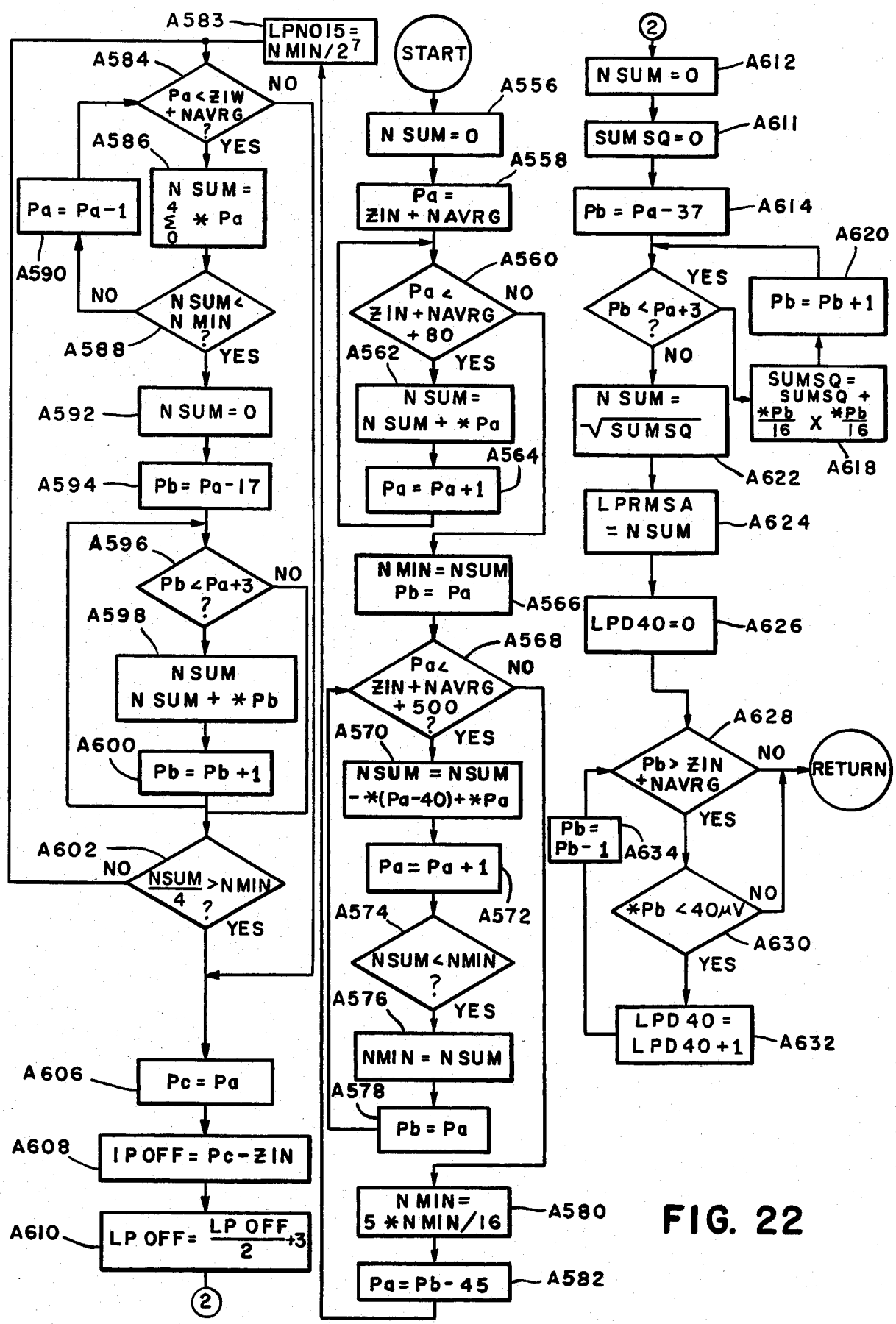
FIG. 22 is a detailed flow chart of the routine LATEP which is called from the routine PLOT illustrated in FIG. 13.

FIG. 22 is the detailed flow chart for the routine LATEP which calculates the root mean square (RMS) level of the "late potentials" during the last 40 millisecs of the QRS-segment and further calculates the the time in millisecs, that the "late potentials" exceed 40 microvolts. These two calculated values can then be used to inform a doctor of the relative amplitude of the "late potentials" and their duration. To predict ventricular tachycardia or other functions, these numbers an be compared with empirical reference levels developed through studies as described in the reference to Simpson. The two calculations are performed by the routine LATEP and are output to the plotter by the routine PLOT which calls the "late potentials" algorithm as a subroutine. Additionally, a noise level calculation for the "late potentials" duration is performed.

The routine initiates at block A556 where the variable NSUM is set equal to 0. Thereafter, the next forty samples after the peak (ZIN+NAVRG) of the composite waveform are summed in blocks A558-A564 to obtain a noise estimate. Thereafter, this forty sample length interval is translated to the end of the QRS-segment by adding the latest sample amplitude to the sum and subtracting the earliest in blocks A566-A572. This translation continues until the test in blocks A568 is failed where the forty sample interval has been translated to a final point of 250 samples after the peak of the composite waveform.

During the translation, blocks A574-A578 constantly test the sum to determine whether it is less than the previous sum. If it is the address of the last sample of the sum (Pointer Pa) is stored as the pointer Pb in block A578. When the test condition in block A568 is failed, the pointer Pb contains the address of the last sample of the minimum of the forty sample sums and the variable NMIN contains the value of the minimum sum.

Thereafter, the minimum sum NMIN is averaged and scaled in blocks A580 and the pointer Pa set equal to a sample position five samples preceding the minimum forty sample sum in block A582. The average noise level in the minimum forty sample interval is then scaled by division with a constant in block A583 to provide the plotter with a value for the variable LPNOIS. This variable contains the average value of the noise level in the sample interval measured in units of tenths of microvolts.

The next part of the routine finds the "late potentials" termination from this information. In block A586 the sum of five samples (NSUM) is formed starting at Pa and then compared to the average noise level (NMIN) in block A588. If this sum is not greater than the average noise level then the pointer Pa is decremented in block A590 and the next sum formed. The loop moves the sum NSUM backwards in increments of one sample toward the peak of the composite waveform (ZIN+NAVRG) until it is greater than the average noise.

At this point the routine has decided that the sum NSUM may no longer be noise and thus may be the termination of the late potentials. To provide an additional check, the routine takes the sum of twenty samples in blocks A592-A600 where seventeen samples are previous to pointer Pa and three are subsequent. If the termination of the "late potentials" has been found the summation of the potentials in samples previous to the termination should make this sum much greater than the noise level. Therefore, the twenty sample sum (NSUM) is divided by 4 before being tested against the noise level NMIN in block A602.

If NSUM/4 is greater than NMIN the program assigns the sample pointed to by Pa as termination of the "late potentials". Blocks A606-A610 provide a transformation from an address into a sample time for the termination point labeled LPOFF. Next the square root of the sum of the squares is calculated for forty samples previous to the "late potentials" termination in blocks A612-A624. The samples have addresses ranging from Pb−37 to Pb+3 as illustrated by the starting condition in block A614 and the ending condition in block A616. The value of the variable LPRMSA is output to the plotter after being set equivalent to the RMS value for the forty samples preceding "late potential" termination.

In block A626-A634 the calculation for the duration the "late potentials" which are less than 40 microvolts is made. The calculation is made by starting at the sample pointed to by Pb in block A630 and testing its value to see whether it is less than 40 microvolts. If it is, the loop continues by incrementing variable LPD40 in block A632 and decrementing Pb in block A634. The loop threfore counts the number of samples which have an amplitude of less than 40 microvolts until the test condition in block A630 is failed. At that time the variable LPD40 contains the duration of all those samples and can be output to the plotter.

Figure 23:
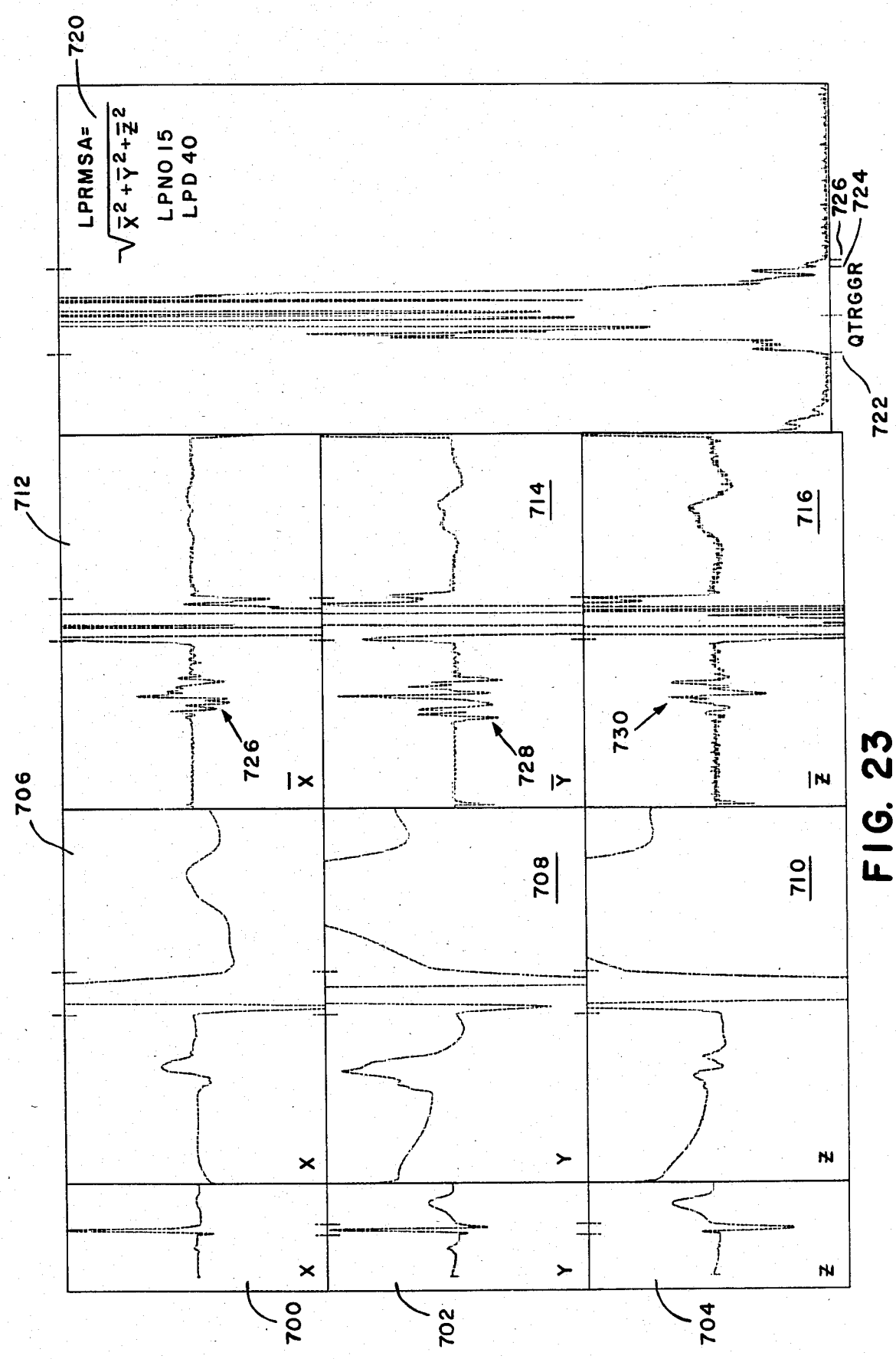
FIG. 23 is a pictorial composite of the output waveforms of the waveform processor illustrated in FIG. 1.

FIG. 23 illustrates the output of the routine PLOT for the commands developed at the CRT terminal. Waveforms in blocks 700, 702, and 704 represent the wideband signal which is measured from terminal X, Y, and Z. Blocks 706, 708, and 710 illustrated these waveforms on a magnified scale. Blocks 726, 728, and 730 illustrate the composite X, Y, and Z waveforms after they have been filtered with a finite impulse response (FIR) filter. The features 726, 728, 730 which stand out are at the locations where the His bundle potentials are generally found. Block 720 illustrate the result of forming composite X, Y, and Z leads and then reverse and forward filtering each lead with a 4 pole Butterworth filter. The resultants were squared, added together and the square root taken of the summation. It is seen that onset 722 and termination 724 of the waveform predominate.

While the present invention has been illustrated and described in conjunction with various preferred embodiments thereof, it is to be understood that numerous changes and modifications may be made thereto without departing from the spirit and scope of the present invention as is recited in the following appended claims.

There follows a detailed listing for the program which controls the operation of the system with the main processor 206.

```
/* hrcom.h -- common global declarations for signal averaging program */
#include <hrper.h>
#define size(vec) (sizeof(vec)>>1)

#define NLD 3
#define NRAW 2500
#define NFLT 75
#define NRHY 2500
#define NAVRG 800
define QTRGGR 100 int iqvec[8];                /* interrupt vectors */
short rcvira[8];             /* interrupt counters */
struct {
        short zin[4*NLD];    /* 4 input samples for 3 leads each 4ms */
        short zfd[NLD];      /* detection filter input */
        short zfm[NLD];      /* match filter input */
        unsigned short lfail; /* lead fail bits */
        unsigned char pflag;  /* pacemaker flag */
        unsigned char clock;  /* clock failure (no input) if = 0 */
} zbuf[400], *pzbi, *pzbo;    /* input buffer with in & out pointers */
```

```
int zbar [4*NAVRG];              /* average cycles for NLD leads */
short zin [NLD*NRAW];            /* 2 second input buffer for all leads */
short zrhy[NLD*NRHY];            /* 250Hz sampling rate rhythm buffer */
struct {
        short dtct [NLD*NFLT];   /* detection filter for 3 leads */
        short mtch [NLD*NFLT];   /* qrs match filter for 3 leads */
        } zflt;
short zac[2*8*NLD];              /* ac interference filter output */
unsigned char oplot[250];        /* output to plotter buffer */
unsigned char trmrcv[250], trmxmt[250]; /* terminal rcv & xmt buffers */
short *pzflt;                    /* pointer to zflt current index */
short *pzin;                     /* pointer to zin current index */
int *pzbar;                      /* pointer to zbar current index */
short *pzraw;                    /* pointer to zin in use by avrs */
short *pzrhyi, *pzrhyo;          /* in & out rhythm buffer pointers */
unsigned char *poplot;           /* plot buffer pointer */
unsigned char *prcvi, *prcvo;    /* terminal rcv buffer in & out ptrs */
unsigned char *pxmti, *pxmto;    /* treminal xmt buffer in & out ptrs */
int time ;                       /* time measured in 4ms units */
int nqrs ;                       /* number of qrs's detected */
int nqtyp ;                      /* number of qrs shapes observed */
int rr16;                        /* sum of last 16 rr intervals */
unsigned int rawzn[NLD], avzn[NLD]; /* noise levels in input & average */
struct {
        short tmplt[2*NLD];      /* qrs template (2 points * 3 leads) */
        int qcnt;                /* count of occurences of this qrs */
        } qrs[8];                /* structure for qrs type data */
struct {
        int sum, dif, ratio, time, typ;
        int power, pkpwr, pktime, mnpwr;
        int rr, adj;
        } qrsv;                  /* qrs detection scalar variables */
struct {
        int rtime;               /* qrs trigger time */
        int rrint;               /* preceding rr interval */
        int pkamp;               /* peak amplitude from dectection */
        int qtyp;                /* qrs type */
        int avtyp;               /* qrs type for averaging purposes */
        short *pcycle;           /* cycle start pointer */
        int *pzbari;             /* cycle begin */
        } qrslst[16], *pqrsa, *pqrsb; /* including input (a) and output (b) list point
ers */
int qon, qoff;                   /* qrs onset & offset pointers (4ms) */
unsigned int pltmag;             /* scaling factor for plots */
char ostr[20];                   /* output string temporary */
char namdat[80];                 /* name/date/id string */
int lpoff;                       /* late potential offset time */
int lprmsa;                      /* late potential rms amplitude (40ms) */
int lpd40;                       /* late potential duration under 40uv */
int lpnois;                      /* late potential noise level */
short *paccon;                   /* AC filter contant pointer */
int pltrhy;                      /* flag for standard rhythm plot */
char tdata;                      /* last meaningful terminal input */
/* hires.c */
include <hrcom.h> main()
{
register short *pb, *pc, *ps;
int start(), ampirq(), pltirq(), trmirq();
```

```
/*AC constants are (2**15) * cos (delta) and delta is phase change in 1ms */
static short accon[14] {18409, 23887, 13952, -10126, -20887, -28715, 2058,\
                        12830, 26510, 19261,     0, -10126, -19261, 10126};
char *mkasc();

rcvira[8] = 0, xfrm (rcvira+8, rcvira+9, 0x10000);
pplot = oplot, pzrhy = zrhy-3;
if (iravec[3] != pltira) iravec[3] = pltira;
rcvira[3] = 0, pio.csr = 3, pio.csr = 0x91;

pxmti = trmxmt, pxmto = trmxmt, prcvi = trmrcv, prcvo = trmrcv;
if (iravec[7] != trmira) iravec[1] = trmira;
tio.csr = 3, tio.csr = 0x95;
tio.data = '\005';
for ( ; tdata == 0; ) ;
if (tdata == ' ') paccon = accon; else paccon = &accon[7];

pzbi = zbuf, pzbo = zbuf-1;
pzin = zin, pzflt = zflt.dtct;
arsv.mnpwr = 2500;

for (pb = arslst; pb < arslst+16; pb += size(arslst[0])) pb->avtyp = -1;
parsa = arslst, parsb = arslst, arslst.avtyp = -1;

if (iravec[4] != ampira) iravec[4] = ampira;
rcvira[4] = 0, rcvio.cmd.byte = 0x1e;

for (; time < 200; time++)
        setsmpl();
arsv.time = 167;
aon = (QTRGGR - 10)<<2, aoff = (QTRGGR + 10)<<2;
pltmag = 320;
prcvo = prcvi;

idisp();
xmit ("\033[24;1HCopyright 1983, ART.  All rights reserved.");
for (;;)
        {
        if (prcvi != prcvo)
                {
                prcvo = prcvi;
                if (tdata == '9') start();
                else if (tdata == '7')
                        pltrhy = 1, rhyplt(0), resynch();
                else if (tdata == '4')
                        pltrhy = 0, higain(), resynch();
                else if (tdata == '3')
                        plot(), resynch();
                else if (tdata == '6') pltmag <<= 1;
                else if (tdata == '5') pltmag >>= 1;
                else if (tdata == '1')
                        enterid(), resynch();
                else if (tdata == '\004')
                        dump(), resynch();
                }
        for ( ;tdata == '2'; )
                if (arsdct() == 0)
                        {
                        synch();
```

```
                        rhythm();
                        disply();
                        }
                parsb->svtyp = 10;
                if ((time20off) == 0) disply();
                time++, getsmpl();
                }
} enterid()
{
register unsigned char *pb;

xmtt ("\033[23;1HEnter name/ID/date free-form on next line (end with 'RETURN').");
xmtt ("\r\n\033[2K");

for (pb = namdat; pb < namdat+79; pb++)
        {
        for ( ; prcvi == prcvo; ) ;
        prcvo = prcvi;
        *pb = tdata;
        if (*pb == '\r') break;
        if (*pb <= '\037')
                {
                pb--;
                continue;
                }
        if (*pb == 0x7f && pb > namdat)
                xmtt ("\010 \010"), pb -= 2;
        else tio.data = *pb;
        }
*pb = 0;
xmtt ("\033[23H\033[2K");
return;
} resynch()
{
register int n;
rcvira[4] = 0;
for ( ; rcvira[4] == 0; ) ;

pzbi = zbuf, pzbo = zbuf-1, pzin = zin, pzflt = zflt.dtct;
rcvira[4] = 0;

for (n = 0; n < 625; n++)
        time++, getsmpl();

xmtt ("\007");
return;
} dump()
{
register unsigned char *pa;
char messs[3];
```

```c
mess[2] = 0;

xmtr ("\033.Z\001");
xmtr (namdat);
for ( xmtr ("\002"); pa = zbar; pa < zbar+4*NAVRG; pa++)
        {
        messs[0] = (*pa>>4) + 'A', messs[1] = (*pa & 0xf) + 'A';
        xmtr (messs);
        }
xmtr ("\033.Y");
return;
}
/* hrdct.c */
#include <hrcom.h>
define AMIN 1200               /* detection threshold ( unit = 2 microvolt) */ arsdct()
{
register short *pb, *pc, *ps;
int abamp, nbis, sum, dif1, dif2, atyp;
short ztmp[2*NLD*3];

arsv.rr = time - arsv.time - 13;
arsv.dif = 30000, arsv.ratio = 30000, arsv.pkpwr = 0, arsv.pktime = 0;
arsv.typ = natyp;
for ( ; rcvirg[4] > 350; )
        time++, arsv.rr++, setsmpl ();
for ( ; ; )
        {
        time++, arsv.rr++;
        setsmpl ();
        if (arsv.rr < 40) continue;
        if (tdata != '2' && arsv.rr > 250) return 1;
        if ((arsv.rr&0xf) == 0)
                arsv.mnpwr -= (arsv.mnpwr - AMIN/2)>>4;

pb = &pzflt->dtct;
        arsv.power = iabs (*pb++) + iabs (*pb++) + iabs (*pb++);
        if (arsv.pkpwr == 0 && arsv.power >= arsv.mnpwr) arsv.pkpwr = arsv.power;
        if (arsv.pkpwr != 0)
                {
                xfrtpt (pb-11*NLD, ztmp);
/*              for (atyp = 0; ps = ars.tmplt; atyp < natyp; atyp++, ps+=size(ars[0]))
                        {
                        if (arsv.ratio < 150 && atyp > arsv.typ) break;
                        sum = 0, dif1 = 0;
                        for (pb = ztmp, pc = ps; pb < ztmp+2*NLD; )
                                {
                                sum += iabs(*pc + *pb);
                                dif1 += iabs(*pc++ - *pb++);
                                }
                        match (dif1, sum, atyp);
                        }
*/              match (ztmp);

if (arsv.power > arsv.pkpwr)
                        arsv.pkpwr = arsv.power, arsv.pktime = 0;
```

```
            else arsv.pktime++;
            }
        if (arsv.pktime >= 20) break;
        } arsv.mnpwr = (arsv.mnpwr + arsv.pkpwr)>>1;
if (arsv.mnpwr > 2*AMIN) arsv.mnpwr = 2*AMIN;
if (notyp == 0) arsv.time = time - 10;
if (rcvira[4] > 300) arsv.ratio = 1000;

ps = &ars[arsv.typ].tmplt;
pb = &pzflt->dtct[(arsv.time - time - 10)*NLD];
xfrtpt (pb, ztmp);

if (arsv.ratio >= 150)
        if (notyp < 3)
                {
                arsv.time = time - 10;
                arsv.typ = notyp++;
                xfrtpt (&pzflt->dtct[-NLD*20], &ars[arsv.typ].tmplt);
                }
        else arsv.typ = 2;

arsv.rr -= time - arsv.time + 10;
if (nars == 0) arsv.rr = 200;
nars++;

arsv.time -= 23;
return 0;
}
xfrtpt (p1, p2)
short *p1, *p2;
{
register short *pb, *pc, *pd;

pb = p2;

pc = p1 - zflt.dtct + zflt.mtch - 10*NLD; if (pc < zflt.mtch) pc += NFLT*NLD;
pd = pc + 8*NLD; if (pd >= &zflt.mtch[NFLT*NLD]) pd -= NFLT*NLD;
*pb++ = *pc++ + *pd++; *pb++ = *pc++ + *pd++; *pb++ = *pc++ + *pd++;

pc += 11*NLD; if (pc >= &zflt.mtch[NFLT*NLD]) pc -= NFLT*NLD;
pd = pc + 8*NLD; if (pd >= &zflt.mtch[NFLT*NLD]) pd -= NFLT*NLD;
*pb++ = *pc++ + *pd++; *pb++ = *pc++ + *pd++; *pb++ = *pc++ + *pd++;

return;
}
/* hrrhym.c */
include <hrcom.h> rhythm()
{
register short *pb, *pc;
register int *pbar;

pbar = 0;
pc = parsb;
pb = pc + size(arslst[0]); if (pb >= arslst+16) pb = arslst;
```

```
if (arsv.typ!=0 && arsv.rr<=45)
        if (pc->atyp==0 || arsv.pkpwr<pc->pkamp)
                {
                arsv.time = pc->rtime; nars--;
                return;
                } if (pc->atyp!=0 && arsv.pkpwr > pc->pkamp && (arsv.rr<=45 || (arsv.rr<=75 && arsv.typ==0
)))
        {
        arsv.rr += pc->rrint; pc->rtime -= rr16; nars--;
        pb = pc;
        } if (nars>2 && nars<8 && arsv.typ!=0 && arsv.rr>=rr16>>4)
        {
        nars = 2;
        xfrm (&ars[arsv.typ].tmplt, &ars[0].tmplt, 18);
        arsv.typ = 0;
        natyp = 1;
        for (pbar = zbar; pbar < zbar+4*NAVRG; ) *pbar++ = 0;
        } ars[arsv.typ].acnt++;

if (nars <= 16)
        rr16 = arsv.rr<<4;
else rr16 = arsv.time - pb->rtime;

pb->rtime = arsv.time;
pb->rrint = arsv.rr;
pb->pkamp = arsv.pkpwr;
pb->atyp = arsv.typ;
if (arsv.rr+25 > rr16>>4) pb->avtyp = arsv.typ; else pb->avtyp = -1;

pbar = zbar + (QTRGGR<<4) - ((rr16>>3)<<2);
if (pbar < zbar) pbar = zbar;
pb->pzbari = pbar;

pc = zin - (((time - arsv.time + QTRGGR)<<2) - ((pbar - zbar)>>2) - arsv.adj)*NLD;
if (pc < zin) pc += NRAW*NLD;
pb->pcycle = pc;
parsb = pb;

return;
}

/* hrset.c */
#include <hrcom.h>
extern int next, last;

setsmpl ()
{
register short *pz, *pb, *pc;
short *pd;
char *makasc();

for ( ; rcvirq[4] == 0; ) ;
rcvirq[4]--;
```

```
pz = pzin+NLD*4; if (pz >= zin+NLD*NRAW) pz = zin; pzin = pz;
pb = pzbo+1; if (pb >= zbuf+400) pb = zbuf; pzbo = pb;
pc = pzflt+NLD; if (pc >= zflt.mtch) pc = zflt.dtct; pzflt = pc;

if (pb == pzbi) rawzn[0] = 8000;

avrg();

for (pd = pc+NLD; pc < pd; pc++)
        {
        pc->mtch[0] = pb->zfm[0];
        pc->dtct[0] = pb->zfd[0];
        *pz++ = *pb++;
        }
for (pc = pz+3*NLD; pz < pc; ) *pz++ = *pb++;

acflt();

if (pzrhyo == 0)
        {
        pz = pzrhyi+NLD; if (pz >= zrhy+NLD*NRHY) pz = zrhy; pzrhyi = pz;
        for (pb = pzin, pc = pz+3; pz < pc; pb++)
                *pz++ = (*pb + *(pb+3) + *(pb+6) + *(pb+9))>>2;
        }
else if (rcvira[3] < 50)
        {
        pz = pzrhyo;
        if (pz == pzrhyi-1)
                {
                pz++, rhybas (0), next = 0;
                xmtp ("SF1IW0,4500,10300,6750PUPA120,5625PDPR");
                }
        else if (pz == pzrhyi)
                {
                pz++, rhybas (1), next = 0;
                xmtp ("IW0,2250,10300,4500PUPA120,3375PDPR");
                }
        else if (pz == pzrhyi+1)
                {
                pz++, rhybas (2), next = 0;
                xmtp ("IW0,0,10300,2250PUPA120,1125PDPR");
                }
        else if (pz == pzrhyi-4 || tdata == '8')
                {
                pzrhyo = 0;
                xmtp ("IWPUPA10120,0PDPR0,6750,-10120,0,0,-6750,10120,0FU");
                xmtp ("PR0,2250PD-10120,0PU0,2250PD10120,0PUPA0,0SP;");
                for ( ; rcvira[3] != 0; ) ;
                return;
                } pz += NLD; if (pz >= zrhy+NLD*NRHY) pz -= NLD*NRHY; pzrhyo = pz;
        last = next, next = (*pz * pltmas), next /= 1920;
        if (next > 11000) next = 11000;
        else if (next < -11000) next = -11000;

xmtp (",4,"), xmtp (makasc (next-last, ostr+19));
        } pz = pzin;
```

```
if (iabs(*pz - (*(pz-12)<<1) + *(pz-24)) >= rawzn[0]>>5)
        rawzn[0]++; else rawzn[0]--;
if (iabs(*(pz+1) - (*(pz-11)<<1) + *(pz-23)) >= rawzn[1]>>5)
        rawzn[1]++; else rawzn[1]--;
if (iabs(*(pz+2) - (*(pz-10)<<1) + *(pz-22)) >= rawzn[2]>>5)
        rawzn[2]++; else rawzn[2]--;
return;
} rhybas ()
{
register short *pz;
register int sum;

if (pitshi == 0) return;

pz = zrhy + ld;
for (sum = 0; pz < zrhy+160*NLD; pz += 10*NLD) sum += *pz;
for (sum >>= 4, pz = zrhy + ld; pz < zrhy+NLD*NRHY; pz += NLD) *pz -= sum;
return;
}
/* disply.c */
include <hrcom.h> idisp()
{ xmtt ("\033[2J\033[2J\033[2;1H\033#4\033M\033#3");
xmtt ("  RATE            COUNT\n\r");
xmtt ("  RATE            COUNT\n\r");

xmtt ("\n\033#6          Noise (uV)\n\r");
xmtt ("\033#6      Input      Average      Scale\n\r");
xmtt ("\033#6  \033[7m                                  \033[m\n\r");
xmtt ("\033#6X \033[7m \033[m          \033[7m \033[m          \033[7m \033[m         x\n\r");
for ( ; pxmti != pxmto ; ) ;
xmtt ("\033#6  \033[7m                                  \033[m\n\r");
xmtt ("\033#6Y \033[7m \033[m          \033[7m \033[m          \033[7m \033[m\n\r");
xmtt ("\033#6  \033[7m                                  \033[m\n\r");
xmtt ("\033#6Z \033[7m \033[m          \033[7m \033[m          \033[7m \033[m\n\r");
xmtt ("\033#6  \033[7m                                  \033[m\n\r");
for ( ; pxmti != pxmto ; ) ;

xmtt ("\nDepress corresponding numeric key to:\r\n\n");
xmtt ("1. Enter ID         4. Plot high gain    7. Plot rhythm\n\r");
xmtt ("2. Average          5. Decrease gain     8. Stop\n\r");
xmtt ("3. Plot average     6. Increase gain     9. Reset");
for ( ; pxmti != pxmto ; ) ;

xmtt ("\033[20;24r\033[20;1H");
return;
} disply()
{
register char *pb;
register short *pc;
```

```
register int count;
char *makasc(), *ascdec();

ostr[18] = ' ', ostr[17] = ' ';
if (rr16 != 0)
        {
        pb = makasc (240000/rr16, ostr+17);
        xmtt ("\033[1;8H"), xmtt (pb);
        xmtt ("\033[2;8H"), xmtt (pb);
        }
pb = makasc (zbar[2*NAVRG+3], ostr+17);
xmtt ("\033[1;26H"), xmtt (pb);
xmtt ("\033[2;26H"), xmtt (pb);

pc = pzbo;
xmtt ("\033[7;8H");
if ((pc->lfail&0xc0) == 0) xmtt (ascdec (rawzn[0]>>3, 1, ostr+17));
else xmtt ("FAIL");

xmtt ("\033[9;8H");
if ((pc->lfail&0x18) == 0) xmtt (ascdec (rawzn[1]>>3, 1, ostr+17));
else xmtt ("FAIL");

xmtt ("\033[11;8H");
if ((pc->lfail&0x22) == 0) xmtt (ascdec (rawzn[2]>>3, 1, ostr+17));
else xmtt ("FAIL");

xmtt ("\033[13;1H");
if (pc->lfail != 0)
        {
        xmtt ("Missing leads: ");
        if ((pc->lfail&0x80) != 0) xmtt ("X+ ");
        if ((pc->lfail&0x40) != 0) xmtt ("X- ");
        if ((pc->lfail&0x8)  != 0) xmtt ("Y+ ");
        if ((pc->lfail&0x10) != 0) xmtt ("Y- ");
        if ((pc->lfail&0x20) != 0) xmtt ("Z+ ");
        if ((pc->lfail&0x2)  != 0) xmtt ("Z-");
        }
xmtt ("\033[K");

if (zbar[2*NAVRG+3] != 0)
        {
        count = zbar[2*NAVRG+3]<<2;
        xmtt ("\033[7;18H"), xmtt (ascdec ((5*avzn[0])/count, 2, ostr+17));
        xmtt ("\033[9;18H"), xmtt (ascdec ((5*avzn[1])/count, 2, ostr+17));
        xmtt ("\033[11;18H"), xmtt (ascdec ((5*avzn[2])/count, 2, ostr+17));
        }
xmtt ("\033[9;34H");
if (pltmag < 320)
        xmtt ("1/"), xmtt (makasc (320/pltmag, ostr+17));
else xmtt (makasc (pltmag/320, ostr+17));

xmtt ("\033[20;1H");
return;
}

/* hrplot.c */
#include <hrcom.h>
```

```
plot()
{
register int *pbar, ld;
char *makasc();
int nqrs, nqrs3, offset[3], x10, d10;

nqrs = zbar[(QTRGGR<<4)+3];
if (nqrs == 0) return;

nmlz ();
pbar = zbar + (qon<<2);
offset[0] = *pbar++, offset[1] = *pbar++, offset[2] = *pbar++;

for (pbar = zbar; pbar < zbar+4*NAVRG; )
        {
        *pbar++ -= offset[0], *pbar++ -= offset[1], *pbar++ -= offset[2];
        if (*pbar++ < nqrs>>1)
                *(pbar-4) = 0, *(pbar-3) = 0, *(pbar-2) = 0, *(pbar-1) = 0;
        } pltbes();
x10 = 10*pltmas, d10 = pltmas/10;

xmtp ("SP1IW0,4500,7320,6750PUPA120,5625PD");
pltld (zbar, 4, NAVRG, "1", d10), xmtp ("PA920,5625");
pltld (zbar, 4, NAVRG, "4", pltmas), xmtp ("PA4120,5625");
firflt (zbar, zin), pltld (zin, 1, NAVRG, "4", x10);

xmtp ("IW0,2250,7320,4500PUPA120,3375PD");
pltld (zbar+1, 4, NAVRG, "1", d10), xmtp ("PA920,3375");
pltld (zbar+1, 4, NAVRG, "4", pltmas), xmtp ("PA4120,3375");
firflt (zbar+1, zin), pltld (zin, 1, NAVRG, "4", x10);

xmtp ("IW0,0,7320,2250PUPA120,1125PD");
pltld (zbar+2, 4, NAVRG, "1", d10), xmtp ("PA920,1125");
pltld (zbar+2, 4, NAVRG, "4", pltmas), xmtp ("PA4120,1125");
firflt (zbar+2, zin), pltld (zin, 1, NAVRG, "4", x10);

zin[0] = 0, xfrn (zin, zin+1, 4*NAVRG-2);
butflt (zbar, zin, 1), butflt (zbar+4*NAVRG-4, zin+2*(NAVRG-1), -1);
butflt (zbar+1, zin, 1), butflt (zbar+4*NAVRG-3, zin+2*(NAVRG-1), -1);
butflt (zbar+2, zin, 1), butflt (zbar+4*NAVRG-2, zin+2*(NAVRG-1), -1);

xmtp ("IW0,100,10300,6750PUPA7320,100PD");
pltld (zin+550, 1, 375, "8", x10);

later();
xmtp ("PA120,4500PDPR7200,0PU0,-2250PD-7200,0PU");

xmtp ("PA"), xmtp (makasc (120 + qon, ostr+19));
xmtp (",4600PDPR0,-200PU0,-2050PD0,-200PU");
xmtp ("PA"), xmtp (makasc (120 + qoff, ostr+19));
xmtp (",2150PDPR0,200PU0,2050PD0,200PU");

xmtp ("PA"), xmtp (makasc (920 + (qon<<2), ostr+19));
xmtp (",6850PDPR0,-200PU0,-2050PD0,-200PU0,-2050PD0,-200PU");
```

```
xmtp ("PA"), xmtp (makasc (920 + (aoff<<2), ostr+19));
xmtp (",2150PDPRO,200PUO,2050PDO,200PUO,2050,PDO,200PU");

xmtp ("PA"), xmtp (makasc (4120 + (aon<<2), ostr+19));
xmtp (",6850PDPRO,-200PUO,-2050PDO,-200PUO,-2050PDO,-200PU");
xmtp ("PA"), xmtp (makasc (4120 + (aoff<<2), ostr+19));
xmtp (",2150PDPRO,200PUO,2050PDO,200PUO,2050,PDO,200PU");

xmtp ("PA"), xmtp (makasc (5120 + (aon<<3), ostr+19));
xmtp (",6850PDPRO,-200PUO,-6550PDO,-100PU");
xmtp ("PA8320,200PDPRO,-200PUPA");
xmtp (makasc (5120 + (lpoff<<3), ostr+19)), xmtp (",0PDPRO,100PUPA");
xmtp (makasc (5120 + (aoff<<3), ostr+19));
xmtp (",0PDPRO,100PUO,6550PDO,200PU");

xmtp ("SF2PA40,6500LBDC-250Hz\r\n25mm/s\r\n");
xmtp (ascdec (x10>>5, 1, ostr+19)), xmtp ("mm/mV\003");
xmtp ("PA960,6500LBDC-250Hz\r\n100mm/s\r\n");
xmtp (ascdec (pltmas>>5, 2, ostr+19)), xmtp ("mm/uV\003");
xmtp ("PA4160,6500LB50-250Hz\r\n100mm/s\r\n");
xmtp (ascdec (x10>>5, 2, ostr+19)), xmtp ("mm/uV\003");
xmtp ("PA7360,6500LB40-250Hz\r\n200mm/s\r\n");
xmtp (ascdec (x10>>5, 2, ostr+19)), xmtp ("mm/uV\r\n");
xmtp ("\nVector\r\nMagnitude\003");
xmtp ("PA9100,6500LBQRSD "), xmtp (makasc (aoff-aon, ostr+19));
xmtp ("ms\r\nHFTD "), xmtp (makasc (lpoff-aon, ostr+19));
xmtp ("ms\r\nHFD40 "), xmtp (makasc (lpd40, ostr+19));
xmtp ("ms\r\nHFRMSA "), xmtp (ascdec (lprmsa, 1, ostr+19));
xmtp ("uV\r\nHFNOIS "), xmtp (ascdec (lpnois, 1, ostr+19));
xmtp ("uV\003");

xmtp ("SIPUPAO,OSP;");

for (pbar = zbar; pbar < zbar+4*NAVRG; )
        {
        nars3 = 3 * *(pbar+3);
        for (ld = 0; ld < 3; ld++)
                *pbar++ = (((*pbar & 0x7f) * nars3) >>7) + (*pbar >> 7) * nars3;
        pbar++;
        }
for ( ; revirg[3] != 0; ) ;
    return;
    }
register int *pb, *pc, *pd;

for (pc = vecb, pd = pc + 7; pc < pd; ) *pc++ = 0;
for (pb = veca, pd = pc + NAVRG - 15; pc < pd; pb += 4, *pc++ = 0)
        if (*pb != 0) break;

for ( ; pc < pd; pb += 4)
        *pc++ = (((*(pb+7*4) + *(pb+8*4))<<3) - *pb - *(pb+4) - *(pb+2*4) -\
                *(pb+3*4) - *(pb+4*4) - *(pb+5*4) - *(pb+6*4) - *(pb+7*4) -\
                *(pb+8*4) - *(pb+9*4) - *(pb+10*4) - *(pb+11*4) - *(pb+12*4) -\
                *(pb+13*4) - *(pb+14*4) - *(pb+15*4))>>4;
for (pd = pc + 8; pc < pd; ) *pc++ = 0;
return;
}
```

```
butflt (veca, vecb, inc)
int veca[], vecb[];
{
register int *pb, *pc, cnt;
int s1, s2, s3, s4, t1, t2, inc4;

inc4 = inc<<2;
pb = veca; pc = vecb;
for (cnt = 0; cnt < NAVRG>>1; cnt++, pb += inc4, pc += inc)
        if (*pb != 0) break;

s2 = *pb<<4;
s1 = 0, t1 = 0, s3 = 0, s4 = 0, t2 = 0;

for ( ; cnt < NAVRG>>1; cnt++, pb += inc4, pc += inc)
        {
        s1 += t1;
        s2 += s1;
        t1 = *pb - ((s2 + ((59*s1)>>3))>>4);
        t1 -= (t1 + (t1<<1))>>4;
        s3 += t2;
        s4 += s3;
        t2 = t1 - ((s4 + s3 + (s3<<1))>>4);
        t2 -= (t2 + (t2<<1))>>5;
        *pc = sqrt(*pc, t2);
        }
return;
} plt1d (ivec, inc, n, px, scale)
char *px;
int ivec[];
{
register int *pb, *pc, cnt;
int next, last;
char *makasc();

xmtp ("PR");
for (pb = ivec, cnt = n, next = 0; cnt > 0; pb += inc, cnt--)
        {
        if (tio.data == '8') return;
        last = next, next = (*pb * scale)>>13;
        if (next > 11000) next = 11000;
        else if (next < -11000) next = -11000;
        xmtp (","), xmtp (px), xmtp (",");
        xmtp (makasc (next-last, ostr+19));
        }
return;
} later()
{
register int *pa, *pb, nsum;
short *pc;
int nmin, sumsq, pass;
```

```
for (nsum = 0; pa = zin+NAVRG; pa < zin+NAVRG+80; ) nsum += *pa++;
for (nmin = nsum, pb = pa; pa < zin+NAVRG+500; )
        {
        nsum -= *(pa-40), nsum += *pa++;
        if (nsum < nmin)
                nmin = nsum, pb = pa;
        }
nmin = (5*nmin)>>4, pa = pb - 45;
lpnois = nmin>>7;

for ( ; pa > zin+NAVRG; pa--)
        {
        nsum = *pa + *(pa+1) + *(pa+2) + *(pa+3) + *(pa+4);
        if (nsum > nmin)
                {
                for (nsum = 0, pb = pa - 17; pb < pa + 3; ) nsum += *pb++;
                if (nsum>>2 > nmin) break;
                }
        } pc = pa, lpoff = pc - zin, lpoff = (lpoff>>1) + 3;
for (nsum = 0, sumsq = 0, pb = pa - 37; pb < pa + 3; )
        {
        sumsq += (*pb>>4) * (*pb>>4);
        nsum += *pb++>>4;
        }
nsum = nsum/25 + 1, sumsq >>= 4;
for (pass = 0; pass < 5; pass++) nsum = (sumsq/nsum + nsum)>>1;
lprmsa = nsum;          /* lprmsa is in tenths of microvolts */ for (lpd40 = 0; pb > zin+NAVRG && *pb < 2000; pb--) lpd40++;
return;
}

/* hrhis.c */
include <hrcom.h> hisain()
{
register short *pb, *pc, *pd;
short sum[NLD], dif;

for (pb = zin, pc = zrhy; pb < zin+NLD*NRAW; ) *pc++ = *pb++;

pb = pzin - zin + zrhy + NLD; if (pb >= zrhy+NLD*NRHY-NLD) pb -= NLD*NRHY-NLD;
pc = pb + 8*NLD; if (pc >= zrhy+NLD*NRHY-NLD) pc -= NLD*NRHY-NLD;
pd = pc + 8*NLD; if (pd >= zrhy+NLD*NRHY-NLD) pd -= NLD*NRHY-NLD;
pzrhyi = pb;

for (sum[0] = 0, sum[1] = 0, sum[2] = 0; pb != pd; )
        {
        sum[0] += *pb++, sum[1] += *pb++, sum[2] += *pb++;
        if (pb >= zrhy+NLD*NRHY-NLD) pb -= NLD*NRHY-NLD;
        } for (pb = pzrhyi; pd != pzrhyi; )
        {
```

```
        sum[0] += *pd++ - *pb; dif = ((*pc + *(pc+NLD))<<3) - sum[0];
        *pb++ = 25*dif>>2;
        pc++;
        sum[1] += *pd++ - *pb; dif = ((*pc + *(pc+NLD))<<3) - sum[1];
        *pb++ = 25*dif>>2;
        pc++;
        sum[2] += *pd++ - *pb; dif = ((*pc + *(pc+NLD))<<3) - sum[2];
        *pb++ = 25*dif>>2;
        pc++;
        if (pb >= zrhy+NLD*NRHY-NLD) pb -= NLD*NRHY-NLD;
        if (pc >= zrhy+NLD*NRHY-NLD) pc -= NLD*NRHY-NLD;
        if (pd >= zrhy+NLD*NRHY-NLD) pd -= NLD*NRHY-NLD;
        } for ( ; pb != pd; )
        {
        *pb++ = 0; *pb++ = 0; *pb++ = 0;
        if (pb >= zrhy+NLD*NRHY-NLD) pb -= NLD*NRHY-NLD;
        }
zrhy[NLD*NRHY-NLD] = zrhy[NLD*NRHY-2*NLD];
zrhy[NLD*NRHY-NLD+1] = zrhy[NLD*NRHY-2*NLD+1];
zrhy[NLD*NRHY-NLD+2] = zrhy[NLD*NRHY-2*NLD+2];

pzrhyi -= NLD;
rhyplt(1);
return;
}

{
char *ascdec();

pltbes();
if (flag == 0)
        {
        xmtp ("PA40,6500LBDC-250Hz\r\n25mm/s\r\n");
        xmtp (ascdec ((10*pltmag)>>5, 1, ostr+19)); xmtp ("mm/mV\003SP1");
        }
else    {
        xmtp ("PA40,6500LB50-250Hz\r\n100mm/s\r\n");
        xmtp (ascdec ((10*pltmag)>>5, 2, ostr+19)); xmtp ("mm/uV\003SP1");
        }
pzrhyo = pzrhyi - 1;
return;
} pltbes()
{ if (namdat[0] == 0)
        xmtt ("\007"); enterid();

xmtp ("\033.J;N\033.I127;;17;\033.N;19;IP0,0,10300,7650SI.14,.21\033.0");
for ( ; rcvirq[3] != 0; ) ;
if (pio.data) ;
pio.csr = 0x11;
for ( ; (pio.csr&1) == 0; ) ;
if (pio.data == '4' || pio.data == '3')
```

```
            {
            xmtt ("\007\033[23;1HPLEASE LOAD PAPER IN PLOTTER AND PRESS 'RETURN'.");
            for ( ; prcvi == prcvo; ) ;
            xmtt ("\033[2K");
            }
    xmtp ("SP2PA0,7560LB"); xmtp (namdat); xmtp ("\003");
    xmtp ("PUPA40,5700LBX\003PA40,3450LBY\003PA40,1200LBZ\003");
    return;
    }

/* hrmisc.c */
    #include <hrcom.h> xfin (pa, pb, n)
    char *pb, *pa;
    {
    register char *p1, *p2;
    register int cnt;

for (p1 = pa, p2 = pb, cnt = n; cnt > 0; cnt--) *p2++ = *p1++;
    return;
    } xmtt (data)
    char data[];
    {
    register unsigned char *pb, *pc;

for (pb = data, pc = pxmti; *pb != 0; )
            {
            *pc++ = *pb++;
            if (pc >= trmxmt+250) pc = trmxmt;
            }
    pxmti = pc;
    tio.csr = 0xb5;
    return;
    } xmtp (pchar)
    unsigned char *pchar;
    {
    register unsigned char *pb, *pc;
    register int count;
    int status;

if (tio.data == '8') return;

for (pb = pchar, pc = pplot; *pb != 0; )
            {
            for ( ; rcvira[3] >= 200; ) ;
            for (count = 0; count < 50 && *pb != 0; count++)
                    {
                    *pc++ = *pb++;
                    if (pc >= pplot+250) pc = pplot;
                    }
            status = setsr (0x2300);
```

```
            poplot = pc;
            rcvira[3] += count;
            setsr (status);
            }
pio.csr = 0xb1;
return;
}

.text
        .globl  _iabs,_max2,_max3,_min2,_min3,_makasc,_ascdec
        .globl  _pltira,_ampira,_zbuf,_pzbi,_rcvira,_rcvio,_pio
        .globl  _absdif,_nmlz,_zbar,_sqrt
        .globl  _match,_time,_natyp,_qrs,_qrsv
        .globl  _oplot,_poplot,_setsr
        .globl  _acflt,_zac,_pzin
        .globl  _trmira,_tio,_pxmto,_pxmti,_prcvi,_tdata
        .globl  _avrs,_z0,_pzbar,_pqrsb,_rr16,_avzn,_pzraw _iabs:  move.l  4(sp),d7
        bge.s   iabs1
        neg.l   d7
iabs1:  rts _max2:  move.l  4(sp),d7
        move.l  8(sp),d6
        cmp.l   d6,d7
        bge.s   max21
        move.l  d6,d7
max21:  rts _max3:  move.l  4(sp),d7
        move.l  8(sp),d6
        cmp.l   d6,d7
        bge.s   max31
        move.l  d6,d7
max31:  move.l  12(sp),d6
        cmp.l   d6,d7
        bge.s   max32
        move.l  d6,d7
max32:  rts _min2:  move.l  4(sp),d7
        move.l  8(sp),d6
        cmp.l   d6,d7
        ble.s   min21
        move.l  d6,d7
min21:  rts _min3:  move.l  4(sp),d7
        move.l  8(sp),d6
        cmp.l   d6,d7
        ble.s   min31
        move.l  d6,d7
min31:  move.l  12(sp),d6
        cmp.l   d6,d7
        ble.s   min32
        move.l  d6,d7
min32:  rts
```

```
_makacc:
        move.l  4(sp),d0
        move.l  d0,d6
        bpl.s   mka1
        neg.l   d0
mka1:   move.l  8(sp),a0
        movea.l #10,d1
mka2:   divu    d1,d0
        swap    d0
        add.w   #'0,d0
        move.b  d0,-(a0)
        clr.w   d0
        swap    d0
        bne.s   mka2
        tst.l   d6
        bpl.s   mka3
        move.b  #'-,-(a0)
mka3:   move.l  a0,d7
        rts _ascdec:
        move.l  4(sp),d0        * argument to be converted
        move.l  8(sp),d2        * digits after decimal point (count)
        move.l  d0,d6
        bpl.s   ascd1
        neg.l   d0
ascd1:  move.l  12(sp),a0       * last address ptr of string
        movea.l #10,d1
ascd2:  divu    d1,d0
        swap    d0
        add.w   #'0,d0
        move.b  d0,-(a0)
        suba.w  #1,d2
        bne.s   ascd3
        move.b  #'.,-(a0)
ascd3:  clr.w   d0
        swap    d0
        bne.s   ascd2
        tst.w   d2
        bpl.s   ascd2
        tst.l   d6
        bpl.s   ascd4
        move.b  #'-,-(a0)
ascd4:  move.l  a0,d7
        rts _match: move.l  4(sp),a2        * bandpass filter template for this time
        clr.l   d2              * atyp
        move.l  #_ars,a1        * ars.tmplt
mtch1:  cmp.w   _natyp+2,d2     * for (atyp=0;ps=ars.tmplt; atyp<natyp; atyp++,ps+=)
        bge     mtch6 cmp.w   #150,_arsv+10   * if(arsv.ratio<150 && atyp>arsv.typ) break;
        bcc.s   mtch0
        cmp.w   _arsv+18,d2
        bgt.s   mtch6
```

```
mtch0:  clr.l    d6              * sum = 0
        clr.l    d7              * dif = 0
        movea.l  #6,d1           * accumulate 6 items mtch2:  move.w   (a1),d0
        add.w    (a2),d0
        bpl.s    mtch3
        neg.w    d0
mtch3:  ext.l    d0
        add.l    d0,d6           * sum += iabs (*pc + *pb);
        move.w   (a1)+,d0
        sub.w    (a2)+,d0
        bpl.s    mtch4
        neg.w    d0
mtch4:  ext.l    d0
        add.l    d0,d7           * dif += iabs (*pc++ - *pb++);
        subq.w   #1,d1
        bne.s    mtch2 movea.l  #100,d0
        cmp.l    d0,d6           * if (sum < 100) return;
        blt.s    mtch5
        move.l   d7,d0
        asl.l    #8,d0
        asl.l    #2,d0
        divu     d6,d0           * ratio = (1024*dif)/sum;
        cmp.w    _arsv+10,d0     * if (ratio >= arsv.ratio) return;
        bcc.s    mtch5 move.l   d7,_arsv+4      * arsv.dif = dif;
        move.l   d6,_arsv        * arsv.sum = sum;
        move.l   d2,_arsv+16     * arsv.typ = atyp;
        move.w   d0,d1           * exploits upper half d1 = 0
        move.l   d1,_arsv+8      * arsv.ratio = ratio;
        move.l   _time,_arsv+12  * arsv.time = time;
        cmp.w    #150,d0         * if (ratio < 150) return;
        blt.s    mtch6 mtch5:  lea      -12(a2),a2      * ztmp
        lea      16(a1),a1       * ps += ...
        adda.w   #1,d2           * atyp++
        bra      mtch1
mtch6:  rts _setsr: clr.l    d7
        mfsr     d7
        mtsr     6(sp)
        rts _trmirq:
        btst     #0,_tio
        beq.s    trxmt
        cmp.b    #0x13,_tio+2
        bne.s    trcv1
        move.b   #0x95,_tio      * stop xmit on 'x-off'
        rte
```

```
trcv1:   cmp.b   #0x11,_tio+2
         bne.s   trcv2
         move.b  #0xb5,_tio              * re-enable xmt irq on "x-on"
         rte trcv2:   move.l  a0,-(sp)
         move.l  _prcvi,a0
         move.b  _tio+2,_tdata
         move.b  _tio+2,(a0)+
         cmp.l   #_trmrcv+250,a0
         bne.s   trcv3
         lea     -250(a0),a0
trcv3:   move.l  a0,_prcvi
         bra.s   trirqx trmxmt:  btst    #1,_tio
         beq.s   trirqz                  * xmt buffer not ready
         move.l  a0,-(sp)
         move.l  _pxmto,a0
         cmp.l   _pxmti,a0
         bne.s   trcv4
         move.b  #0x95,_tio              * disable irq if nothing to xmit
         bra.s   trirqx
trcv4:   move.b  (a0)+,_tio+2
         cmp.l   #_trmxmt+250,a0
         bne.s   trcv5
         lea     -250(a0),a0
trcv5:   move.l  a0,_pxmto
trirqx:  move.l  (sp)+,a0
trirqz:  rte _pltirq:
         btst    #0,_pio
         beq.s   pirq4                   * no input character
         cmp.b   #0x13,_pio+2
         bne.s   pirq3
         move.b  #0x91,_pio              * stop transmitting on receipt of x-off
         rte
pirq3:   cmp.b   #0x11,_pio+2
         bne.s   pirq4
         move.b  #0xb1,_pio              * reestablish transmit irq enable on x-on
pirq4:   btst    #1,_pio
         beq.s   pirqx                   * transmit buffer not ready
         tst.w   _rcvirq+6
         beq.s   pirq2                   * nothing to transmit
         cmp.b   #0x13,_pio+2
         beq.s   pirq2                   * do not xmit if plotter shows x-off
         move.l  a0,-(sp)
         move.l  _poplot,a0              * current buffer pointer (input to buffer)
         sub.w   _rcvirq+6,a0            * subtract count to get output pointer
         cmp.l   #_oplot,a0
         bcc.s   pirq1
         lea     250(a0),a0              * allowance for circular buffer
pirq1:   move.b  (a0),_pio+2             * transmit a new character
         subq.w  #1,_rcvirq+6            * decrement count of characters to xmit
         move.l  (sp)+,a0
pirqx:   rte
pirq2:   move.b  #0x91,_pio              * stop xmtr interrupts
         rte
```

```
_ampirq:
        adda.w  #1,_rcvirq+8           * count sample interrupts
        bpl.s   airq
        tst.b   _rcvio
        rte                            * ignore interrupts if count < 0 airq:   movem.l a0/a1/d0-d3,-(sp)
        move.l  _pzbi,a1
        move.l  #_rcvio+256,a0
        movea.l #64,d2
        movea.l #4,d3
airq1:  movep.l 0(a0),d0               *4 samples of input data
        move.l  d0,(a1)+
        movep.w 8(a0),d0
        move.w  d0,(a1)+
        adda.w  d2,a0
        suba.w  #1,d3
        bne.s   airq1 movep.w 0(a0),d0               *detection filter output
        movep.w 4(a0),d1
        sub.w   d1,d0                  * X = LA - LL
        move.w  d0,(a1)+
        movep.w 16(a0),d0
        movep.w 12(a0),d1
        sub.w   d1,d0                  * Y = V3 - V2
        move.w  d0,(a1)+
        movep.w 8(a0),d0
        movep.w 24(a0),d1
        sub.w   d1,d0                  * Z = V1 - V5
        move.w  d0,(a1)+ movep.w 32(a0),d0              *match filter output
        movep.w 36(a0),d1
        sub.w   d1,d0
        move.w  d0,(a1)+               * X = LA - LL
        movep.w 48(a0),d0
        movep.w 44(a0),d1
        sub.w   d1,d0
        move.w  d0,(a1)+               * Y = V3 - V2
        movep.w 40(a0),d0
        movep.w 56(a0),d1
        sub.w   d1,d0
        move.w  d0,(a1)+               * Z = V1 - V5 movep.w 104(a0),d0             *lead fail double byte
        move.w  d0,(a1)+ move.b  108(a0),(a1)+          *pacemaker flag byte
        move.b  102(a0),(a1)+          *clock error (if == 0)

cmp.l   #_zbuf+16000,a1
        bne.s   airq2
        lea     -16000(a1),a1
airq2:  move.l  a1,_pzbi
        movem.l (sp)+,a0-a1/d0-d3
        rte
```

```
_absdif:
        move.l  4(sp),a0        * a0 & a1 have addresses of vectors
        move.l  8(sp),a1        * the count of vector elements
        move.l  12(sp),d6       * the sum of absolute differences
        clr.l   d7 absd1:  move.w  (a0)+,d0
        sub.w   (a1)+,d0
        bpl.s   absd2
        neg.w   d0
absd2:  ext.l   d0
        add.l   d0,d7
        suba.w  #1,d6
        bne.s   absd1
        rts _nmlz:  move.w  #800,d6         * the size of zbar vector
        move.l  #_zbar,a0       * the vector address
nm1:    move.l  (a0),d0
        move.l  12(a0),d1       * the normalizing number of ars's
        asl.l   #1,d1
        add.l   12(a0),d1       * actual divisor is 3*nars
        beq.s   nm3             * skip division by zero
        divs    d1,d0
        move.w  d0,d2
        ext.l   d2
        asl.l   #7,d2
        swap    d0
        ext.l   d0
        asl.l   #7,d0
        divs    d1,d0
        ext.l   d0
        add.l   d2,d0
        move.l  d0,(a0)+
        move.l  (a0),d0
        divs    d1,d0
        move.w  d0,d2
        ext.l   d2
        asl.l   #7,d2
        swap    d0
        ext.l   d0
        asl.l   #7,d0
        divs    d1,d0
        ext.l   d0
        add.l   d2,d0
        move.l  d0,(a0)+
        move.l  (a0),d0
        divs    d1,d0
        move.w  d0,d2
        ext.l   d2
        asl.l   #7,d2
        swap    d0
        ext.l   d0
        asl.l   #7,d0
        divs    d1,d0
        ext.l   d0
        add.l   d2,d0
        move.l  d0,(a0)+
        adda.l  #4,a0
nm2:    suba.w  #1,d6
```

```
        bne.s   nm1
        rts
nm3:    lea     16(a0),a0           * skip group of 3 samples & count
        bra.s   nm2

_avrs:
        move.l  _pzbar,a1
        move.l  _pqrsb,a2
        move.l  a1,d1               * if (pb == 0) ....
        bne     avrs20 tst.l   16(a2)
        beq.s   avrs1
        movea.l #-1,d0
        move.l  d0,16(a2)           * if (pc->avtyp != 0)
        rts                         *    pc->avtyp = -1, return;

avrs1:  movem.l d3-d5,-(sp)
        move.l  24(a2),a1
        add.w   #12,a1               * pb = pc->pzbari + 3
        adda.l  #1,(a1)+             * *pb++ += 1;
        move.l  20(a2),a0            * pz = pc->pcycle
        move.l  (a0)+,_z0
        move.w  (a0)+,_z0+4          * z0[0] = *pz++, z0[1] = *pz++, z0[2] = *pz++
        cmp.l   #_zin+15000,a0
        bcs.s   avrs2
        lea     -15000(a0),a0        * if (pz >= zin+NLD*NRAW) pz -= NLD*NRAW avrs2:  move.l  a1,a2                * pc = pb
        move.w  _z0,d3
        move.w  _z0+2,d4
        move.w  _z0+4,d5
avrs3:  cmp.l   #_zbar+4800,a1
        bcc.s   avrs4                * for (; pb < zbar+QTRGGR*16-400;) ...
        move.w  (a0)+,d0
        sub.w   d3,d0
        ext.l   d0
        add.l   d0,(a1)+
        move.w  (a0)+,d0
        sub.w   d4,d0
        ext.l   d0
        add.l   d0,(a1)+
        move.w  (a0)+,d0
        sub.w   d5,d0
        ext.l   d0
        add.l   d0,(a1)+
        adda.l  #1,(a1)+
        cmp.l   #_zin+15000,a0
        bcs.s   avrs3
        lea     -15000(a0),a0
        bra.s   avrs3 avrs4:  move.l  a0,_pzraw
        move.l  a1,_pzbar move.l  _rr16,d0
        asl.l   #2,d0
        move.l  a7,a1
        adda.l  d0,a1
```

```
        cmp.l   #_zbar+12800,a1
        bcs.s   avrg41
        move.l  #_zbar+12800,a1
avrg41: move.l  _avzn,d3
        move.l  _avzn+4,d4
        move.l  _avzn+8,d5 avrg5:  move.l  -64(a2),d0
        asl.l   #1,d0
        sub.l   (a2),d0
        sub.l   -128(a2),d0
        bpl.s   avrg6
        neg.l   d0
avrg6:  asl.l   #5,d0
        cmp.l   d3,d0
        blt.s   avrg7
        addq.l  #2,d3
avrg7:  subq.l  #1,d3 move.l  -60(a2),d0
        asl.l   #1,d0
        sub.l   4(a2),d0
        sub.l   -124(a2),d0
        bpl.s   avrg8
        neg.l   d0
avrg8:  asl.l   #5,d0
        cmp.l   d4,d0
        blt.s   avrg9
        addq.l  #2,d4
avrg9:  subq.l  #1,d4 move.l  -56(a2),d0
        asl.l   #1,d0
        sub.l   8(a2),d0
        sub.l   -120(a2),d0
        bpl.s   avrg10
        neg.l   d0
avrg10: asl.l   #5,d0
        cmp.l   d5,d0
        blt.s   avrg11
        addq.l  #2,d5
avrg11: subq.l  #1,d5 adda.w  #64,a2
        cmp.l   a1,a2
        bcs.s   avrg5
        move.l  d3,_avzn
        move.l  d4,_avzn+4
        move.l  d5,_avzn+8
        movem.l (sp)+,d3-d5
        rts avrg20: cmp.l   #_zbar+12800,a1
        bcc     avrg30 move.l  _pzraw,a0
        move.w  _z0,d0
        move.w  _z0+2,d1
        move.w  _z0+4,d2
        moveq.l #4,d7
```

```
avrs21:  move.w   (a0)+,d6
         sub.w    d0,d6
         ext.l    d6
         add.l    d6,(a1)+
         move.w   (a0)+,d6
         sub.w    d1,d6
         ext.l    d6
         add.l    d6,(a1)+
         move.w   (a0)+,d6
         sub.w    d2,d6
         ext.l    d6
         add.l    d6,(a1)+
         adda.l   #1,(a1)+
         cmp.l    #_zin+15000,a0
         bcs.s    avrs22
         lea      -15000(a0),a0 avrs22:  suba.w   #1,d7
         bne.s    avrs21 avrs24:  move.l   a0,_pzraw        * pzraw = pz
         move.l   a1,_pzbar        * pzbar = pb
         rts                       * return avrs30:  moveq.l  #-1,d0
         move.l   d0,16(a2)        * pc->avtyp = -1
         clr.l    _pzbar           * pzbar = 0
         rts                       * return
```

What is claimed is:

1. An apparatus for averaging a plurality of electrocardiographic waveforms having P, Q, R, S, and T-segments to form a means for sampling said plurality of electrocardiographic waveforms periodically and for generating a sequence of input data samples indicating the amplitude of the electrocardiographic waveforms at each sampled time;

means for selectively filtering a first frequency spectrum from said input data samples to produce first filtered data samples, said first frequency spectrum corresponding to the major signal frequency components of the QRS-segments of the waveforms;

means for detecting heartbeat waveforms from said input data samples corresponding to said first filtered data samples;

means for selectively filtering a second frequency spectrum from said input data samples to produce second filtered data samples, said second frequency spectrum having a greater bandwidth than said first frequency spectrum to include major signal frequencies of the P, Q, R, S, and T-segments of the waveforms;

means for classifying heartbeat waveforms from said input data samples into different heartbeat types corresponding to said second filtered data samples and said detected heartbeat waveforms;

means for identifying representative heartbeat waveforms from said input data samples corresponding to at least one type of said classified heartbeat waveforms; and means for averaging said representative heartbeat waveforms into the composite heartbeat waveform.

2. An apparatus as defined in claim 1 which further includes:

means for marking an equivalent time reference in each representative heartbeat waveform by marking each representative heartbeat waveform at a reference sample; and means for aligning each of the representative heartbeat waveforms based on said reference sample marking prior to averaging.

3. An apparatus as defined in claim 1 wherein the electrocardiographic waveforms exhibit a dominant rhythm pattern and which further includes:

means for whether each detected heartbeat waveform belongs to the dominant rhythm pattern of the waveforms; and means for discarding those detected heartbeat waveforms not classified as belonging to the dominant rhythm prior to averaging.

4. An apparatus as defined in claim 1 which further includes:

means for high pass filtering said composite heartbeat waveform.

5. An apparatus as defined in claim 1 which further includes:

means for detecting high frequency, low amplitude features of said composite heartbeat waveform.

6. An apparatus as defined in claim 5, wherein said detecting means comprises:

a high pass filter which provides an output in the frequency spectrum over 40 Hz.

7. An apparatus as defined in claim 6 wherein said high pass filter comprises:

a finite impulse filter having a sampling equation defining samples of a waveform as a function of the other samples of the waveform which obtains a finite number of samples of said composite heartbeat and filters the obtained samples according to the sampling equation to generate a filtered sample for each sample of the composite heartbeat.

8. An apparatus as defined in claim 7 wherein said sampling equation comprises:

$$S_f = \frac{S(7) + S(8)}{8} - \sum_{i=0}^{i=15} Si/16$$

where $$\sum_{i=0}^{i=15} Si/16$$

is the average of the next sixteen data samples subsequent to the sample $S_O$,

S(7), S(8) are the seventh and eighth data samples subsequent to the sample $S_O$, and $S_f$ is the filtered data sample corresponding to the actual data Sample $S_O$.

9. An apparatus as defined in claim 6 wherein said high pass filter comprises:

a four pole Butterworth filter which obtains the samples of said average beat waveform and filters the samples according to a sampling equation to generate a filtered sample for each sample of the average beat data.

10. An apparatus as defined in claim 9 wherein said sampling equation is a digital synthesis of the analog transfer function:

$$T(s) = \frac{1}{1 + \frac{C1}{S} + \frac{1}{S^2}} \cdot \frac{1}{1 + \frac{C2}{S} + \frac{1}{S^2}}$$

where

T(s) = the transfer function in the Laplace or frequency domain, and

C1, C2 = are constants setting the frequency response of the filter.

11. An apparatus for sampling a plurality of electrocardiographic waveform indicative of corresponding potentials from surface electrodes placed on a living body comprising:

means for sampling the plurality of waveforms periodically and for generating data samples indicating the amplitude of the waveforms at each sampled time;

said data samples containing parallel sample values for each electrode for each cycle of the sampling period;

means for filtering high frequency noise from said data samples such that high frequency signals in excess of one half the sampling rate are attenuated;

means for averaging the parallel sample values of each electrode to generate electrode sample values corresponding to a waveform from a single electrode; and means for differencing corresponding electrode sample values to generate a heartbeat waveform representative of an electrocardiographic potential through one axis of the body.

12. An apparatus for sampling as defined in claim 11 wherein the surface electrodes are disposed on the body such that three waveforms are generated from three axes passing through the heart which are mutually perpendicular to one another.

13. An apparatus for sampling as defined in claim 11 which further includes:

means for averaging a plurality of electrode samples values such that the average forms one sample whereby aliasing components of the sampling frequency are attenuated.

14. An apparatus as defined in claim 11 wherein said means for sampling comprises:

means for digitizing said samples into difference samples as the difference between the present analog value of one of the potentials from said electrodes and the last previous value of that one potential; and means for transmitting said difference samples to a storage means.

15. An apparatus as defined in claim 14 which further includes:

means for integrating said stored difference samples back into data samples representative of the potential values of the waveforms at each sampled position.

16. An apparatus as defined in claim 15 which further includes:

means for determining the maximum amplitude difference between input samples of a heartbeat waveform, and means for comparing said maximum difference to a reference value indicative of the maximum difference for living body and for generating a pacer signal indicating the detection of an artificial pacing pulse if the determined difference is greater than the reference value.

17. A method for averaging a plurality of electrocardiographic heartbeat waveforms, having a QRS-segment and formatted as sucessive digital samples in a data stream, into an average heartbeat representation, said method comprising the steps of:

filtering said samples with a first band pass filter having a frequency pass band related to the major signal frequency components of the QRS-segment of an electrocardiographic heartbeat waveform, said first bandpass filter forming a set of detection samples corresponding to each of said digital samples;

filtering each of said samples with a second bandpass filter having a frequency pass band related to the major signal frequency components of the QRS complex of an electrocardiographic beat waveform but wider than the pass band of the first bandpass filter, said second bandpass filter forming a set of classification samples corresponding to each of said digital samples;

forming a template of template sample values corresponding to said sample values from said detection samples and said classification samples;

calculating a ratio for each sample value as the absolute value of the difference between a sample value and the corresponding template sample value divided by the absolute value of the sum of the sample value and the corresponding template sample value;

comparing said calculated ratios to determine the minimum ratio; and identifying the digital sample value at which the minimum ratio for a heartbeat waveform occurs.

18. A method for analyzing electrocardiographic signals to determine the level of high frequency energy in the late QRS-segment, comprising the steps of:

sampling a plurality of heartbeat waveforms periodically;

generating data samples indicating the amplitude of the waveforms at each sample time;

selectively filtering a first frequency spectrum from said data samples to produce first filtered data samples, said first frequency spectrum correspnding to the major signal frequency components of the QRS-segments of the waveforms;

selectively filtering a second frequency spectrum from said data samples to produce second filtered data samples, wherein said second frequency spectrum has a greater bandwidth than said first frequency spectrum;

detecting heartbeat waveforms as a sequence of said data samples with said first filtered data from said generated data samples;

classifying said detected heartbeat waveforms as to type with said second filtered data samples;

averaging at least one type of said classified heartbeat waveforms into a sequence of data samples forming a composite heartbeat waveform;

applying at least a portion of the late QRS-segments of said composite heartbeat sequence in reverse time order to high pass filter means; and determining the level of high frequency energy output from said high pass filter means.

19. The method as set forth in claim 18 wherein the step of applying includes:

applying the last 40 milliseconds of the QRS-segment of the composite waveform to said high pass filter means.

20. The method as set forth in claim 19 wherein the step of determining includes:

calculating the high frequency energy level as the root mean square of the output of said filter means.

* * * * *

UNITED STATES PATENT AND TRADEMARK OFFICE
CERTIFICATE OF CORRECTION

PATENT NO. : 4,630,204
DATED : December 16, 1986
INVENTOR(S) : David W. Mortara

It is certified that error appears in the above-identified patent and that said Letters Patent is hereby corrected as shown below:

IN THE DRAWINGS:

Sheet 2, FIG. 4, in blocks 219, 221 and 225 QR5 should read QRS.

Sheet 17, FIG. 13, the block captioned "6" KEY? should be denoted A244.

Figure 14A:
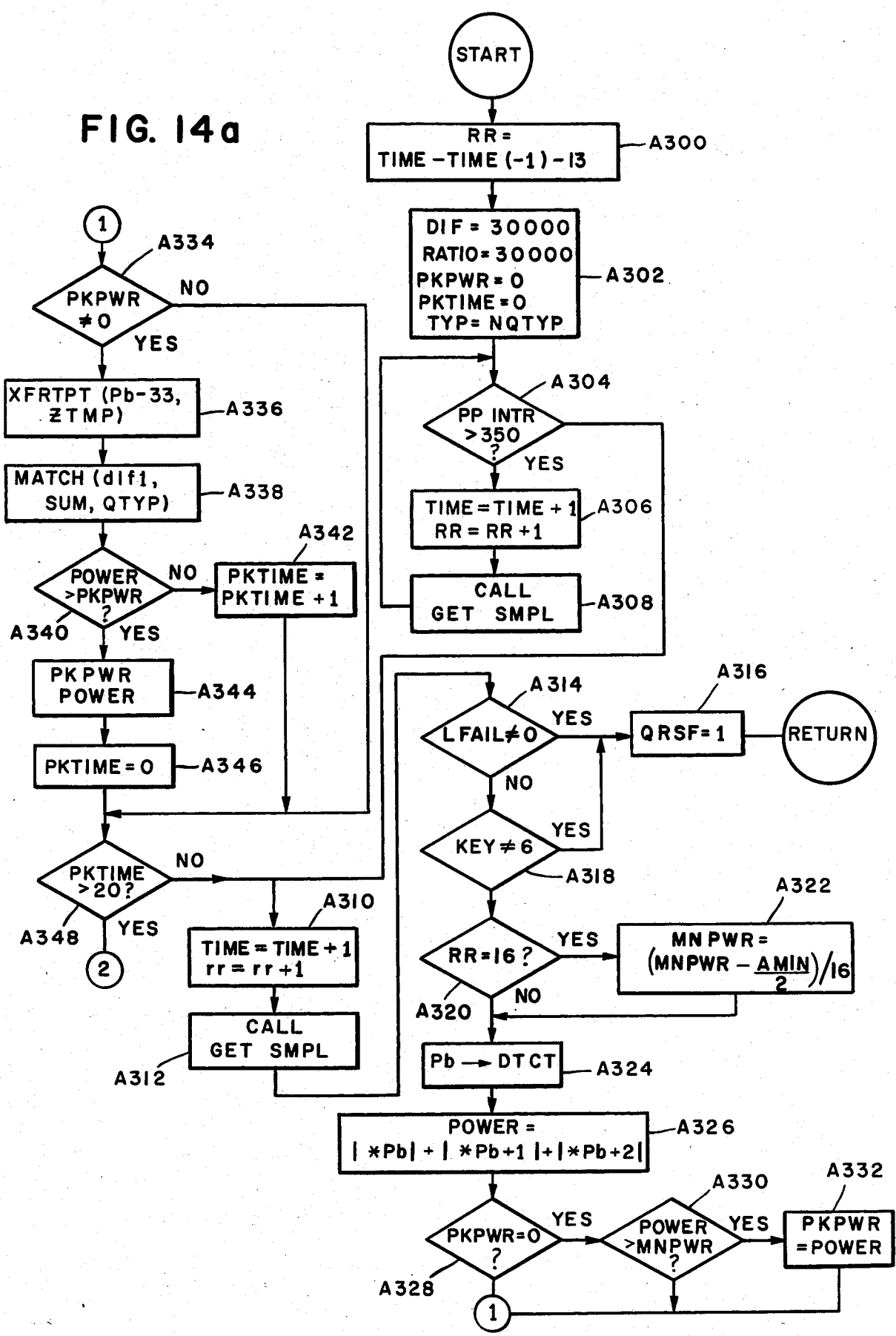
FIGS. 14a-14c form a detailed system flow chart for the routine QRSDCT illustrated in FIG. 13.

Sheet 18, FIG. 14a, the caption in block A300 should read:
RR = TIME - LTIME - 13

Sheet 18, FIG. 14a, the equation in block A310 reading rr = rr + 1 should read RR = RR + 1

Sheet 18, FIG. 14a, the caption in block A344 should read:
PKPWR = POWER

Figure 14B:
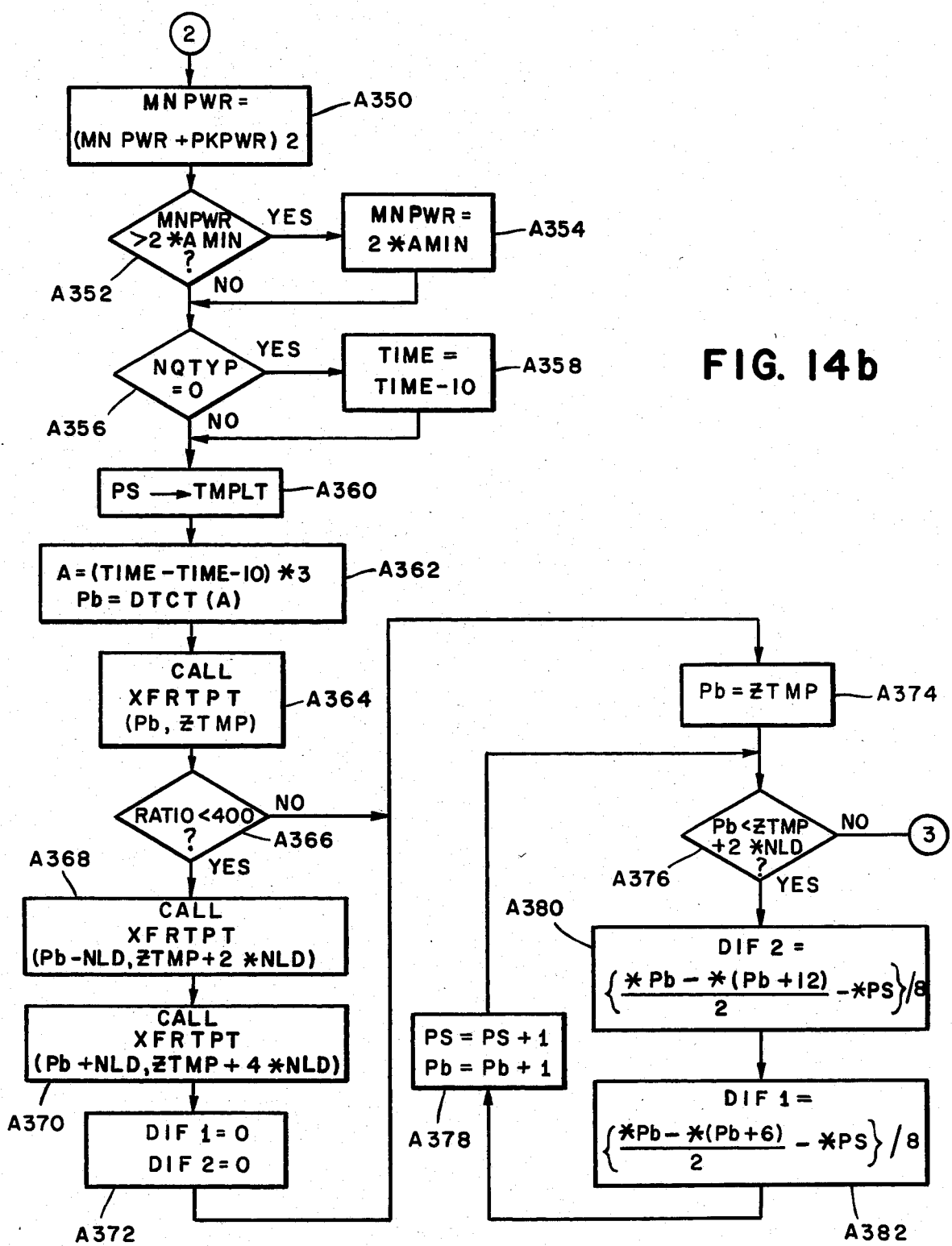

Sheet 19, FIG. 14b, the equation in block A350 should read:
MNPWR = (MNPWR + PKPWR)/2

Sheet 19, FIG. 14b, the equation in block A358 should read:
LTIME = TIME - 10

Sheet 19, FIG. 14b, the first equation in block A362 should read:
A = (LTIME - TIME - 10)*3

UNITED STATES PATENT AND TRADEMARK OFFICE
CERTIFICATE OF CORRECTION

PATENT NO. : 4,630,204

DATED : December 16, 1986

INVENTOR(S) : David W. Mortara

Figure 14C:
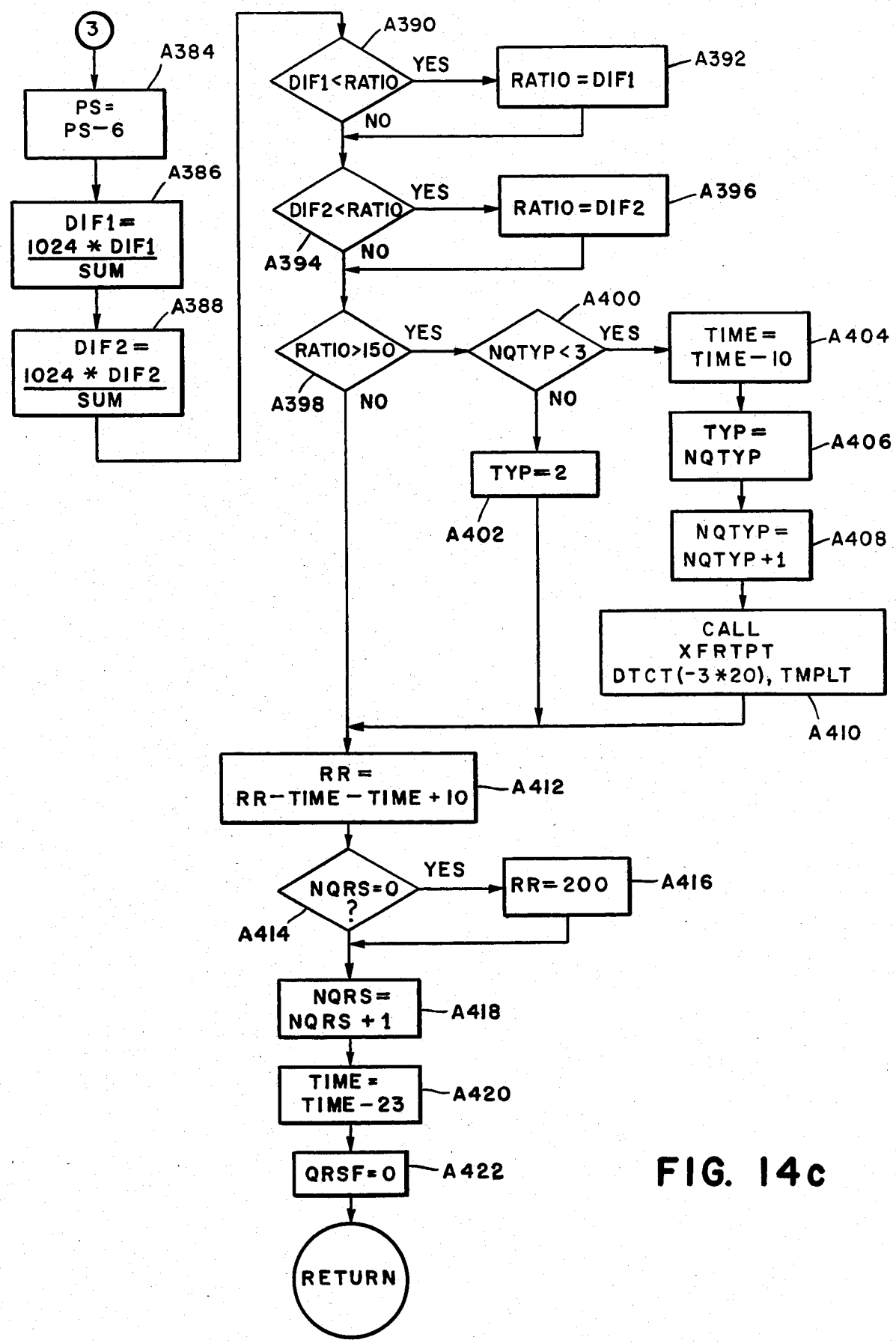

It is certified that error appears in the above-identified patent and that said Letters Patent is hereby corrected as shown below:

Sheet 20, FIG. 14c, the equation in block A404 should read:

LTIME = TIME - 10

Sheet 20, FIG. 14c, the equation in block A412 should read:

RR = RR - LTIME + TIME + 10

Figure 16A:
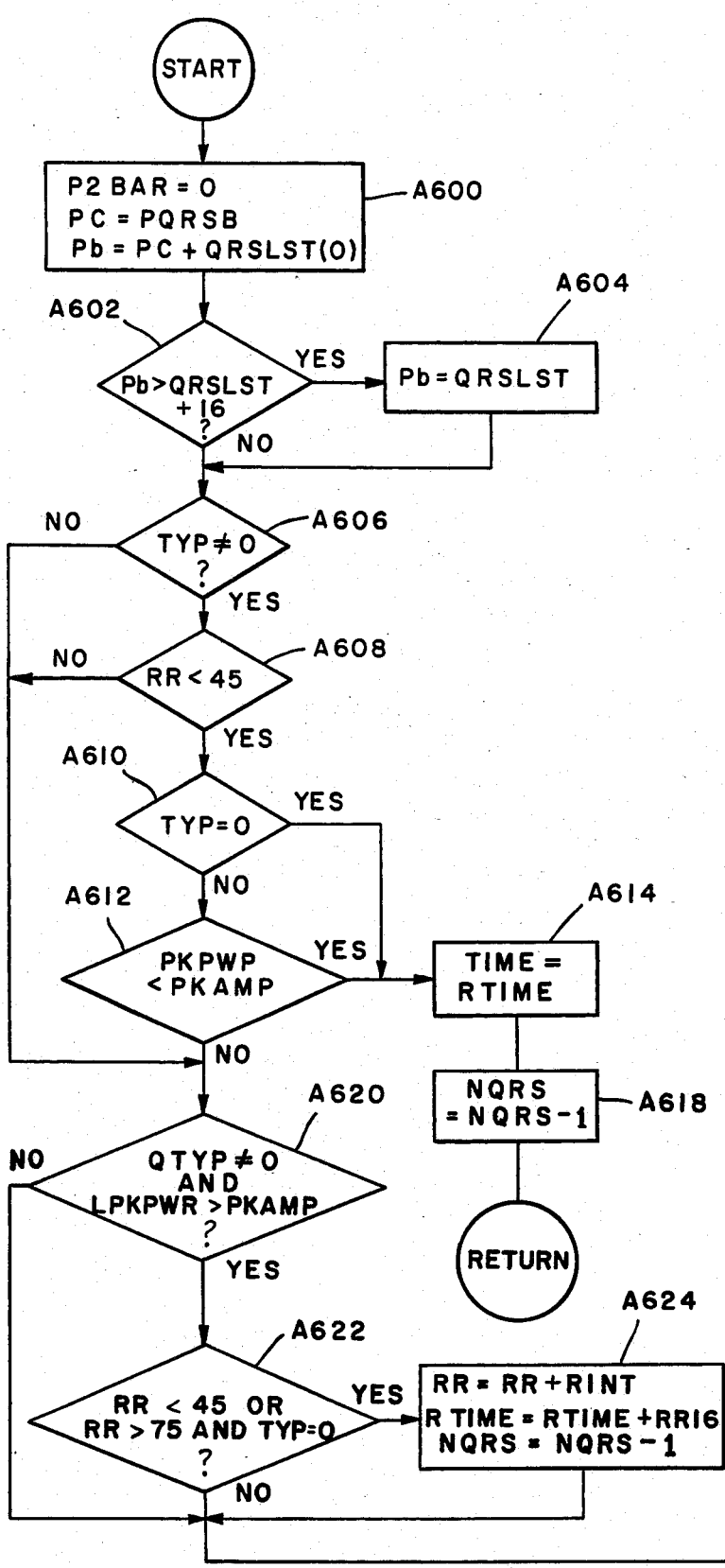
FIG. 16a-16b form a detailed flow chart of the routine RYTHM illustrated in FIG. 13.
Figure 16A:
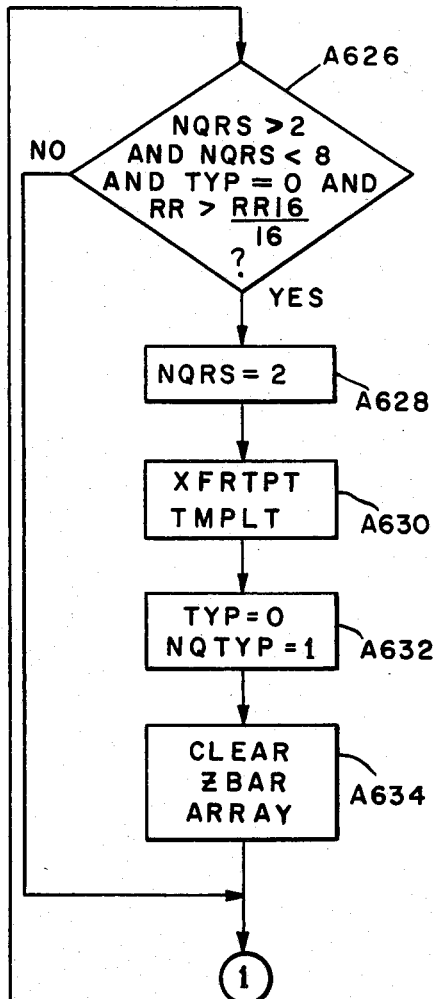

Sheet 24, FIG. 16a, the caption in block A600 should read:

PZBAR = 0
Pc = PQRSB
Pb = Pc + QRSLST(0)

Sheet 24, FIG. 16a, the caption in block A610 should read:

LTYP = 0

Sheet 24, FIG. 16a, the caption in block A612 should read:

PKPWR < LPKAMP

Figure 16B:
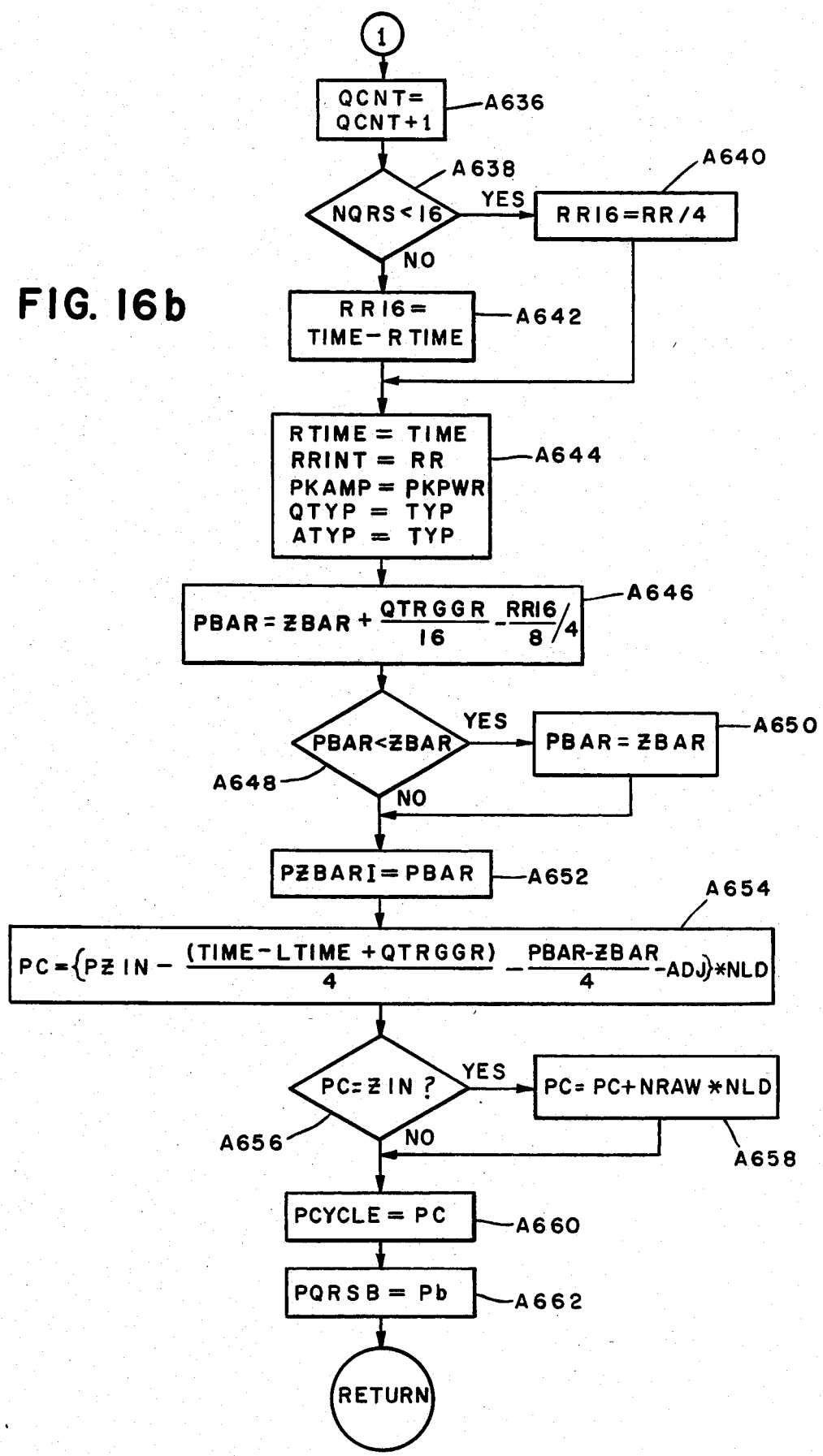

Sheet 25, FIG. 16b, in blocks A654, A656, A658 and A660:

PC should read Pc.

Figure 17:
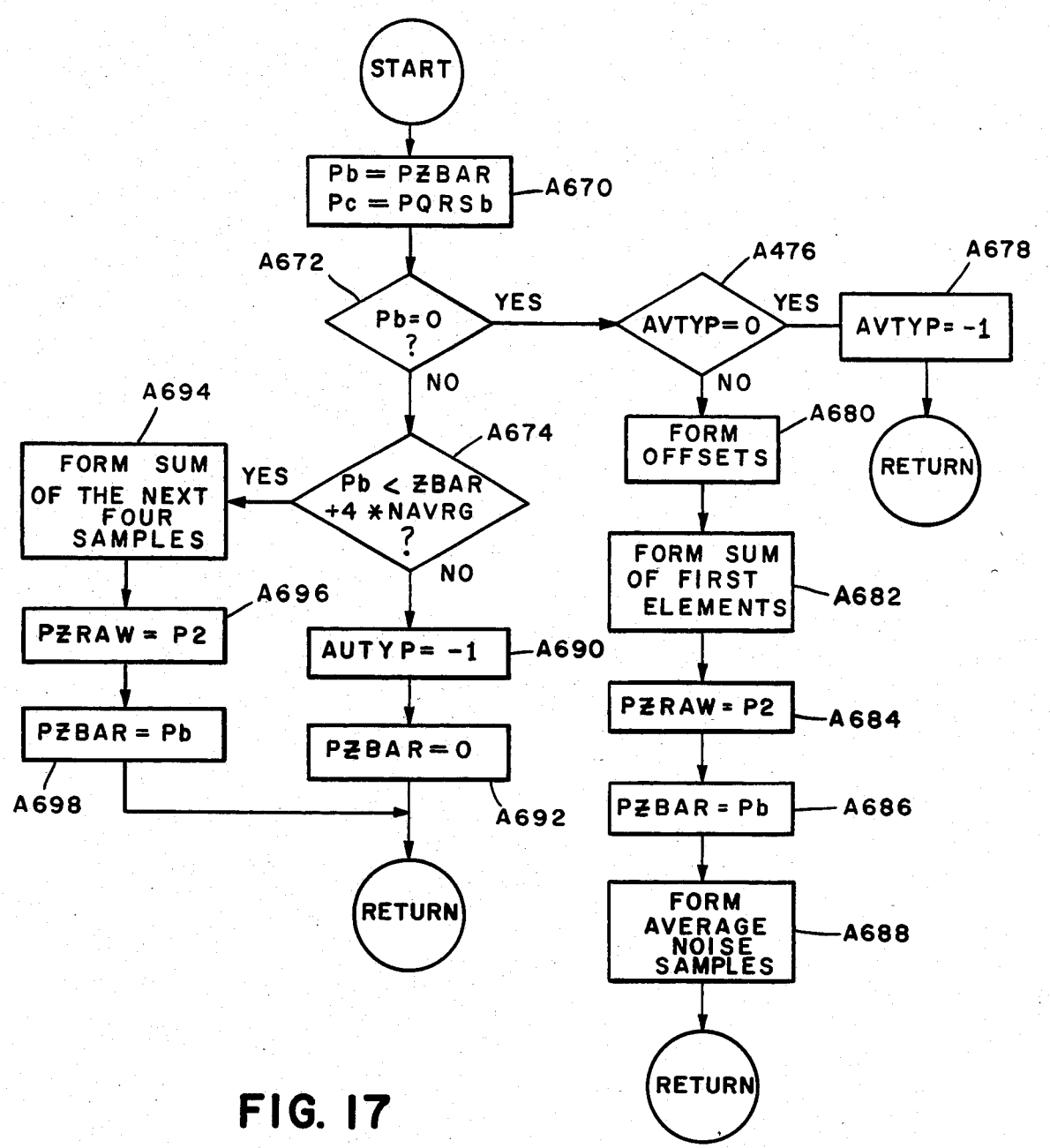
FIG. 17 is a detailed flow chart of the routine APRG which is called from the routine GETSMPL illustrated in FIG. 13.

Sheet 26, FIG. 17, the term in block A670 reading PQRSb should read:
PQRSB

UNITED STATES PATENT AND TRADEMARK OFFICE
CERTIFICATE OF CORRECTION

PATENT NO. : 4,630,204

DATED : December 16, 1986

INVENTOR(S) : David W. Mortara

It is certified that error appears in the above-identified patent and that said Letters Patent is hereby corrected as shown below:

Sheet 26, FIG. 17, the decision step denoted "A476" should be denoted --A676--;

Sheet 26, FIG. 17, in blocks A684 and A696, the term: P2 should read PZ.

Sheet 29, FIG. 22, in block 583 the term: LPN015 should read LPN01S.

Sheet 29, FIG. 22, the caption in block A598 should read:
NSUM = NSUM + *Pb

Column 1, line 20, change "Others" to --Other--.

Column 1, line 22, change "emperical" to read --empirical--.

In Column 1, line 37, change "discoveror" to read --discoverer--.

In Column 1, line 65, change "a ECG" to read --an ECG--.

In Column 2, line 27, after "positioning" insert --of--.

In Column 2, line 48, change "which" to --high--.

In Column 3, line 67, after "processor" insert the word --that--.

UNITED STATES PATENT AND TRADEMARK OFFICE
CERTIFICATE OF CORRECTION

PATENT NO. : 4,630,204

DATED : December 16, 1986

INVENTOR(S) : David W. Mortara

It is certified that error appears in the above-identified patent and that said Letters Patent is hereby corrected as shown below:

In Column 7, line 2, change "discernable" to read --discernible--.

In Column 7, line 18, change "discernable" to read --discernible--.

In Column 7, line 32, change "best" to read --beat--.

In Column 7, line 58, change "preprocessor means 200" to read --preprocessor means 202--.

In Column 7, line 62, change "main processor 202" to read --main processor 206--.

In Column 8, line 3, after the word "provided" insert the word --with--.

In Column 9, line 2, change "HZ" to read --Hz--.

In Column 9, line 6, change "KHz" to read --kHz--.

In Column 9, line 11, change "band pass" to read --bandpass--.

In Column 10, line 1, change "is" to read --are--.

In Column 11, line 29, after the word "ringing" insert the word --and--.

In Column 12, lines 6-7, after "FIG. 4" delete --however--.

UNITED STATES PATENT AND TRADEMARK OFFICE
CERTIFICATE OF CORRECTION

PATENT NO. : 4,630,204

DATED : December 16, 1986

INVENTOR(S) : David W. Mortara

It is certified that error appears in the above-identified patent and that said Letters Patent is hereby corrected as shown below:

In Column 12, line 46, change "to a" to read --to the--.

In Column 12, line 56, change "a" to read --an--.

In Column 12, line 65, change "a" to read --an--.

In Column 14, line 5, change "framming" to read --framing--.

In Column 14, line 66, change "memoran" to read the word --memory--.

In Column 15, line 11, change "accessable" to read --accessible--.

In Column 15, line 46, change "256" bold face typed to --256--.

In Column 16, line 22, change "PO7" to read --PD7--.

In Column 16, line 44, change "read write" to read --read/write--.

In Column 16, line 60, change "$\phi 02$" to read --$\phi 2$--.

In Column 17, line 46, change "Schaumberg" to read --Schaumburg--.

In Column 18, line 9, change "read write" to read --read/write--.

UNITED STATES PATENT AND TRADEMARK OFFICE
CERTIFICATE OF CORRECTION

PATENT NO. : 4,630,204
DATED : December 16, 1986
INVENTOR(S) : David W. Mortara It is certified that error appears in the above-identified patent and that said Letters Patent is hereby corrected as shown below:

In Column 18, line 52, change "read write" to --read/write--.

In Column 18, line 60, change "ANP" to read --AND--.

In Column 18, line 62, change "read write" to --read/write--.

In Column 19, line 12, change "signal" to read --single--.

In Column 19, line 20, change "a" to read --an--.

In Column 19, line 44, change "recieve" to read --receive--.

In Column 20, line 9, change "02" to read --$\phi 2$--.

In Column 20, line 60, change "writter" to read --written--.

In Column 21, line 21, change "A1D" to read --A/D--.

In Column 21, line 51, change "$V_s$" to read --$\Delta V_s$--.

In Column 21, line 55, change "$V_s$" to read --$\Delta V_s$--.

In Column 21, lines 61-62, change "intergrator" to read --integrator--.

UNITED STATES PATENT AND TRADEMARK OFFICE
CERTIFICATE OF CORRECTION

PATENT NO. : 4,630,204

DATED : December 16, 1986

INVENTOR(S) : David W. Mortara

It is certified that error appears in the above-identified patent and that said Letters Patent is hereby corrected as shown below:

In Column 22, line 65, change "206" to read --202--.

In Column 23, line 1, change "of 272" to read --272 of--.

In Column 23, line 45, after "found" insert a comma --,--.

In Column 23, line 45, after "program" delete the comma --,--.

In Column 23, line 50, change "and" to read --a--.

In Column 23, line 61, change "than" to read the word --then--.

In Column 24, line 7, after the word "return" insert --to--.

In Column 24, line 27, after the word "block" delete the word --in--.

In Column 24, line 33, change "prvious" to read --previous--.

In Column 24, line 34, change "variahle" to read --variable--.

In Column 25, line 39, before "X," delete --the--.

In Column 25, line 54, change "obstensible" to read --ostensible--.

UNITED STATES PATENT AND TRADEMARK OFFICE
CERTIFICATE OF CORRECTION

PATENT NO. : 4,630,204

DATED : December 16, 1986

INVENTOR(S) : David W. Mortara

It is certified that error appears in the above-identified patent and that said Letters Patent is hereby corrected as shown below:

In Column 25, line 67, after "time" insert --(LTIME)--.

In Column 26, line 43, change "value" to read --values--.

In Column 27, line 23, change "TIME" to read --LTIME--.

In Column 27, line 28, change "PB" to read --Pb--.

In Column 27, line 36, change "block" to read --blocks--.

In Column 27, line 48, change "block" to read --blocks--.

In Column 27, line 49, change "PB" to read --Pb--.

In Column 27, line 54, change "are" to read --is--.

In Column 28, line 4, change "O" to read --0--.

In Column 28, line 12, before the word "one" insert --by--.

In Column 28, line 24, after the word "set" insert --equal--.

In Column 28, line 26, after "detected" insert the phrase --which is represented by the variable--.

In Column 28, line 32, change "fudicial" to read --fiducial--.

UNITED STATES PATENT AND TRADEMARK OFFICE
CERTIFICATE OF CORRECTION

PATENT NO. : 4,630,204

DATED : December 16, 1986

INVENTOR(S) : David W. Mortara

It is certified that error appears in the above-identified patent and that said Letters Patent is hereby corrected as shown below:

In Column 28, line 40, change "synch" to read --SYNCH--.

In Column 28, line 59, after the word "to" delete --the--.

In Column 30, line 1, change "than" to read --then--.

In Column 30, line 27, change "a" to read --an--.

In Column 30, line 36, change "RHYTHM" to read --RYTHM--.

In Column 30, line 42, change "O" to read --0--.

In Column 30, line 47, change "PC" to read --Pc--.

In Column 30, lines 49-51, change "Pc" to read --Pb is--.

In Column 30, line 68, change "LPKAM8" to read --LPKAMP.--.

In Column 31, line 33, change "O" to read --0--.

In Column 31, line 48, change "O" to read --0--.

In Column 32, line 37, change "A476" to read --A676--.

In Column 32, line 41, change "can not" to read --cannot--.

UNITED STATES PATENT AND TRADEMARK OFFICE
CERTIFICATE OF CORRECTION

PATENT NO. : 4,630,204
DATED : December 16, 1986
INVENTOR(S) : David W. Mortara It is certified that error appears in the above-identified patent and that said Letters Patent is hereby corrected as shown below:

In Column 32, line 45, change the word "that" to read --then--.

In Column 32, line 47, after the word "then" delete the word --an--.

In Column 33, line 1, change "prelimary" to read --preliminary--.

In Column 33, line 13, change "Pz" to read --PZ--.

In Column 33, line 36, change "Vecb" to read --VECB--.

In Column 33, line 37, change "Pc + 7 +" to read --Pc + 7--.

In Column 33, line 48, change "Vecb" to read --VECB--.

In Column 33, line 50, change "veca" to read --VECA--.

In Column 34, line 8, after the word "term" insert --is--.

In Column 34, line 14, change "Vecb" to read --VECB--.

In Column 34, line 14, change "the one half" to read --one half--.

In Column 34, line 41, change "YT(S)=z" to read --Y T(s) = Z--.

In Column 34, line 43, change "2" to read --Z--.

UNITED STATES PATENT AND TRADEMARK OFFICE
CERTIFICATE OF CORRECTION

PATENT NO. : 4,630,204
DATED : December 16, 1986
INVENTOR(S) : David W. Mortara It is certified that error appears in the above-identified patent and that said Letters Patent is hereby corrected as shown below:

In Column 35, line 15, change "Veca" to read --VECA--.

In Column 35, line 15, change "Vecb" to read --VECB--.

In Column 36, line 33, change "Vecb" to read --VECB--.

In Column 36, line 37, change "the the" to read --the--.

In Column 36, line 42, change "an" to --can--.

In Column 36, line 59, change "blocks" to read --block--.

In Column 37, line 4, change "blocks" to read --block--.

In Column 37, line 35, after "NMIN" insert the word --then--.

In Column 38, line 6, change "block" to read --blocks--.

In Column 38, line 28, change "illustrate" to read --illustrates--.

In Column 85, line 38, (Claim 1, line 4), after "a" insert the phrase --representative composite heartbeat signal, comprising:--.

UNITED STATES PATENT AND TRADEMARK OFFICE
CERTIFICATE OF CORRECTION

PATENT NO. : 4,630,204
DATED : December 16, 1986
INVENTOR(S) : David W. Mortara It is certified that error appears in the above-identified patent and that said Letters Patent is hereby corrected as shown below:

In Column 86, line 61, (Claim 6, line 1), after "Claim 5", delete the comma --,--.

In Column 87, line 35, (Claim 10, line 4, the equation reading:

$$T(s) = \frac{1}{1 + \frac{C1}{s} + \frac{1}{s^2} \quad 1 + \frac{C2}{s} + \frac{1}{s^2}}$$

should read:

$$T(s) = \frac{1}{\left(1 + \frac{C1}{s} + \frac{1}{s^2}\right)\left(1 + \frac{C2}{s} + \frac{1}{s^2}\right)}$$

In Column 87, line 45 (Claim 11, line 2), change "waveform" to read --waveforms--.

In Column 88, line 39, (Claim 17, line 3), change "sucessive" to read --successive--.

UNITED STATES PATENT AND TRADEMARK OFFICE
CERTIFICATE OF CORRECTION

PATENT NO. : 4,630,204

DATED : December 16, 1986

INVENTOR(S) : David W. Mortara

It is certified that error appears in the above-identified patent and that said Letters Patent is hereby corrected as shown below:

In Column 88, line 42, (Claim 17, line 6), change "band pass" to read --bandpass--.

In Column 89, line 12, (Claim 18, line 10), change "correspnding" to read --corresponding--.

Signed and Sealed this

Twenty-ninth Day of November, 1994

Attest:

BRUCE LEHMAN

Attesting Officer    Commissioner of Patents and Trademarks